US005599932A

United States Patent [19]
Bieniarz et al.

[11] Patent Number: 5,599,932
[45] Date of Patent: Feb. 4, 1997

[54] INTERCALATORS HAVING AFFINITY FOR DNA AND METHODS OF USE

[75] Inventors: Christopher Bieniarz, Highland Park; Jeffrey B. Huff, Park Ridge; Denis R. Henrard, Lake Forest, all of Ill.

[73] Assignee: Abbott Laboratories, Abbott Park, Ill.

[21] Appl. No.: 464,185

[22] Filed: Jun. 5, 1995

Related U.S. Application Data

[60] Division of Ser. No. 265,342, Jun. 23, 1994, which is a continuation-in-part of Ser. No. 86,285, Jun. 30, 1993, abandoned.

[51] Int. Cl.$^6$ .................................................. C07D 401/06
[52] U.S. Cl. .......................... 544/361; 546/108; 546/109
[58] Field of Search ................................. 546/108, 109; 544/361

[56] References Cited

U.S. PATENT DOCUMENTS

| | | | |
|---|---|---|---|
| 4,119,521 | 10/1978 | Chirikjian | 204/299 |
| 4,665,184 | 5/1987 | Dervan et al. | 546/109 |
| 4,921,805 | 5/1990 | Gebeyehu et al. | 435/270 |
| 4,981,977 | 1/1991 | Southwick et al. | 548/455 |
| 5,312,921 | 5/1994 | Glazer | 546/108 |

FOREIGN PATENT DOCUMENTS

| | | |
|---|---|---|
| 0301899A2 | 7/1988 | European Pat. Off. |
| PCT/US91/01604 | 9/1991 | WIPO. |
| 9308165 | 4/1993 | WIPO. |

OTHER PUBLICATIONS

Glazer, Alexander N., et al., "Stable Dye–DNA Intercalation Complexes As Reagents For High–Sensitivity Fluorescence Detection", *Nature*, 359, pp. 859–861 (Oct. 29, 1992).
Quesada, M. A., et al., "High–Sensitivity DNA Detection With A Laser–Excited Confocal Fluorescence Gel Scanner", *BioTechniques*, 10 (5), pp. 616–625 (1991).
Glazer, Alexander N., et al., "A Stable Double–Stranded DNA–Ethidium Homodimer Complex: Application To Picogram Fluorescence Detection Of DNA In Agarose Gels," *Proc. Natl. Acad. Sci. USA*, 87, pp. 3851–3855 (May 1990).
Rye, Hays S., et al., "Stable Fluorescent Complexes Of Double–Stranded DNA With Bis–Intercalating Asymmetric Cyanine Dyes: Properties And Applications", *Nucleic Acids Research*, 20 (11), pp. 2803–2812 (1990).
Rye, Hays S., et al., "High–Sensitivity Two–Color Detection Of Double–Stranded DNA With A Confocal Fluorescence Gel Scanner Using Ethidium Homodimer and Thiazole Orange", *Nucleic Acids Research*, 19 (2), pp. 327–333 (1990).
Mathies, Richard A., et al., "Capillary Array Electrophoresis: An Approach To High–Speed, High–Throughput DNA Sequencing", *Nature*, 359, pp. 167–169 (Sep. 10, 1992).
Gao, Qi, et al., "Drug–Induced DNA Repair: X–Ray Structure Of A DNA–Ditercalinium Complex", *Proc. Natl. Acad. Sci. USA*, 88, pp. 2422–2426 (Mar. 1991).

Mathies, Richard A., et al., "Optimization Of High–Sensitivity Fluorescence Detection", *Anal. Chem.*, 62 (17), pp. 1786–1791 (Sep. 1, 1990).
Peck, Konan, et al., "Single–Molecule Fluorescence Detection: Autocorrelation Criterion And Experimental Realization With Phycoerythrin", *Proc. Natl. Acad. Sci. USA*, 86, pp. 4087–4091 (Jun. 1989).
Severini, Alberto, et al., "An Assay For Proteinases And Their Inhibitors Based On DNA/Ethidium Bromide Fluorescence", *Anal. Biochem.*, 193, pp. 83–89 (1991).
Gaugain, Bernard, et al., "DNA Bifunctional Intercalators. I. Synthesis And Conformational Properties Of An Ethidium Homodimer And Of An Acridine Ethidium Heterodimer", *Biochemistry*, 17 (24), pp. 5071–5078 (Nov. 28, 1978).
Dervan, Peter B., et al., "Molecular Recognition Of DNA By Small Molecules, Synthesis Of Bis(methidium)spermine, A DNA Polyintercalating Molecule", *J. Chem. Soc.*, 100 (6), pp. 1968–1970 (Mar. 15, 1978).
Gaugain, Bernard, et al., "DNA Bifunctional Intercalators. 2. Fluorescence Properties And DNA Binding Interaction Of An Ethidium Homodimer And An Acridine Ethidium Heterodimer", *Biochemistry*, 17 (24), pp. 5078–5088 (1978).
Markovits, Judith, et al., "Ethidium Dimer: A New Reagent For The Fluorimetric Determination Of Nucleic Acids", *Anal. Biochem.*, 94, pp. 259–264 (1979).
Benson, Scott C., et al., "Heterodimeric DNA–Binding Dyes Designed For Energy Transfer: Stability And Applications Of The DNA Complexes", *Nucleic Acids Research*, 21 (24), pp. 5720–5726 (1993).
Petersen, S. E., "Accuracy And Reliability Of Flow Cytometric DNA Analysis Using A Simple, One–Step Ethidium Bromide Staining Protocol", *Cytometry*, 7 (4), pp. 301–306 (Jul., 1986).
Riboldi, et al., "Ethidium Bromide In The Detection Of Antibodies To DNA And Of Circulating DNA By Two–Stage Counterimmunoelectrophoresis", *J. Immunol. Methods*, 85 (1), pp. 217–220 (Dec. 17, 1985).
Denny, W. A., "DNA–Intercalating Ligands As Anti–Cancer Drugs: Prospects for Future Design", *Anticancer Drug Design*, 4, pp. 241–263 (Dec., 1989).
Benson, Scott C., et al., "Heterodimeric DNA–Binding Dyes Designed For Energy Transfer: Synthesis And Spectroscopic Properties", 21 (24), pp. 5727–5735 (1993).

(List continued on next page.)

*Primary Examiner*—C. Warren Ivy
*Assistant Examiner*—Evelyn Huang
*Attorney, Agent, or Firm*—David L. Weinstein

[57] ABSTRACT

Intercalator compounds are provided which are comprised of intercalator moieties, or substituted intercalator moieties, having one or more functionalized chains, or moieties, and which compounds provide a high affinity for binding to the DNA molecule and show reduced self-quenching, while providing superior transport kinetics. The compounds have been found to provide enhanced fluorescence when bound to a DNA molecule within a fluorescent flow cytometry environment which is about eight to ten times brighter in fluorescence than "bis" structure conventional intercalating agents and other known intercalating agents utilized in flow cytometry environment.

2 Claims, 43 Drawing Sheets

OTHER PUBLICATIONS

Sasaki, et al., "Discrimination Of Viable and Non–Viable Cells Using Propidium Iodide In Two Color Immunofluorescence", *Cytometry*, 8, pp. 413–420 (1987).

Mishell, et al., "Selected Methods In Immunology", pp. 10–17 (1980).

Ernst, et al., "Cyanine Dye Labeling Reagents For Sulfhydryl Groups", *Cytometry*, 10, pp. 3–10 (1989).

Hamer, Frances M., "The Cyanine Dyes And Related Compounds", John Wiley & Sons, pp. 34–39 (1964).

Wiberg, Kenneth B., et al., "Solvolysis of cis– and trans–Fused Bicyclo[4.2.0]octyl 7–Tosylates", *J. Am. Chem. Soc.*, 92:3, pp. 553–564 (Feb. 11, 1970).

Wilt, James W., "Reaction of 2–($\Delta^3$–Cyclopentenyl)ethyl Bromide with Tri–n–butyltin Hydride. Cyclization to Norbornane", *J. Org. Chem.*, 35:8, pp. 2803–2806 (1970).

Hooz, J., et al., "A Rapid, Mild Procedure for the Preparation of Alkyl Chlorides and Bromides", *Can. J. Chem.*, 46:86, pp. 86–87 (1968).

Lee, et al., "Preparation of Acyl Halides Under Very Mild Conditions", *J. Am. Chem. Soc.*, 88:14, pp. 3440–3441 (Jul. 20, 1966).

Christen, et al., "An Ethidium Bromide–Agarose Plate Assay for the Nonradioactive Detection of cDNA Synthesis", *Anal. Biohem.*, 178:2, pp. 269–272 (1989).

Jaycox, Gary D., et al., "Potential DNA bis–Intercalating Agents: Synthesis and Antitumor Activity of Novel, Conformationally Restricted bis(9–Aminoacridines)", *J. Heterocyclic Chem.*, 24, pp. 1405–1408 (Sep.–Oct. 1987).

Orchin, Milton, et al., *The Vocabulary of Organic Chemistry*, Wiley, p. 94 (1980).

Morrison, Robert Thornton, et al., *Organic Chemistry*, Allyn and Bacon, Inc., p. 1002 (1973).

Reques, Bernard P., et al., "Pharmacologie Moleculaire", *C. R. Acad. S. Paris*, 283, pp. 1365–1367 (Nov. 1976).

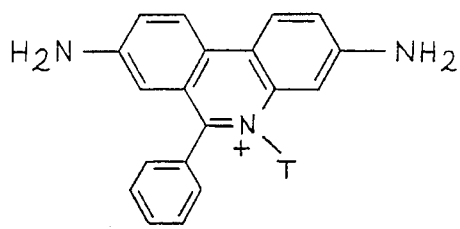
PHENANTHRIDINIUM
1
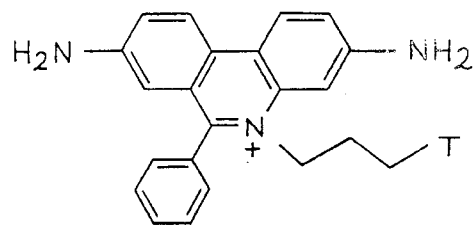
2
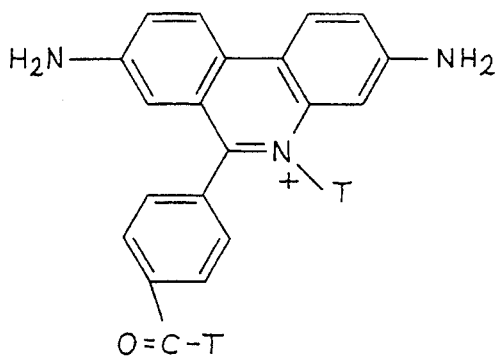
3
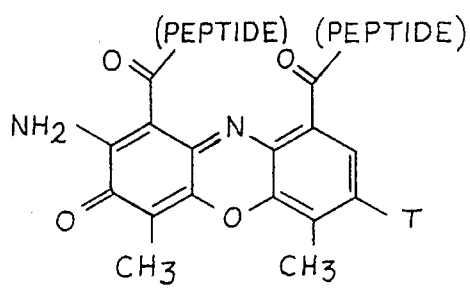
ACTINOMYOCIN
4
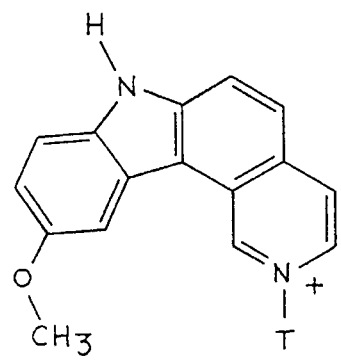
5
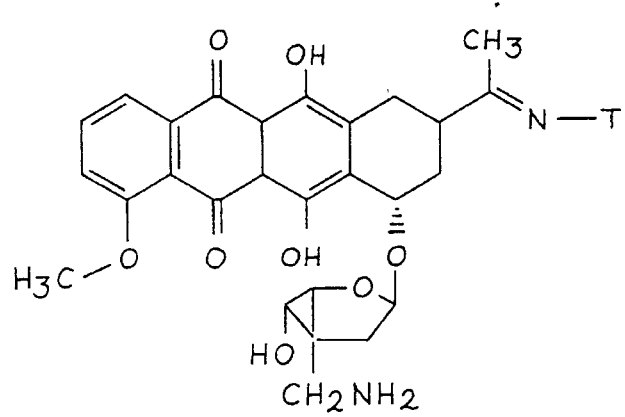
6
Fig. 13A

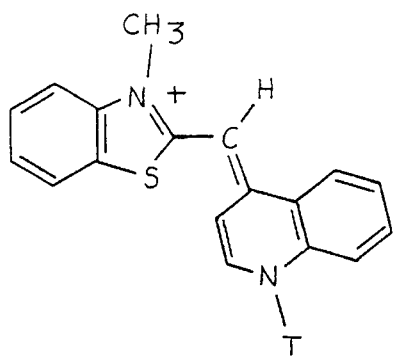
THIAZOLE ORANGE
7
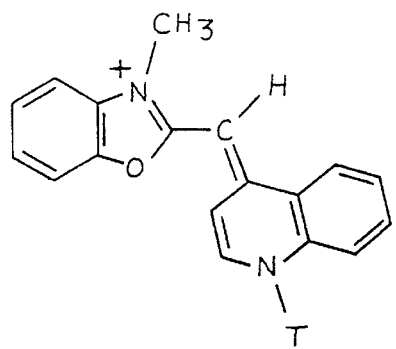
OXAZOLE YELLOW
8
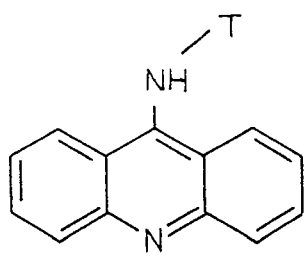
9
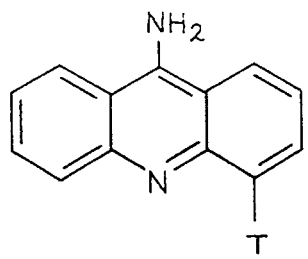
10
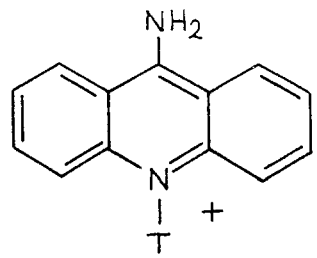
11
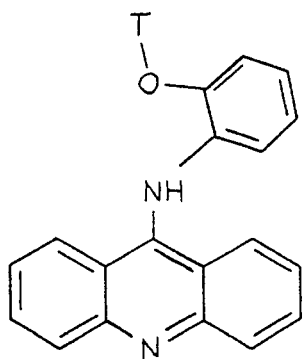
12
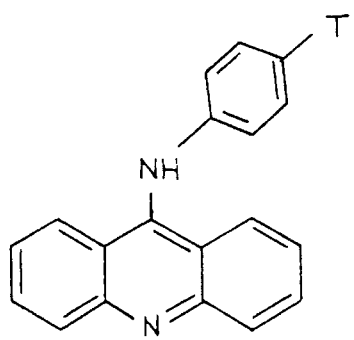
13
9-AMINOACRIDINES
Fig. 13B

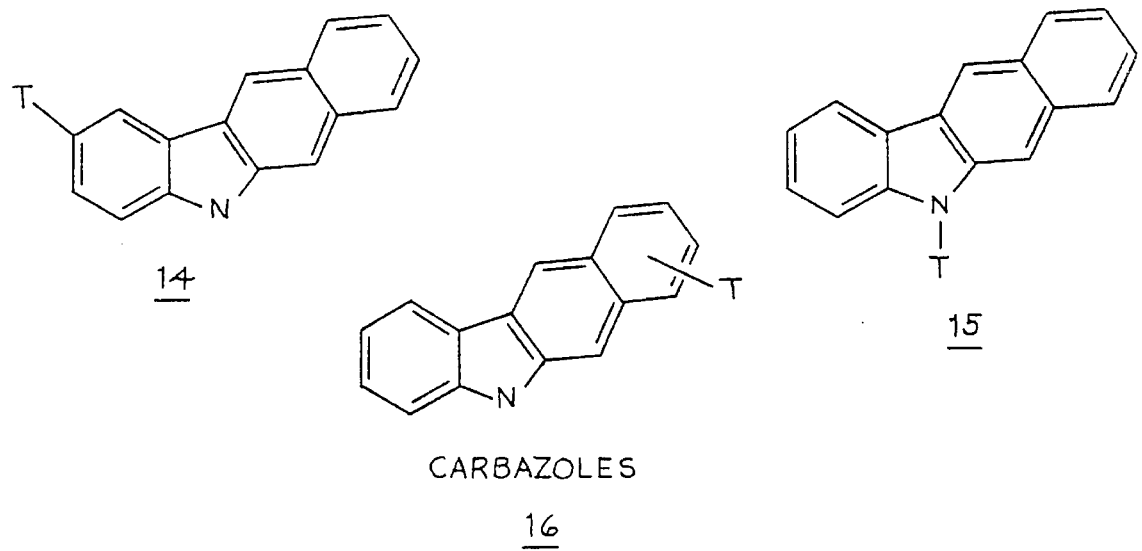
CARBAZOLES
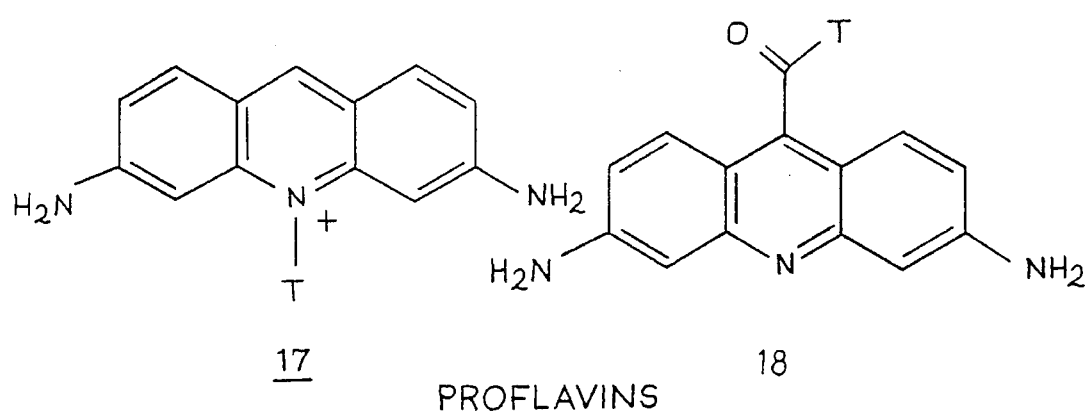
PROFLAVINS
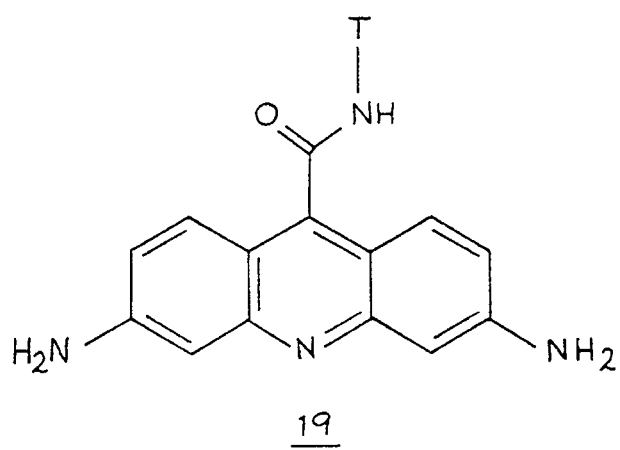
Fig. 13c

Fig. 16
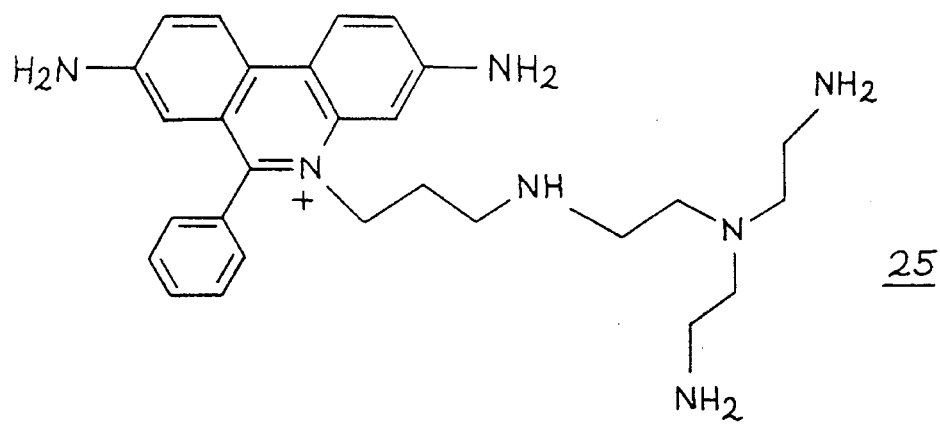
25
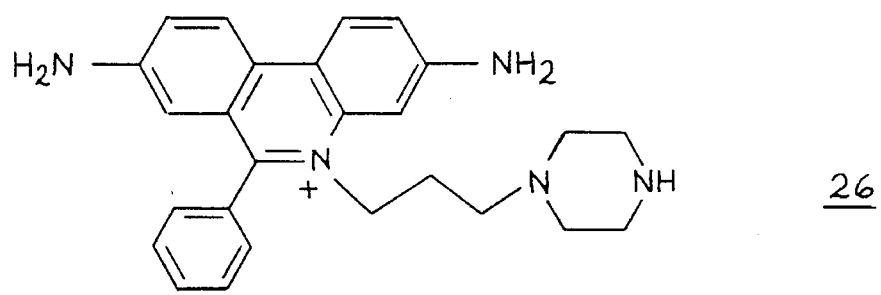
26
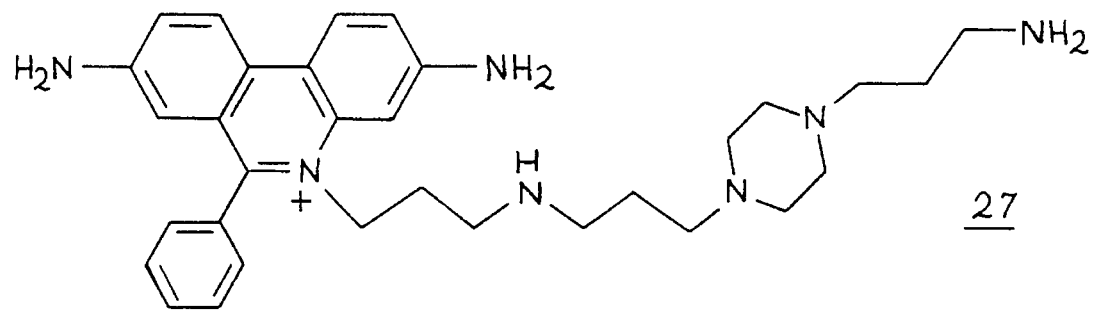
27

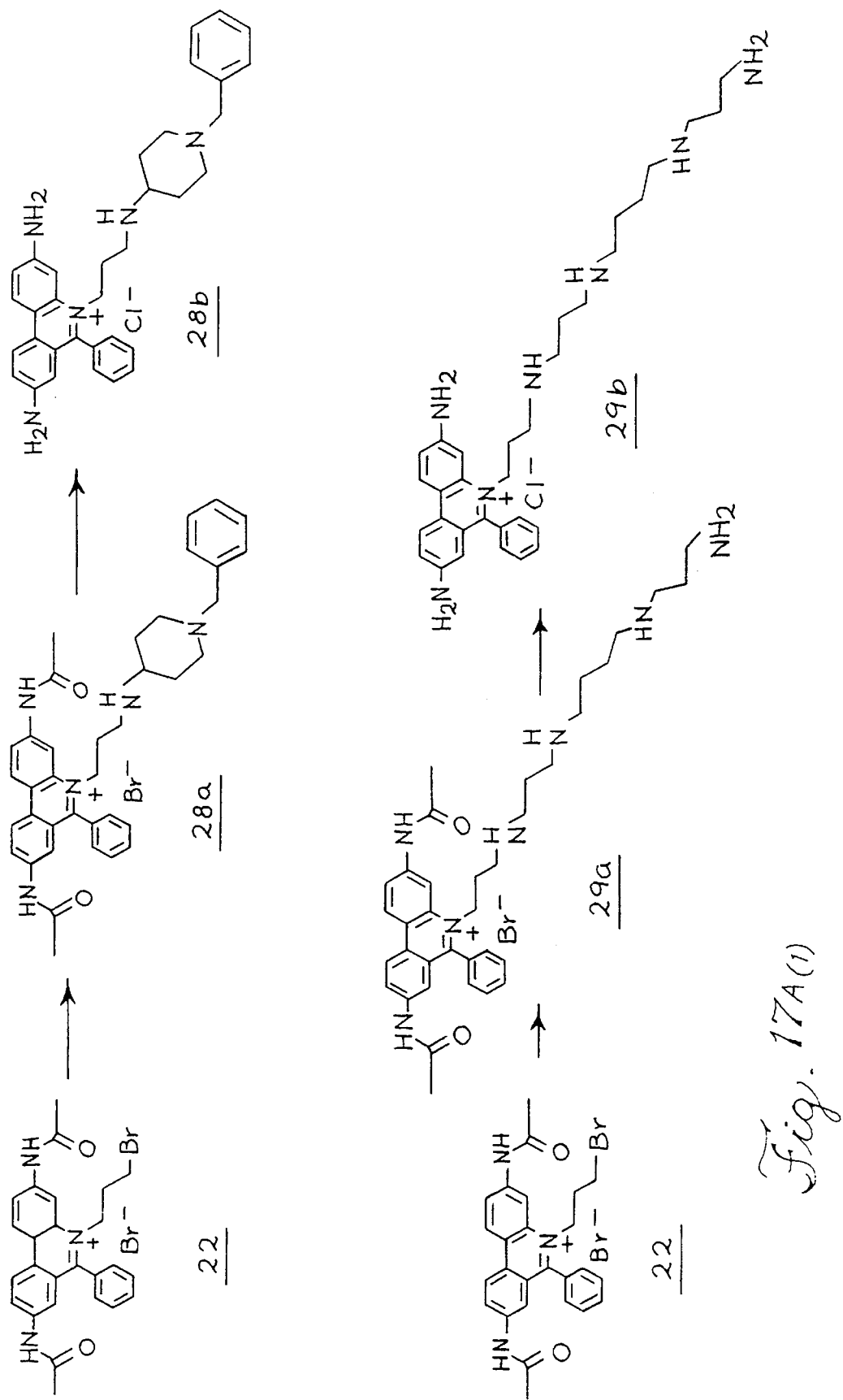
Fig. 17A(1)

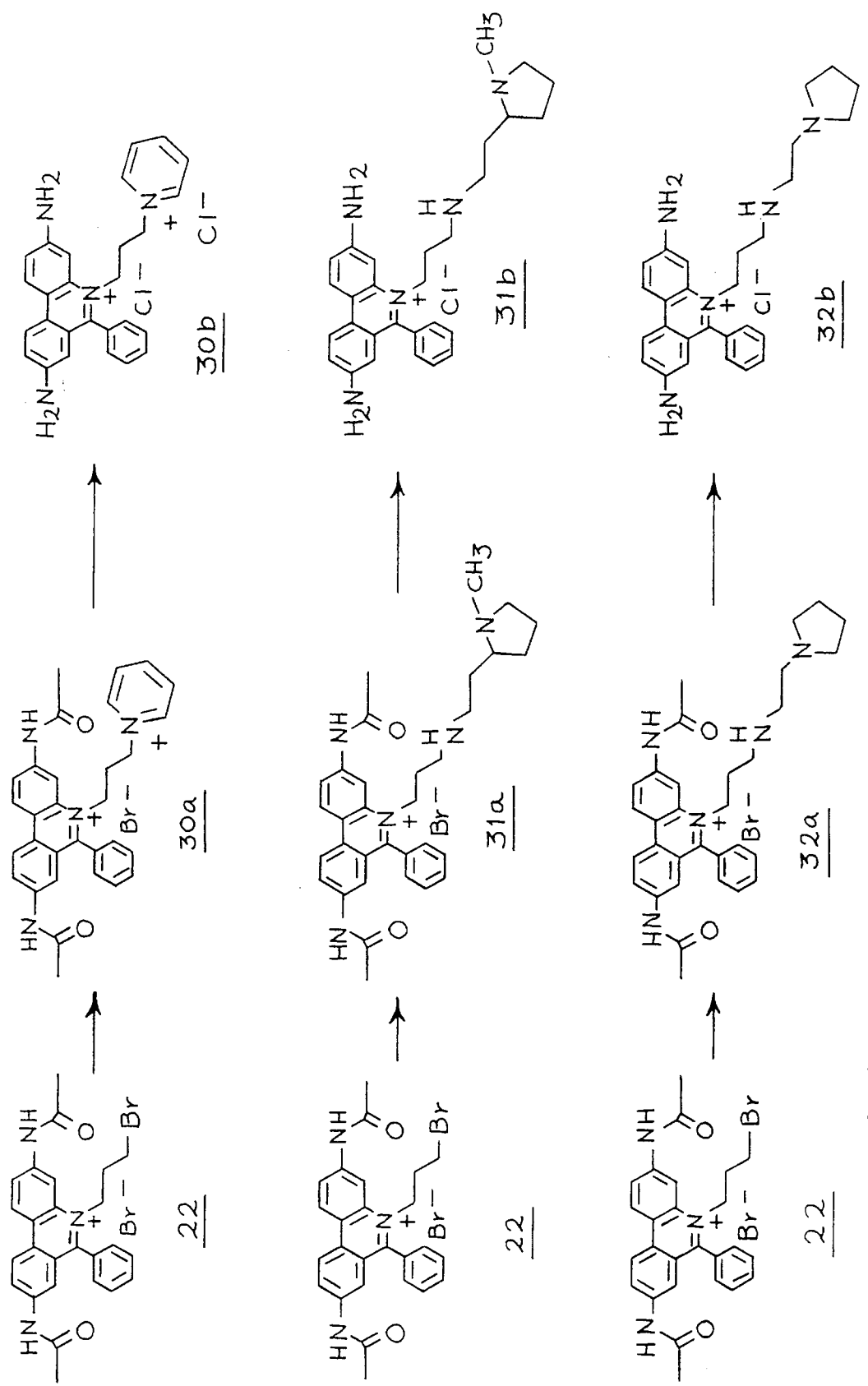
Fig. 17A(2)

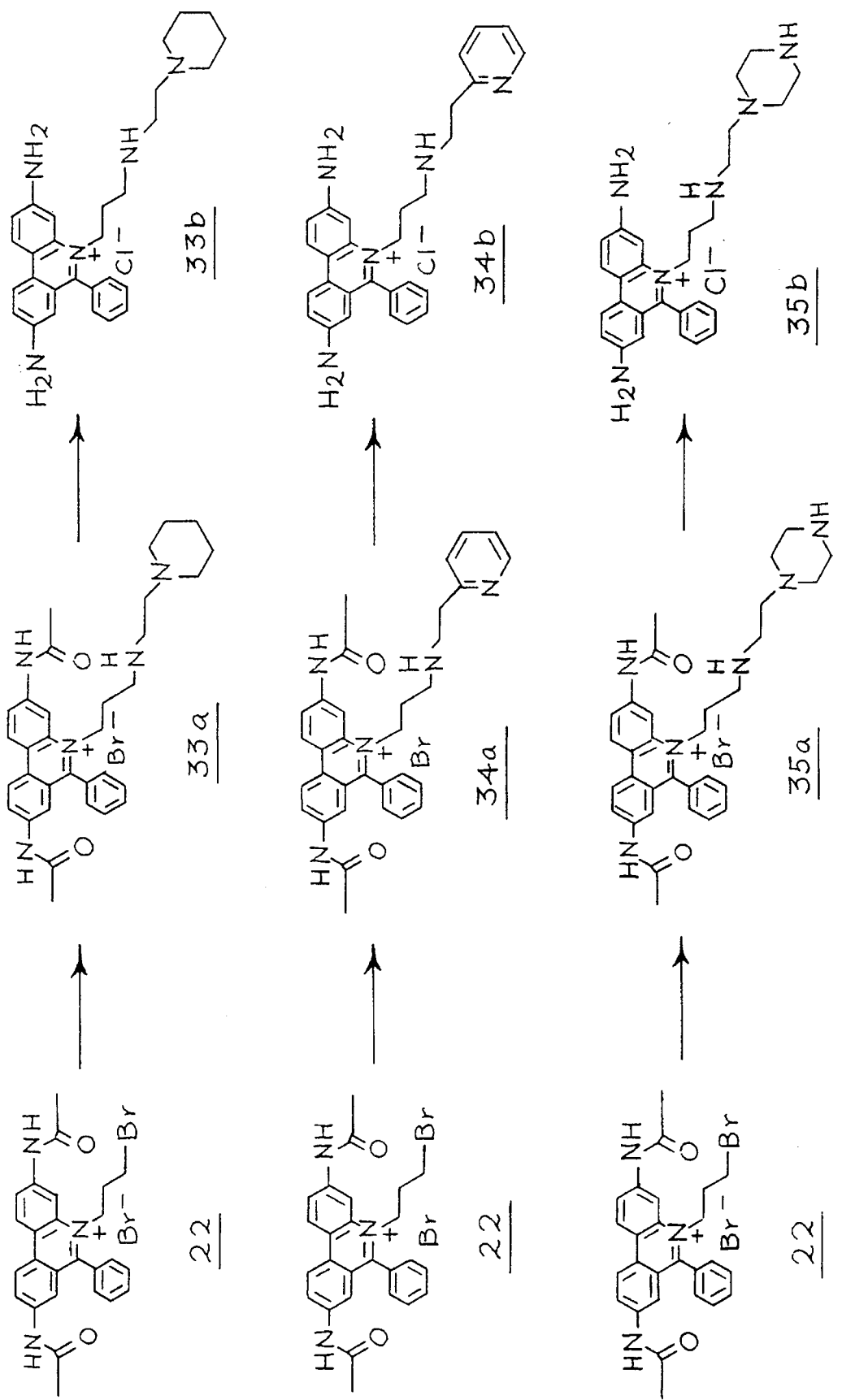
Fig. 17B(1)

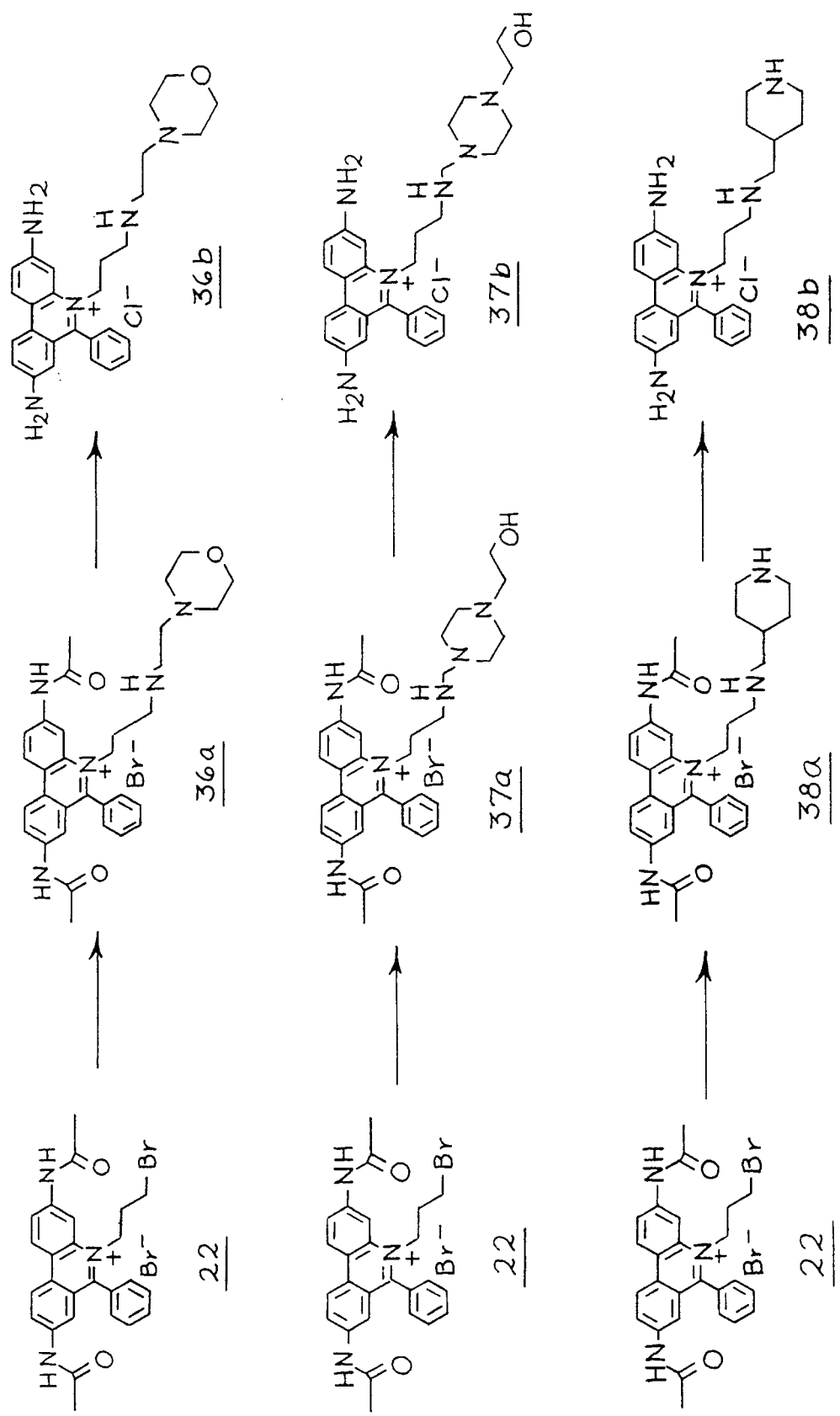
Fig. 17B (2)

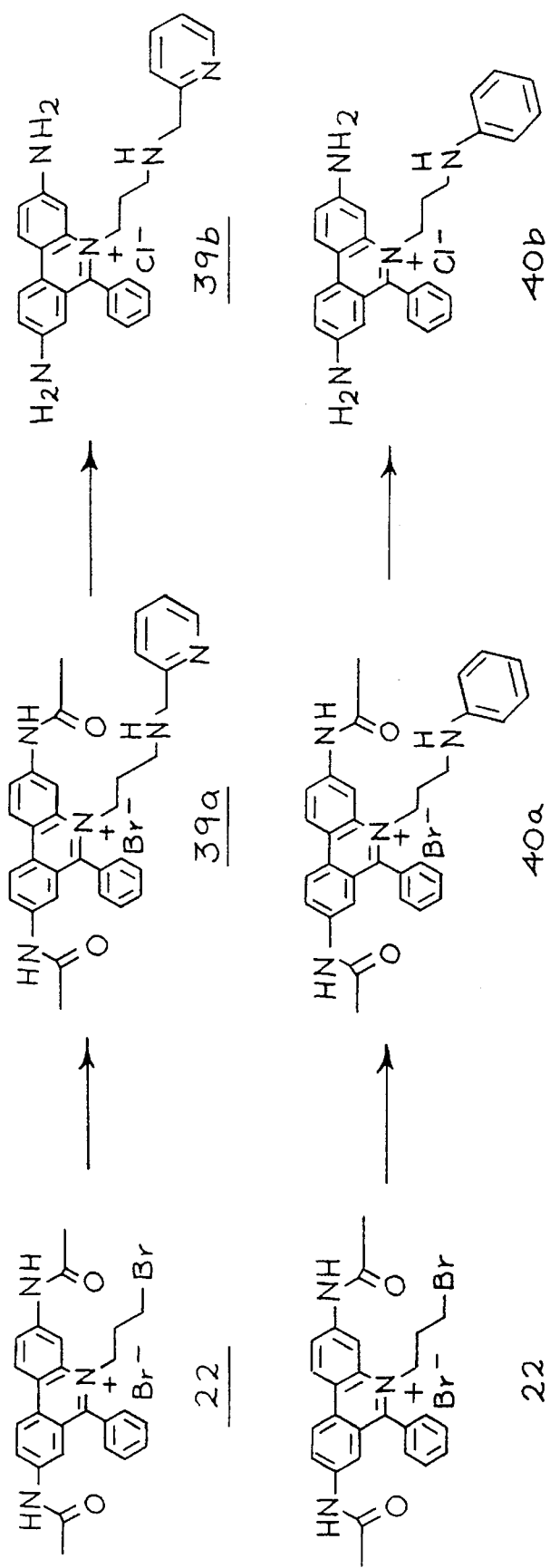
Fig. 17c(1)

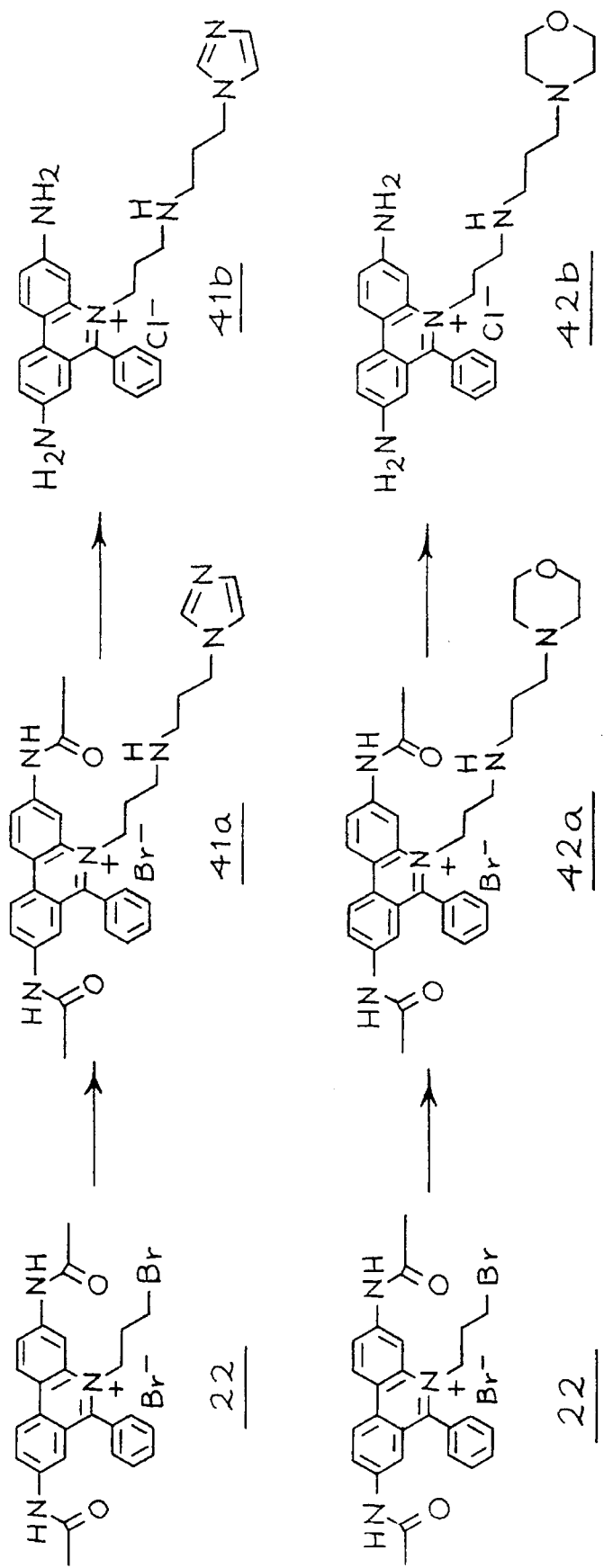
Fig. 17c (2)

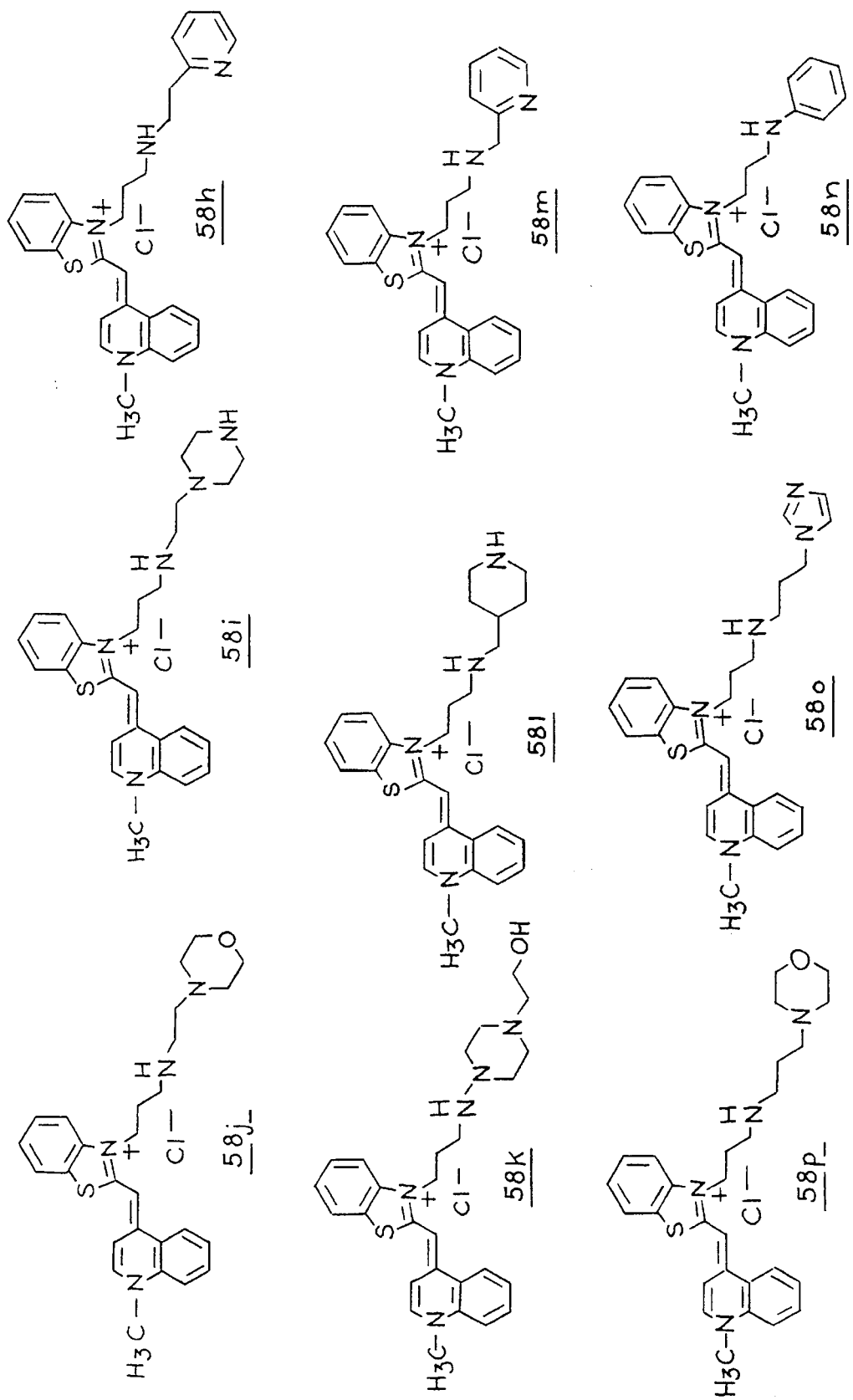
Fig. 22 (2)

INTERCALATORS HAVING AFFINITY FOR DNA AND METHODS OF USE

This is a division of U.S. patent application Ser. No. 08/265,342 filed Jun. 23, 1994, which is a continuation-in-part of application Ser. No. 08/086,285 filed Jun. 30, 1993 now abandoned, the entire content of which is hereby incorporated by reference.

The present invention relates to intercalator compounds, and the use of such compounds, each of which is comprised of an intercalator moiety, or a substituted intercalator moiety, derivatized with one or more functionalized chains, or moieties, and which compounds have high affinity for binding to a DNA molecule. These intercalator compounds exhibit improved binding to a DNA molecule within known methodologies requiring intercalator insertion into the DNA molecule. Still, the invention relates to enhanced binding of DNA molecules by an intercalator-functioning segment utilized in labeling, capture, therapeutic insertion, assay and the like, with improved performance of the intercalator due to the increased utilization efficiency of the compounds.

The term "intercalator" was introduced into the chemistry field over 30 years ago to describe the insertion of planar aromatic or heteroaromatic compounds between adjacent base pairs of double stranded DNA (dsDNA). Many DNA intercalating compounds elicit biologically interesting properties. It is generally agreed that these properties are related to their reactivity with DNA. In the search for more active compounds, it is logical to design molecules with the highest possible affinity for DNA. In 1990, it was reported that complexes of ethidium homodirect with dsDNA performed at ratios of one dimer per four to five base pairs, and were stable to electrophoresis on agarose gels. This allowed fluorescence, detection and quantitation of DNA fragments with picogram sensitivity after separation and complete absence of background stain. Such a result has been sought through various manipulations of intercalator compounds, for example, by functional compounds made up of DNA intercalating dyes. As a result of these efforts, DNA intercalating agents utilizing ethidium bromide have been used in various DNA analytical procedures.

Various reported DNA intercalating agents utilizing ethidium bromide have been used in a multitude of DNA analytical procedures, for example:

Christen, et al., "An Ethidium Bromide-Agarose Plate Assay for the Nonradioactive Detection of CDNA Synthesis", *Anal. Biochem.*, 178 (2), May 1, 1989, pp. 269–272, report ethidium bromide was used to determine the success of eDNA synthesis reactions. Since ethidium bromide in agarose can be used to quantitate RNA and DNA, conditions under which the greater fluorescence of double-stranded DNA is utilized were devised to assay double stranded DNA synthesis from mRNA. Ethidium bromide at 5 micrograms/ml in agarose allowed quantitative detection of eDNA in the range of 0.03 to 0.0015 microgram. Sodium dodecyl sulfate had an adverse effect on the measurement of eDNA. Subsequent cDNA analysis by alkaline gel electrophoresis and staining in 5 micrograms/ml ethidium bromide allowed accurate and rapid sizing of eDNA and required only 0.01–0.05 microgram cDNA.

Petersen, S. E., "Accuracy and Reliability of Flow Cytometry DNA Analysis Using a Simple, One-Step Ethidium Bromide Staining Protocol", *Cytometry*, 7 (4), July, 1986, pp. 301–306, reports that sources of variation and error were investigated for a simple flow cytometric analysis of DNA content of detergent-isolated nuclei stained with ethidium bromide.

In "Ethidium Bromide in the Detection of Antibodies to DNA and of Circulating DNA by Two-Stage Counterimmunoelectrophoresis", *J. Immunol. Methods*, 85 (1), Dec. 17, 1985, pp. 217–220, Riboldi, et al., report that in an attempt to overcome the limitations of counterimmunoelectrophoresis in the detection of precipitating anti-DNA antibodies or circulating DNA, ethidium bromide was used to increase the visibility of the precipitating lines and to confirm their specificity.

W. A. Denny reported in "DNA-Intercalating Ligands as Anti-Cancer Drugs: Prospects for Future Design", *Anticancer Drug Des.*, 4 (4), Dec., 1989, pp. 241–263, that interest in DNA-intercalating ligands as anti-cancer drugs has developed greatly since the clinical success of doxsorubicin.

A number of agents have been described for labeling nucleic acids, whether probe or target, for facilitating detection of target nucleic acid. Suitable labels may provide signals detectable by fluorescence, radioactivity, colorimetry, X-ray diffraction or absorption, magnetism or enzymatic activity, and include, for example, fluorophores, chromophores, radioactive isotopes, enzymes, and ligands having specific binding partners.

Fluorescent dyes are suitable for detecting nucleic acids. For example, ethidium bromide is an intercalating agent that displays increased fluorescence when bound to double stranded DNA rather than when in free solution. Ethidium bromide can be used to detect both single and double stranded nucleic acids, although the affinity of ethidium bromide for single stranded nucleic acid is relatively low. Ethidium bromide is routinely used to detect nucleic acids following gel electrophoresis. Following size fractionation on an approximate gel matrix, for example, agarose or acrylamide, the gel is soaked in a dilute solution of ethidium bromide.

The use of fluorescence labeled polynucleotide probes and polynucleotide hybridization assays have been reported. According to these methods, probes are prepared by attaching a particular absorber-emitter moieties to the three prime and five prime ends of the nucleic acid fragments. The fragments are capable of hybridizing to adjacent positions of a target DNA so that if both fragments are hybridized, the proximity of the absorber and emitter moieties results in the detectable emitter fluorescence. According to these methods, the fluorescent dye is introduced into the target DNA after all in vitro nucleic acid polymerizations have been completed. The inhibitory effects of intercalating agents on nucleic acid polymerases have been described in numerous locations.

DNA binding dyes are useful as antibiotics because of the inhibitory effects of nucleic acid replication processes that result from the agent binding to the template. The use of intercalating agents for blocking infectivity of influenza or herpes viruses have been reported. It has also been reported and described that a number of DNA binding agents, both interealators and nonintercalators, inhibit nucleic acid replication. For example, ethidium bromide inhibits DNA replication.

Methods have been provided for detecting a target nucleic acid in a sample. These methods comprise the steps of (a) providing an amplified reaction mixture that comprises a sample, a DNA binding agent, where said agent is characterized by providing a detectable signal when bound to double stranded nucleic acid, which signal is distinguishable from the signal provided by said agent when it is unbound, and reagents for amplification; (b) determining the amount of signal produced by the mixture of step (a); (c) treating said mixture under conditions for amplifying the target nucleic acid; (d) determining the amount of said signal produced by the mixture of step (c) ; and (e) determining if amplification has occurred. These DNA binding intercalating agents, such as ethidium bromide or ethidium homodimer allow fluorometric study of the interaction of various molecules with DNA.

The intercalating agent useful for DNA binding or detecting amplified nucleic acids is an agent or moiety capable of insertion between stacked base pairs in the nucleic acid double helix. Intercalating agents such as ethidium homodimer and ethidium bromide fluoresce more intensely when intercalated into double stranded DNA than when bound to single stranded DNA, RNA, or in solution. Other uses of intercalators have been in the field of separation and isolation or purification of nucleic acids from complex biological or clinical specimens.

Various methods of separating deoxyribonucleic acids (DNA) from liquid biological samples are known in the art, but are very time consuming or otherwise plagued by complication. It is known that DNA adheres to nitrocellulose. The liquid sample containing DNA is applied to a nitrocellulose filter and the DNA adheres or binds to the filter.

Another method of separating DNA from samples is ultracentrifugation with sucrose or cesium chloride density gradients. The DNA is separated from other macromolecules such as proteins by this method according to the buoyant density or sedimentation coefficient. The biological sample is layered onto the density gradient in a centrifuge tube and is spun at very high speeds for long periods of time for DNA to travel through the density gradient. This method, although satisfactory, is very time consuming and labor intensive. The centrifugation time may be 20 hours or more per sample. Furthermore, if the sample is spun too long, the DNA will not only separate from the sample but also will pass entirely through the gradient to the very bottom of the centrifuge tube along with other constituents in the sample. Therefore, this method is also not suitable as a fast and easy method for separating DNA from complex samples.

Agarose polyacrylamide gel electrophoresis is also used to separate DNA from biological samples. In this method, the sample is applied to one end of a glass or plastic receptacle containing the gel and an electric current is applied across the length of the receptacle. The negatively charged nucleic acid molecules move toward the anode, the larger molecules moving more slowly. The rates of migration of the molecules depend on their molecular weights and on the concentration and degree of cross linking in the gel material. The DNA is then removed from the gel by curing out that portion of the gel in which the DNA is located and finally extracting the DNA. Again, this method is time consuming and labor intensive, and the DNA must still be separated from the gel. When DNA is separated by the electrophoresis gel method or by centrifugation, it is necessary for the DNA to be stained in some manner to be visualized. Typically, ethidium bromide (EtBr) has been used as the staining agent. Ethidium bromide adheres to the DNA by intercalation between the base pairs of the double helix structure of the DNA.

More recently, an ethidium homodimer has been synthesized and introduced with bifunctional intercalators in order to allow fluorometric study including the interaction of such molecules with DNA. It has been determined that the ethidium homodimer ("EthD") binds to double stranded DNA ("dsDNA") about two (2) orders of magnitude more strongly than ethidium bromide. Complexes of EthD with dsDNA have performed at a ratio of one dimer per 4 to 5 base pairs and were found to be stable to electrophoresis on agarose base. On binding to dsDNA, the fluorescence quantum yield of the dimer increases 40 fold independent of nucleotide sequence.

Stable dsDNA-fluoropore complexes can be formed to obtain anywhere from several to several thousand fluoropores each, as desired. Under suitable controlled conditions these complexes do not transfer dye to other nucleic acids or proteins. An important property of these complexes is that their fluorescence emission intensity is a linear function of the number of intercalated dye molecules. As high sensitivity fluorescence detection apparatus becomes more generally available, the ability to use dyes to replace, for example, radioactivity for sensitivity detection of DNA, is becoming more and more valuable.

Dye dsDNA complexes represent a novel family of fluorescence labels with a wide range of spectroscopic properties whose composition, structure and size can be tailored to particular applications. DNA molecules can be readily derivatized to attach biotin, digoxigenin or any number of other substituents that can be recognized by avidin or antibodies. Such derivatized DNA molecules loaded with dye may allow detection at much higher sensitivity in numerous applications, for example, immunoassay, fluorescence, and in situ hybridization of chromosomes and the like that currently use other fluorescence labels.

Probes with a double stranded region, which provide intercalation sites and a single stranded region to allow recognition by hybridization of specific target sequences, offer another approach to the generation of versatile fluorescent labels. Development of conditions that allow clear discrimination between the binding of intercalators to single and double stranded nucleic acids is an essential prerequisite to the use of such probes.

Fluorescent probes are valuable reagents for the analysis and separation of molecules and cells. Some specific examples of their application are identification and separation from a subpopulation of cells in a mixture of cells by the techniques of fluorescence, flow cytometry, fluorescence-activated cell sorting, and fluorescence microscopy. Other applications include determination of a concentration of a substance or member of a specific binding pair that binds to a second species, or member of the specific binding pair, e.g., antigen-antibody reactions in an immunofluorescent assay. Still another application is the localization of substance in gels and other insoluble supports by the techniques of fluorescence staining.

Choice of fluorescers for these purposes is hampered by various constraints; one being the absorption and emission characteristics of the fluorescer since many ligands, receptors and other binding pair members, as well as other extraneous materials associated with the sample, for example, blood, urine and cerebrospinal fluid, will autofluoresce and interfere with an accurate determination or quantification of the fluorescent signal generated by the fluorescent label when the sample is exposed to the appropriate stimulus. Another consideration is the quantum efficiency of the fluorescer. Yet another concern is self-quenching; this can occur when the fluorescent molecules interact with each other when in close proximity. An additional concern is the non-specific binding of the fluorescer to other compounds or even with the test container.

It has been shown that dsDNA forms highly fluorescent complexes with the bis-intercalator EthD. Observations regarding the bis-intercalator EthD suggest that the intercalator can be exploited to generate a family of highly fluorescent stable dsDNA-dye complexes with distinctive properties. Such complexes could be exploited by multiplex detection of dsDNA fragments, as well as many analytical applications in which appropriately diversified dsDNA fragments labeled noncovalently with different dyes could be used as a unique family of fluorescent probes:

being used. Once excited, fluorescence emission occurs typically at wavelengths different from the wavelength of excitation. Fluorescence analysis instruments, whether fluorescence microscopes, image analyzers or flow cytometers, are generally designed to detect the fluorescence emission at the wavelength of emission maxima where the fluorescence signal is strongest.

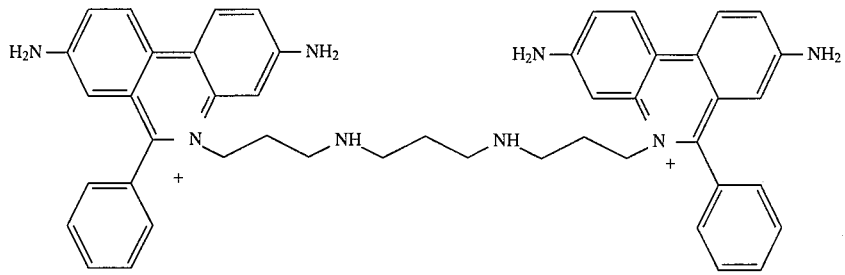

However, this compound may have a tendency to self-quench when bound to DNA.

In flow cytometry apparatuses, cells or other particles are caused to flow in a liquid flow stream so as to facilitate the investigation of certain characteristics thereof. In general, a flow cytometry apparatus is useful for identifying the presence of certain cells or particles of interest, enumerating those cells or particles and, in some instances, providing a sorting capability so as to be able to collect those cells or particles of interest. In a typical flow cytometry apparatus, a fluid sample containing cells is directed through the apparatus in a rapidly moving liquid stream so that each cell passes serially, and substantially one at a time, through a sensing region. Cell volume may be determined by changes in electrical impedance as each cell passes through the sensing region. Similarly, if an incident beam of light is directed at the sensing region, the passing cells scatter such light as they pass therethrough. This scattered light has served as a function of cell shape and size, index of refraction, opacity, granularity, roughness and the like. Further, fluorescence emitted by labeled cells, or autofluorescent cells, which have been excited as a result of passing through the excitation energy of the incident light beam is detectable for identification of cells having fluorescent properties. After cell analysis is performed by the flow cytometry apparatus, those cells that have been identified as having the desired properties may be sorted if the apparatus has been designed with such capability.

Instruments such as flow cytometry apparatuses are particularly useful for researchers and investigators studying various responses, reactions and functions of the immune system. Immunofluorescence studies, as well as fluorescence immunoassays, assist the investigator in identifying and targeting select cells of interest so that disease states, conditions and the like may be properly characterized. In addition to immune system investigations, fluorescence analysis is also quite beneficial in cell biology and morphology investigations, including the study of the substrate of cellular material.

In relying upon fluorescence to provide data and information about cells, the mechanics of performing tests for the fluorescence response is a major consideration in the design of the instrument as well as the results obtained. Specifically, the fluorescent markers, whether such markers be fluorescent stains or dyes, are typically excited by light energy. Usually there is an optimal wavelength which provides the greatest level of excitation for the fluorochromatic marker Before the discovery and publication of the utilities of ethidium homodimer as an important intercalator, the usual intercalator of choice was ethidium bromide. Uses of the ethidium bromide intercalators include fluorometric methodologies, quantitative fluorescences of DNA intercalated ethidium bromide on agarose gels, ethidium bromide-agarose plate assay or detection of false DNA analysis and the like. Ethidium bromide and propidium bromide were further used in flow cytometry, as well as applications for direct electronic imaging, direct and rapid quantitation of fluorescence and electrophoretic gels in application as ethidium bromide-stain DNA. Ethidium bromide has also been used to increase the visibility of the precipitant lines and to confirm the specificity in two stage counter immunoelectrophoresis methodologies for detection of participating anti-DNA antibodies or circulating DNA. Utilization of ethidium bromide as an intercalator in numerous environments, as well as the more recent utilization of the ethidium homodimer interealator are well documented in the literature and present the leading edge of intercalator methodology and efficiency.

In a somewhat different application of ethidium bromide as a staining agent, ethidium bromide has been linked to a solid support. U.S. Pat. No. 4,119,521, issued to Chirikjian on Oct. 10, 1978, discloses a fluorescent DNA intercalating agent derivative of activated polysaccharides. The derivatives in the patent function as fluorescent stains to provide direct visualization of the DNA and their fractions, under the excitation of shortwave, ultraviolet radiation. The intercalating agents used in the patent are ethidium halides, with the preferred agent being ethidium bromide. This agent is coupled covalently to an activated polysaccharide such as agarose.

Utilization of ethidium bromide as an intercalator for use in numerous environments, as well as the more recent utilization of the ethidium homodimer intercalator are well documented in the literature and present the leading edge of intercalator methodology and efficiency. However, there remains an ever present need to improve utilization of the intercalators and viability of the use of intercalators with DNA, specifically addressing (1) high affinity for binding the intercalators to the DNA molecule; (2) reduction of self-quenching; and (3) providing superior transport kinetics. Intercalators possessing these qualities reduce the amount of intercalator required for performing one of the many functions involved in the aforementioned methodologies which can also enhance methodologies. In addition, improvement in accuracy and reliability of the various uses of interest is of continuing concern.

SUMMARY

Broadly, the invention provides a compound having an "I" moiety bonded to one or more "T" moiety. The general formula of the compounds are represented by:

I-(T)$_m$ wherein the I moiety denotes an aromatic or heteroaromatic segment; the T moiety denotes a "tail" or "chain" moiety; and m is an integer from 1 to 5. When m is more than 1, T can be similar or different from one another.

In one aspect, the present invention provides a compound having an I moiety bonded to one or more T moiety, the T moieties, when more than one T moiety are present, are the same or different from one another, the T moiety having the formula of:

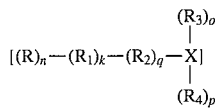

and the compound having a formula:

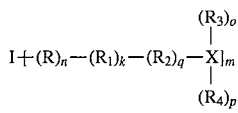

wherein: I is an aromatic or heteroaromatic segment;

X is a heteroatom selected from the group consisting of nitrogen
and sulfur;

R, R$_1$ and R$_2$ are the same or different from one another and are alkyl, alicyclic, heteroalicyclic, aromatic or heteroaromatic groups;

R$_3$ and R$_4$ are hydrogen when X is nitrogen; R$_3$ and R$_4$ are methyl, ethyl, or phenyl groups when X is sulfur;

k is zero or an integer from 1 to 10;

q is zero or an integer from 1 to 10;

n is an integer from 20 to 20;

m is an integer from 1 to 5;

o is zero or one; and p is zero or one;

and the acid addition salts thereof;

provided that the I moiety is not phenantruidium when: X is nitrogen; R$_3$ and R$_4$ are hydrogens R, R$_1$ and R$_2$ are methylene groups; o is 1; p is 1; m is 1; and the acid addition salts thereof;

provided that the I moiety is not phenantruidium when: X is nitrogen; R$_3$ and R$_4$ are hydrogens; R, R$_1$ and R$_2$ are methylene groups; o is 1; p is 1; m is 2; a first T moiety directly bonded to the I moiety in which n is 2, k is 1 and q is zero; a second T moiety, directly bonded to the first T moiety, in which n is 2. and k and q are zero; and acid addition salts thereof;

provided that the I moiety is not phenantruidium when: X is nitrogen; R$_3$ and R$_4$ are hydrogens; R, R$_1$ and R$_2$ are methylene groups; o is 1; p is 1; m is 2; a first T moiety directly bonded to said I moiety in which n is 2, k is 1 and q is zero; a second T moiety, directly bonded to the first T moiety, in which n is 2, k is 1 and q is 1 and acid addition salts thereof; and provided that the I moiety is not phenantruidium when: X is nitrogen; R$_3$ and R$_4$ are hydrogen; o is 1; p is 1; m is 3; n is 2; k is 1; q is zero; and acid addition salts thereof.

The invention provides compounds comprised of intercalator moieties or substituted intercalator moieties having a functionalized chain, which compounds provide a high affinity for binding to the DNA molecule and show reduced self-quenching while providing superior transport kinetics. The inventive intercalators have been found to provide enhanced fluorescence when bound to a DNA molecule within a fluorescent flow cytometry environment which is about eight to ten times brighter in fluorescence than ethidium homodimer utilized in the same flow cytometry environment. Because of the enhancement of fluorescence, the detection of DNA hybridization can be accomplished using much lower concentrations of intercalator compounds of the present invention than using conventional intercalating agents, such as ethidium homodimer or ethidium bromide. Using the same concentrations, intercalator compounds of the present invention can detect far less amounts of DNA hybridization than can conventional intercalating agents. Thus, the intercalator compounds of the present invention are far more sensitive than the known intercalating agents in detecting DNA hybridization.

Improvements in flow cytometry, fluorescence in-situ hybridization assays, gel electrophoresis, DNA detection, immunoassay for DNA, and other DNA studies are substantial. The use of intercalators with DNA and multiple methods have shown that the ethidium homodimer is about two orders of magnitude brighter than conventional staining methodology, i.e., ethidium bromide. However, the intercalator compounds in accordance with the present invention provide, for example, a dye which exhibits an eight to ten-fold increase in brightness over that of EthD in the same environment, or about a thousandfold improvement over more conventional staining methodologies. With pre-staining and post-electrophoresis detection, the sensitivity level of radioimmunoassay detection of DNA is now attainable with fluorophores. The compound compositions provided by this invention extends the limits of detection by up to tenfold over EthD, thereby providing a potential for new uses in applications of intercalators for the study of DNA analysis, as well as therapeutics and the like.

BRIEF DESCRIPTION OF THE FIGURES

FIG. 13 shows the structures of representative I moieties;

FIG. 16 shows the structural formula of compounds 25, 26 and 27;

FIG. 17 is a reaction scheme for the synthesis of compounds 28a–42a;

DETAILED DESCRIPTION

Figure 1:
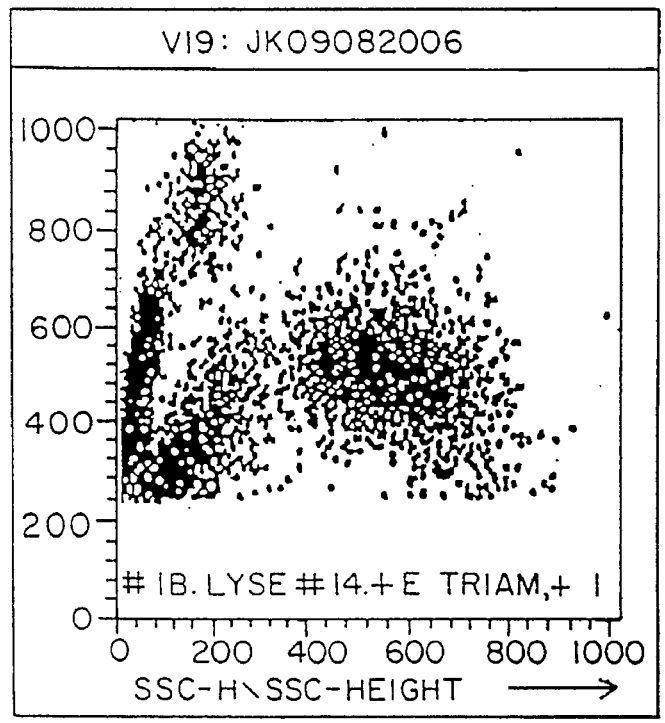
FIG. 1 is a FACScan™ display for side scatter versus forward scatter.

Broadly, the present invention provides an intercalator having an I moiety bonded to one or more T moiety. The general formula of the compounds are represented by:

$$I\text{-}(T)_m$$

wherein the I moiety denotes an aromatic or heteroaromatic segment; the T moiety denotes a "tail" or "chain" moiety; and m is an integer from 1 to 5, preferably from 1 to 3.

When the I moiety contains a mono-quaternary ammonium functionality, it is accompanied by a monovalent counter anion ("A"). Examples of monovalent counter anion include chloride, bromide, iodide, hydroxide, and hydrogen phosphate.

Improved binding to the DNA molecule of intercalators and substituted intercalators is achieved which exhibit high affinity for binding, reduced self-quenching, and superior transport kinetics, especially when compared to ethidium homodimer or other bis-intercalators, by providing intercalator segments with functionalized chains forming compounds having the formula:

$$I + (R)_n - (R_1)_k - (R_2)_q - \overset{(R_3)_o}{\underset{(R_4)_p}{X}} -]_m$$

wherein I is an aromatic or heteroaromatic segment; X is a nitrogen or a sulfur; R, $R_1$ and $R_2$ are alkyl, alicyclic, heteroalicyclic, aromatic or heteroaromatic groups; $R_3$ and $R_4$ are hydrogens when X is nitrogen or methyl, ethyl or phenyl groups when X is phosphorus or sulfur; k is zero or an integer from 1 to 10; q is zero or an integer from 1 to 10; m is an integer from 1 to 5; n is an integer from 2 to 20; o is zero or one; and p is zero or one.

A compound comprised of an intercalator functionalized with chains containing heteroatoms and aliphatic, alicyclic, cyclohexyl, aromatic segments or combinations thereof having the formula:

$$I + (R)_n - (R_1)_k - (R_2)_q - \overset{(R_3)_o}{\underset{(R_4)_p}{X}} -]_m$$

wherein I is an intercalator segment; X is a main group element phosphorus or sulfur yielding, respectively polyphosphonium or polysulfonium moieties; R, $R_1$ and $R_2$ are alkyl, alicyclic, heteroalicyclic, aromatic or heteroaromatic groups; $R_3$ and $R_4$ are methyl, ethyl or phenyl groups when X is phosphorus or sulfur; k is zero or an integer from 1 to 10; q is zero or an integer from 1 to 10; m is an integer from 1 to 5; n is an integer from 2 to 20; o is zero or one; and p is zero or one; where X is sulfur, o or p are zero; and where X is phosphorus, o and p are one.

In another embodiment, it is provided a compound having the general structural formula of:

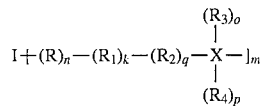

wherein I is an aromatic or heteroaromatic segment; X is a nitrogen or a sulfur; R, $R_1$ and $R_2$ are the same or different and are alkyl of one to four carbons, alicyclic of five to six carbons, heteroalicyclic of three to five carbons and one or two heteroatom of nitrogen, oxygen or sulfur, aromatic group of benzene, phenyl or naphthyl or heteroaromatic group of one to five carbons and one to four heteroatom of nitrogen, oxygen, or sulfur; $R_3$ and $R_4$ are hydrogens when X is nitrogen or methyl, ethyl or phenyl groups when X is sulfur; k is zero or an integer from 1 to 10; q is zero or an integer from 1 to 10; m is an integer from 1 to 5; n is an integer from 2 to 20; o is zero or one; and p is zero or one.

In yet another aspect, there is provided a compound comprised of an intercalator functionalized with chains containing heteroatoms and aliphatic, alicyclic, cyclohexyl, aromatic segments or combinations thereof having the formula:

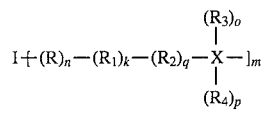

wherein I is an aromatic or heteroaromatic segment;. X is a main group sulfur yielding polysulfonium moieties; R, $R_1$ and $R_2$ are the same or different and are alkyl of one to four carbons, alicyclic of five to six carbons, heteroalicyclic of three to five carbons and one or two heteroatom of nitrogen, oxygen or sulfur, aromatic group of benzene, phenyl or naphthyl or heteroaromatic group of one to five carbons and one to four heteroatom of nitrogen, oxygen, or sulfur; $R_3$ and $R_4$ are hydrogens when X is nitrogen or methyl, ethyl or phenyl groups when X is sulfur; k is zero or an integer from 1 to 10; q is zero or an integer from 1 to 10; m is an integer from 1 to 5; n is an integer from 2 to 20; o is zero; and p is zero.

A compound comprised of aromatic or heteroaromatic segments functionalized with positively charged chains having the formula:

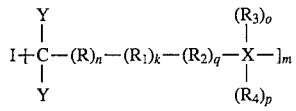

wherein Y is a side chain comprised of positively charged heteroatoms or metal ions in an aliphatic, alicyclic, heteroalicyclic, aromatic or heteroaromatic group or combinations thereof; I is an aromatic or heteroaromatic segment; X is a heteroatom; R, $R_1$ and $R_2$ are alkyl, alicyclic, heteroalicyclic, aromatic or heteroaromatic group; $R_3$ and $R_4$ are hydrogens when X is nitrogen or methyl, ethyl or phenyl groups when X is phosphorus or sulfur; k is zero or an integer from 1 to 10; q is zero or an integer from 1 to 10; m is an integer from 1 to 5; n is an integer from 2 to 20; o is zero or one; p is zero or one; where X is sulfur, o and p are zero; and where X is phosphorus o and p are one.

A compound as above wherein Y has the formula:

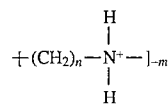

Further, a compound comprised of intercalators functionalized with chains containing metal atoms and alkyl, alicyclic, or aromatic segments or combinations having the formula:

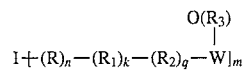

wherein W is aluminum, boron or a Lewis acid metal; I is an intercalator segment; R, $R_1$ $R_2$ and $R_3$ are alkyl, alicyclic, or aromatic groups; k is zero or an integer from 1 to 10; q is zero or an integer from 1 to 10; m is an integer from 1 to 5; and n is an integer from 2 to 20.

An intercalator composition functionalized with positively charged chains where the positive charges are located on an aliphatic, alicyclic, aromatic or the combination thereof with a polyaminic ester group of main chain polyphosphate, polyphosphonate or polysulfate, having the formula:

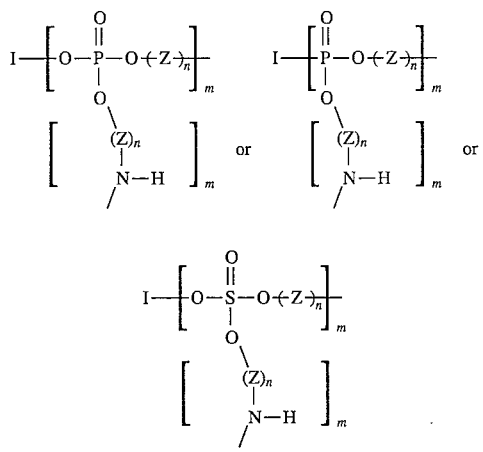

wherein I is an aromatic or heteroaromatic segment; P is a phosphorus atom; S is a sulfur atom; Z is an aliphatic, alicyclic or aromatic chain or the combination thereof; n is from 2 to 20, preferably 2 or 3; and m is from 1 to 5, preferably, 3–10.

Broadly, the present invention relates to a compound comprised of an intercalator moiety, or a substituted intercalator moiety, derivatized with functionalized chains, and the compound has high affinity for binding to a DNA molecule. In one aspect, the invention relates to use of these intercalator compounds which exhibit improved binding to a DNA molecule within known methodologies requiring intercalator insertion into the DNA molecule. Still, the invention relates to enhanced binding of DNA molecules by an intercalator functioning segment utilized in labeling, capture, therapeutic insertion, assay and the like, with improved performance of the intercalator due to the increased utilization efficiency of the compounds. Improved binding to the DNA molecule of intercalators and substituted intercalators is achieved which exhibit high affinity for binding, reduced self-quenching, and superior transport kinetics, especially when compared to ethidium homodimer or other bis-intercalators.

The various embodiments of the present invention inclusive of synthesis of the compounds and utilization of said compounds are shown in FIGS. 1–9, 10A–10F, 11–30. The information shown in these figures clearly demonstrates high affinity for binding, reduced self-quenching, and superior transport kinetics, especially when compared to ethidium homodimer or other bis-intercalators.

FIG. 1 is a FACScan™ display for side scatter versus forward scatter (SSC on abscissa axis and FSC on the ordinate axis) for a typical distribution of white cells lysed with WBC DIL diluent with NRBC dye phenathridinium triamine (PTA) 24 and CEN. The quadrant thresholds were set to preclude the lymphocytes gated on the SSC versus FSC dot plot.

Figure 2:
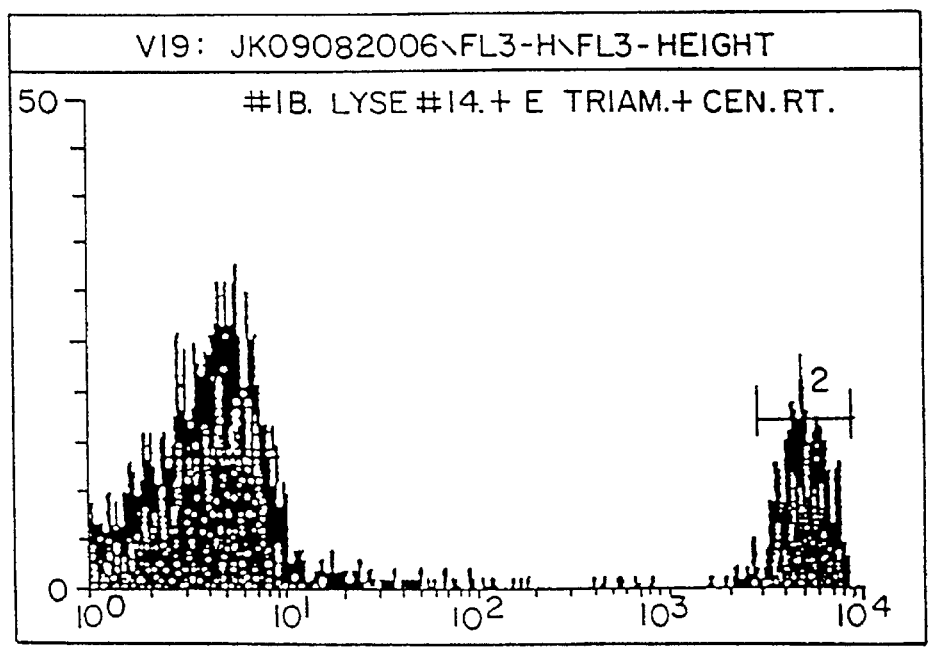
FIG. 2 is a histogram of fluorescence intensity (abscissa) versus frequency of events (ordinate)

FIG. 2 is a histogram of fluorescence intensity (abscissa) versus frequency of events (ordinate) for the populations of stained and unstained cells in the presence of phenathridinium triamine (PTA) 24.

Figure 3:
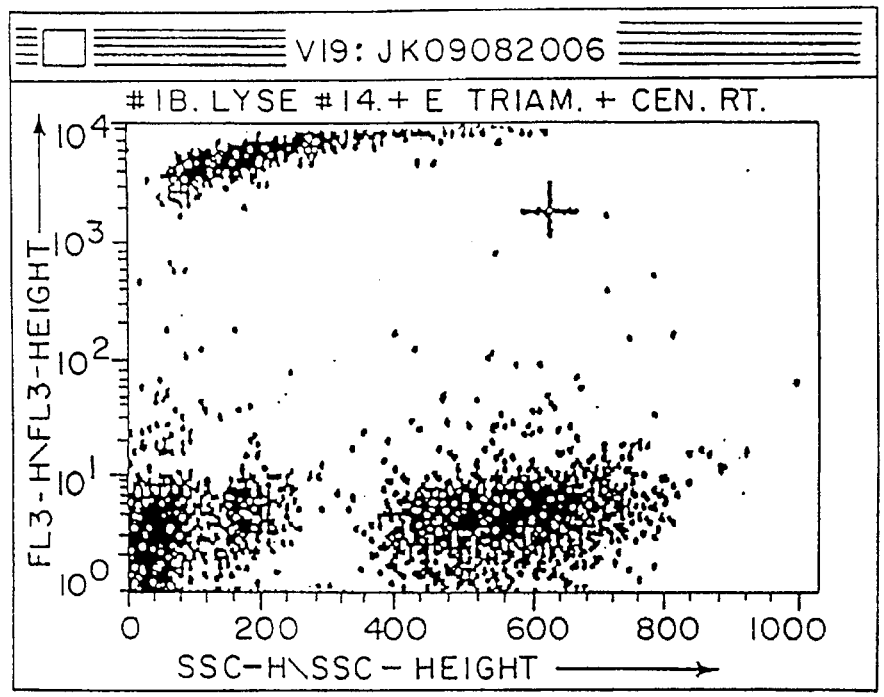
FIG. 3 is a scattergram representation for side scatter (SSC on abscissa) versus fluorescence intensity (ordinate)

FIG. 3 is a scattergram representation for side scatter (SSC on abscissa) versus fluorescence intensity (ordinate) showing the separation of cells stained with PTA 24 (upper left hand corner, NW quadrant) from unstained cells (remainder) by fluorescence intensity.

Figure 4:
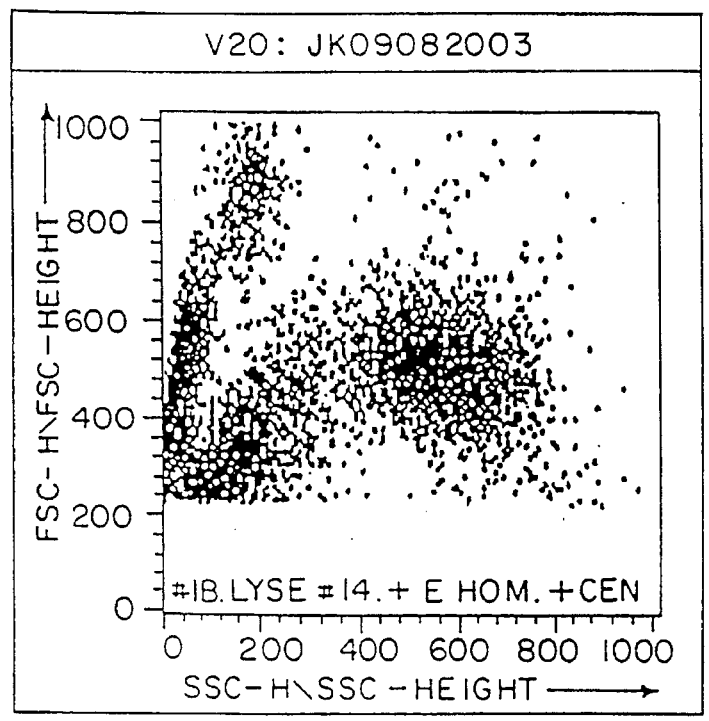
FIG. 4 is a FACScan™ display for side scatter versus forward scatter.

FIG. 4 is a FACScan™ display for side scatter versus forward scatter (SSC on abscissa axis and FSC on the ordinate axis) for a typical distribution of white cells lysed with WBC DIL diluent with NRBC dye ethidium homodimer and CEN. The quadrant thresholds were set to preclude the lymphocytes gated on the SSC versus FSC dot plot.

Figure 5:
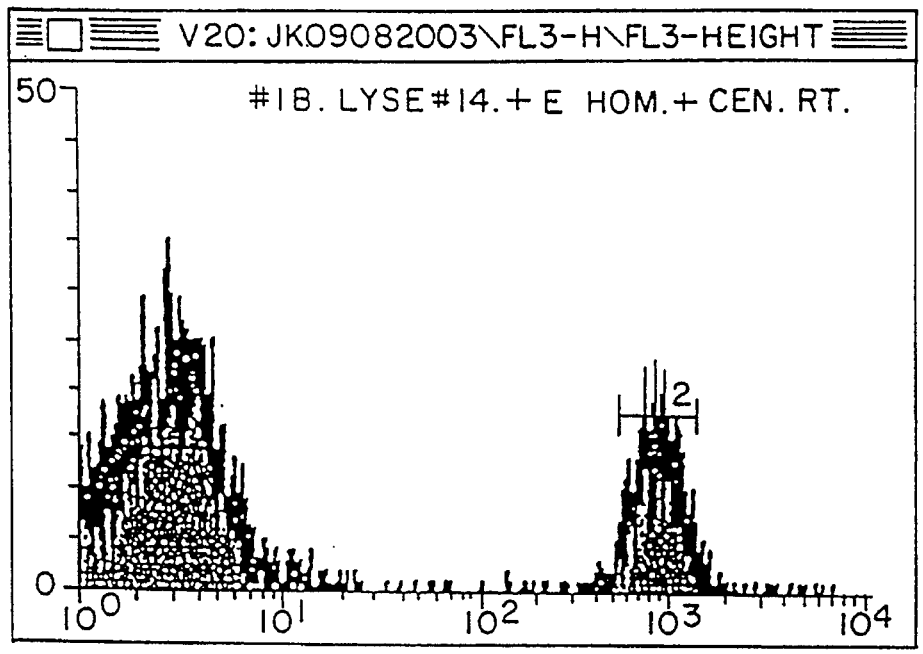
FIG. 5 is a histogram of fluorescence intensity (abscissa) versus frequency of events (ordinate)

FIG. 5 is a histogram of fluorescence intensity (abscissa) versus frequency of events (ordinate) for the populations of stained and unstained cells in the presence of ethidium homodimer.

Figure 6:
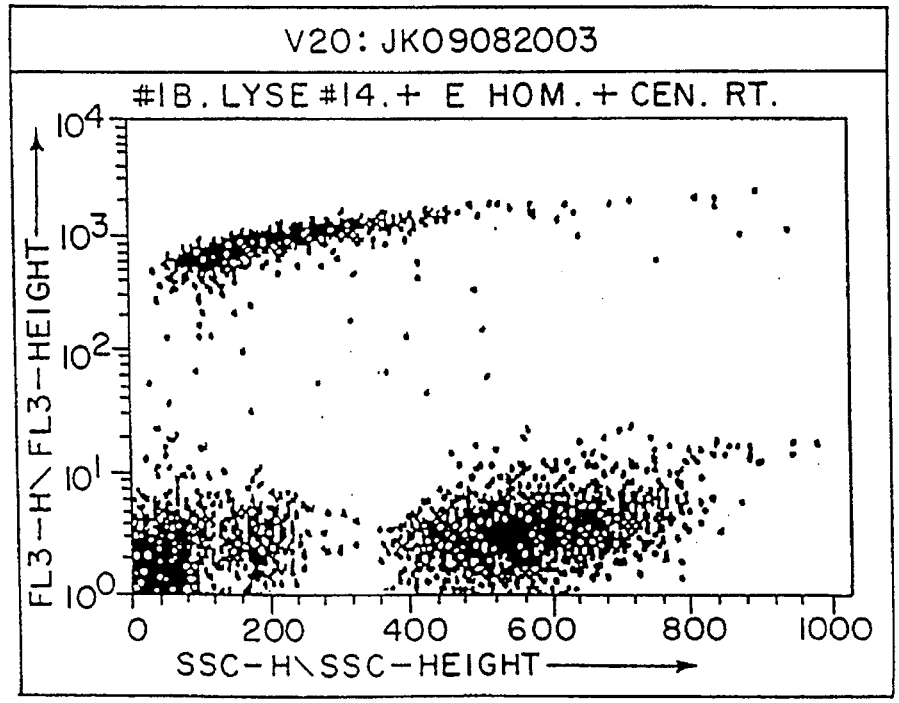
FIG. 6 is a scattergram representation for side scatter (SSC on abscissa) versus fluorescence intensity (ordinate)

FIG. 6 is a scattergram representation for side scatter (SSC on abscissa) versus fluorescence intensity (ordinate) showing the separation of cells stained with ethidium homodimer (upper left hand corner, NW quadrant) from unstained cells (remainder) by fluorescence intensity.

Figure 7:
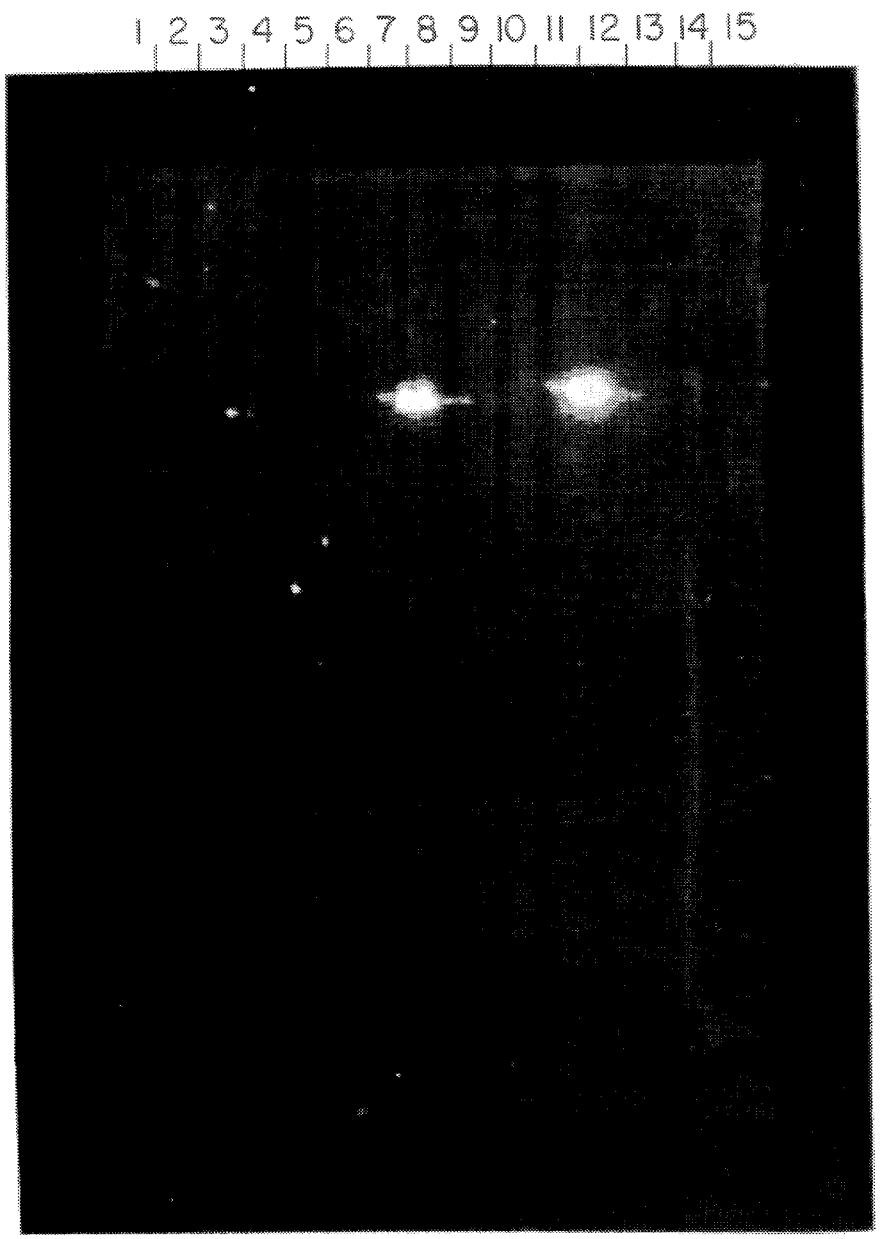
FIG. 7 is a photographic representation of a UV light irradiated agarose electrophoresis gel performed on enzyme BAMH nicked PBR322 plasmid DNA.

FIG. 7 is a photographic representation of a UV light irradiated agarose electrophoresis gel performed on BAMH nicked PBR322 plasmid DNA. Loadings of 5 μl of stock solutions were made for lanes 3–14. The following stock solutions of DNA and intercalator were used to load lanes 1–14. Lane 1: marker; Lane 2: blank; Lane 3: 20 ng/ml plasmid stained with ethidium bromide; Lane 5: 160 pg/ml plasmid stained with ethidium bromide; Lane 6: 40 pg/ml plasmid stained with ethidium bromide; Lane 7: 20 ng/ml plasmid stained with ethidium homodimer; Lane 8: 800 pg/ml plasmid stained with ethidium homoalimet; Lane 9: 160 pg/ml plasmid stained with ethidium homodimer; Lane 10: 40 pg/ml plasmid stained with ethidium homodimer; Lane 11: 20 ng/ml plasmid stained with PTA 24; Lane 12: 800 pg/ml plasmid stained with PTA 24; Lane 13: 160 pg/ml plasmid stained with PTA 24; Lane 14: 40 pg/ml plasmid stained with PTA 24. In all cases, the dye/base pair ratio was 1/20. In all cases, the dye was pre-incubated with the DNA and no post-gel-electrophoresis staining was done.

Figure 8:
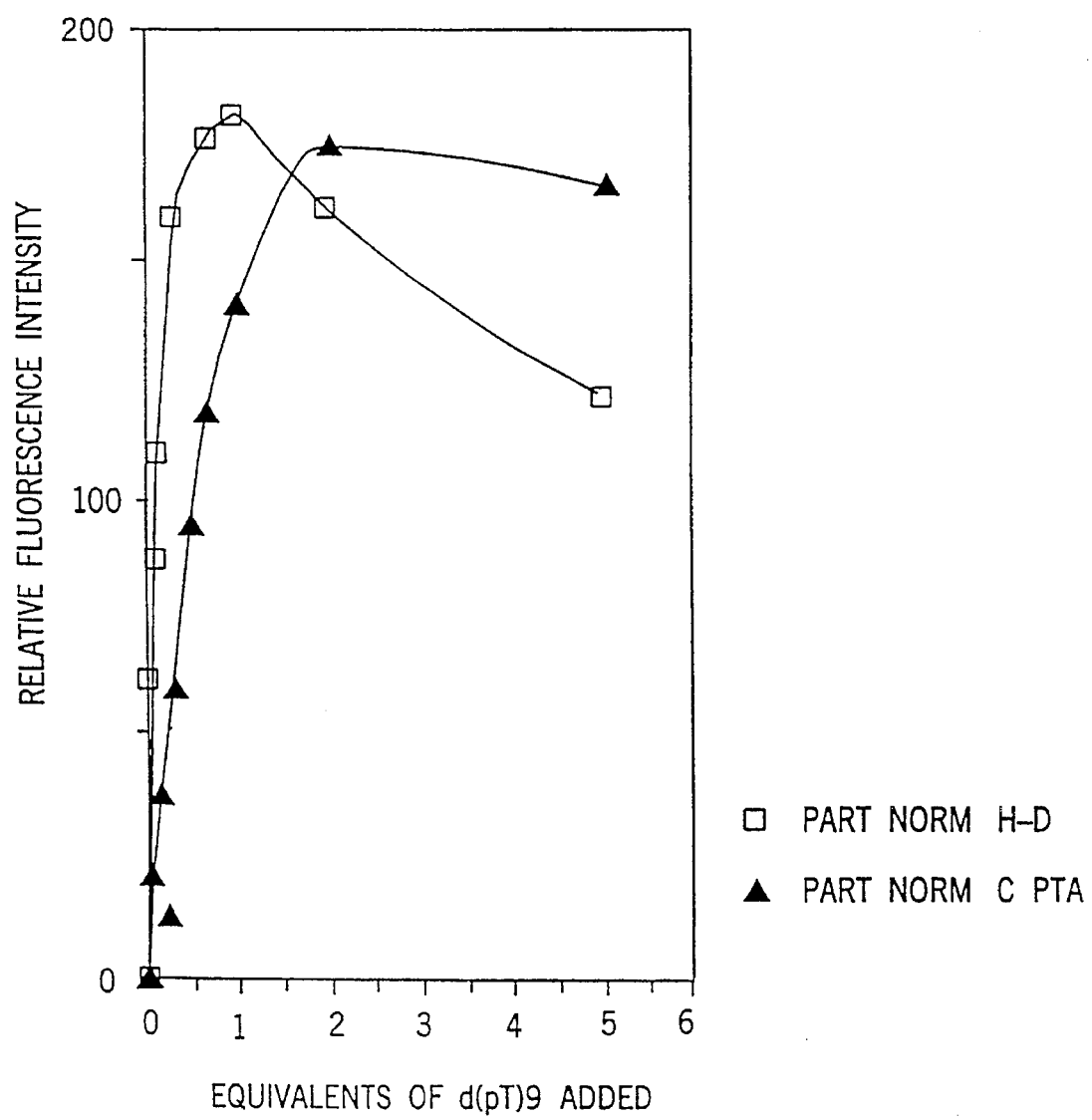
FIG. 8 is a hybridization saturation plot for equivalents.

FIG. 8 is a hybridization saturation plot for equivalents of d(pT)9 added to d(pA)9 at 6.6 micromolar DNA and 3.08 micromolar dye for ethidium homodimer and PTA 24 at a dye base pair ratio of 1:4. Graphical representation of equivalents of complementary oligonucleotide d(pT)9 on the abscissa added to d(pA)9 versus relative fluorescence intensity on the ordinate generated by using the protocol described in Example 2 to compare ethidium homodimer and PTA 24. The concentration of fluorophore in both cases was 3.08 micromolar using a two-fold statistical correction for the 2.0 molar equivalents of phenanthridinium moiety per each mole of ethidium homodimer. Both curves are normalized to background for relative fluorescence. Excitation was at 488 nm (534 nm is the excitation maximum) for this experiment and emission was at 625 nm.

Figure 9:
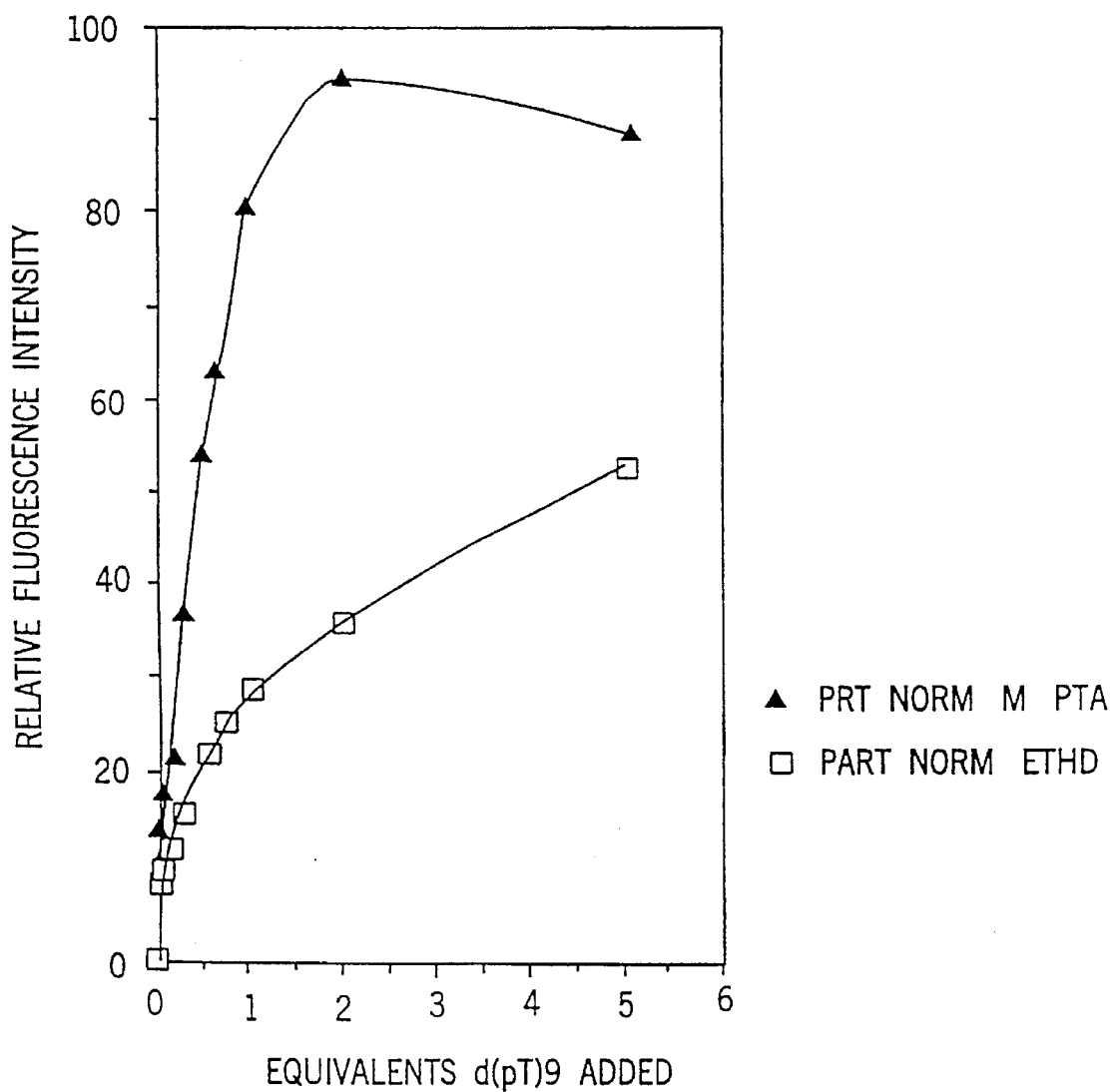
FIG. 9 shows hybridization titration curves for fluorescence intensity versus equivalents.

FIG. 9 shows hybridization titration curves for fluorescence intensity versus equivalents of d(pT)9 added to d(pA)9 at 6.6 micromolar DNA and 3.08 micromolar ethidium bromide and PTA 24. Graphical representation of equivalents of complementary oligonucleotide d(pT)9 abscissa versus relative fluorescence intensity (ordinate) generated by using the protocol described in Example 2 to compare ethidium bromide and PTA 24. The concentration of fluorophore in both cases was 3.08 micromolar. Both curves are normalized to background. Excitation was at 488 nm (534 nm is maximum excitation) and emission was at 625 nm and intensities were measured using a Hitachi F-3010 fluorimeter.

Figure 10A:
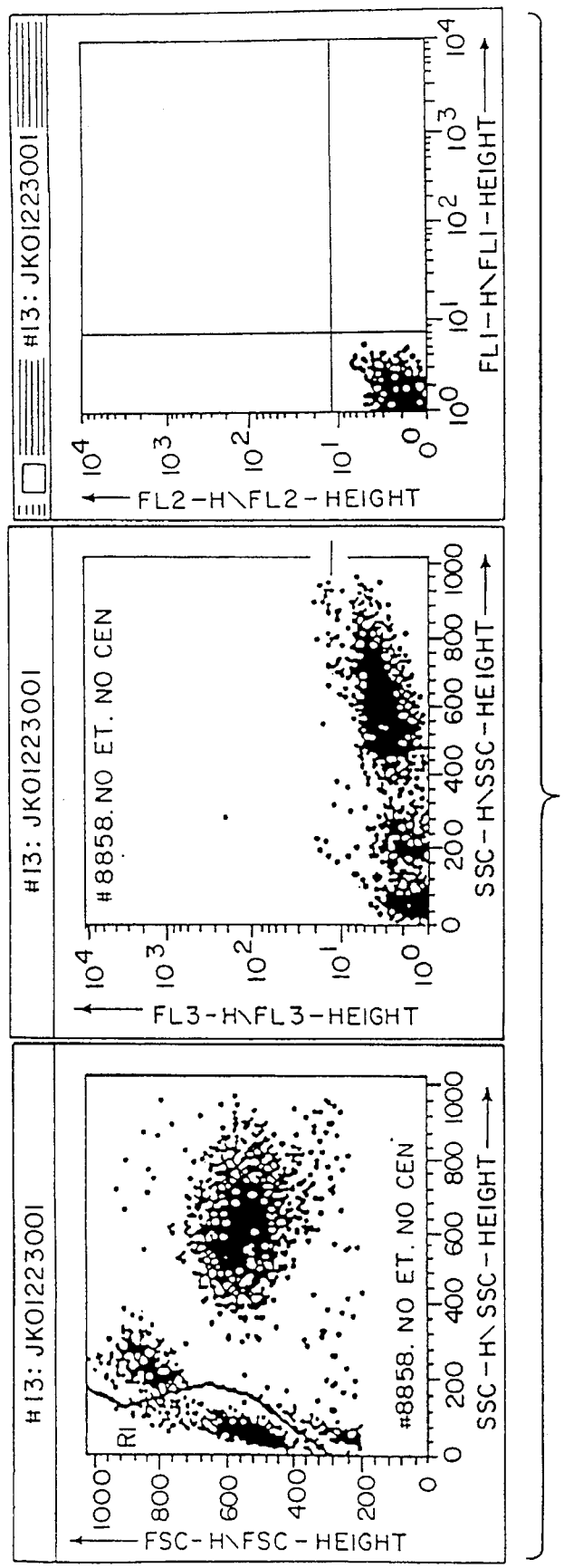
FIG. 10A is a FACScan™ display (SSC vs FSC) of a typical distribution of lysed white cells.

FIG. 10A is a FACScan™ display (SSC vs FSC) of a typical distribution of white cells lysed with CD4000 WBC DIL without NRBC dye or CEN. The quadrant thresholds were set to preclude the lymphocytes gated on the SSC versus FSC dot plot.

Figure 10B:
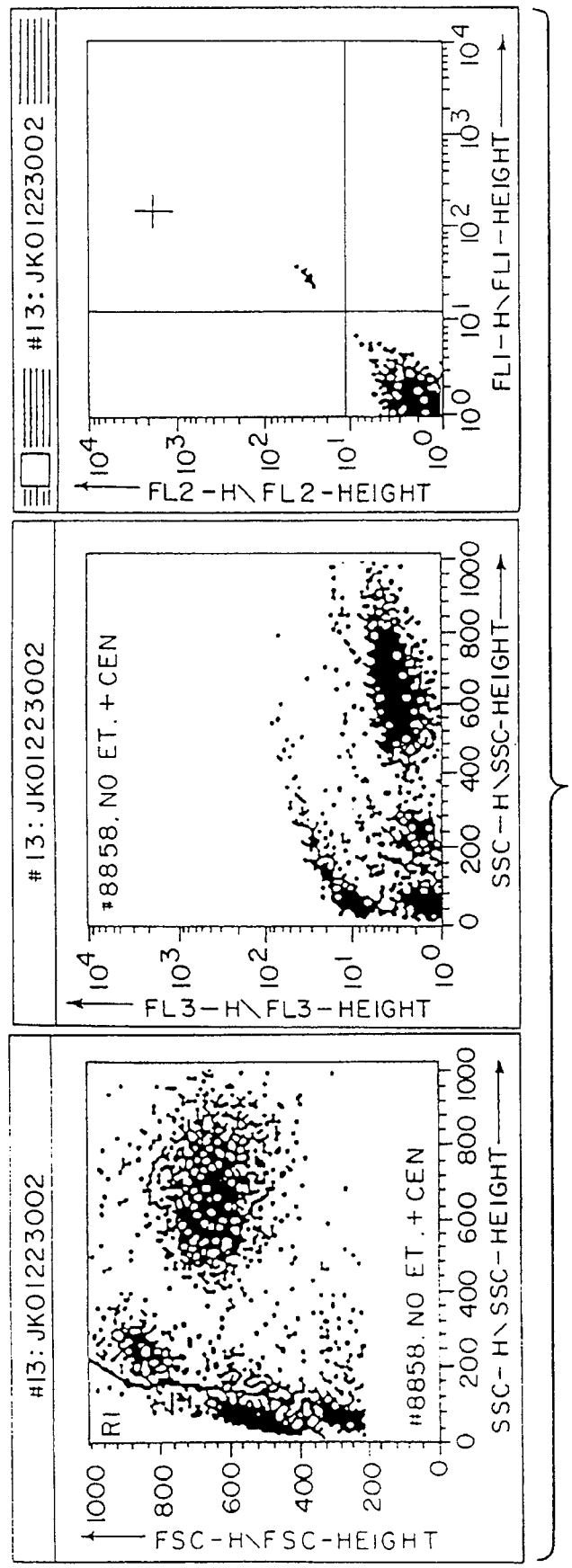
FIG. 10B is a FACScan™ display of the same blood sample as in FIG. 10A with unstained chicken erythrocyte nucleii ("CEN") added.

FIG. 10B is a FACScan™ display of the same blood sample as in FIG. 10A with unstained CEN added. As can be seen, the unstained CEN demonstrate some FRL3 autofluorescence. The region I was set to include all FL3+ events in this unstained sample, so that stained cells in the test samples can be counted in the region 2. The region 3 is set to include the CEN population only to measure the mean FL3 of the population.

Figure 10C:
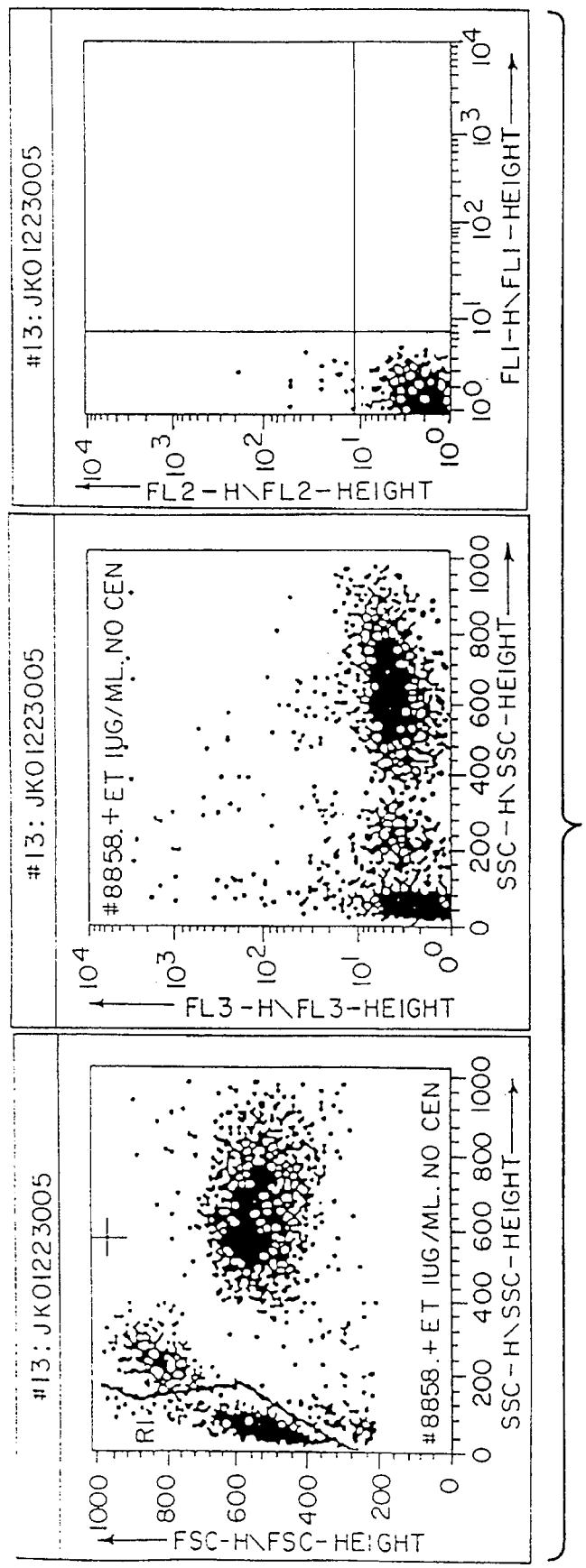
FIG. 10C is a FACScan™ display of the same sample lysed with white blood cell diluent ("WBC DIL")

FIG. 10C is a FACScan™ display of the same sample lysed with WBC DIL containing 1.0 ug/ml of NRBC dye. 1.3 % of FL2+ events were detected in μL from the gated lymphocytes and 1.08% of FL3+ events are detected from the ungated total white cell population.

Figure 10D:
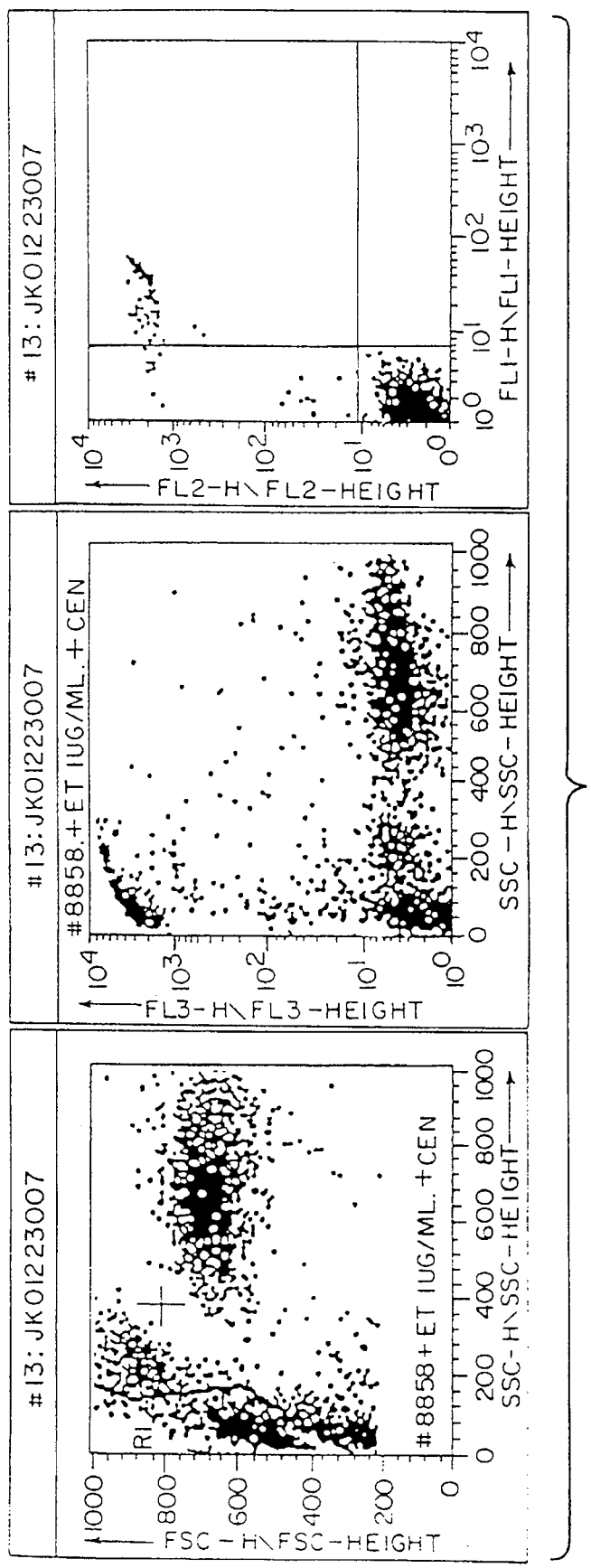
FIG. 10D is a FACScan™ display of the same sample as presented in FIG. 10C, but with CEN.

FIG. 10D is a FACScan™ display of the same sample as presented in FIG. 10C, but with CEN. The region 2 of the FL3 histogram of the ungated population shows the stained CEN population which has the mean FL3 of 3319.8.

Figure 10E:
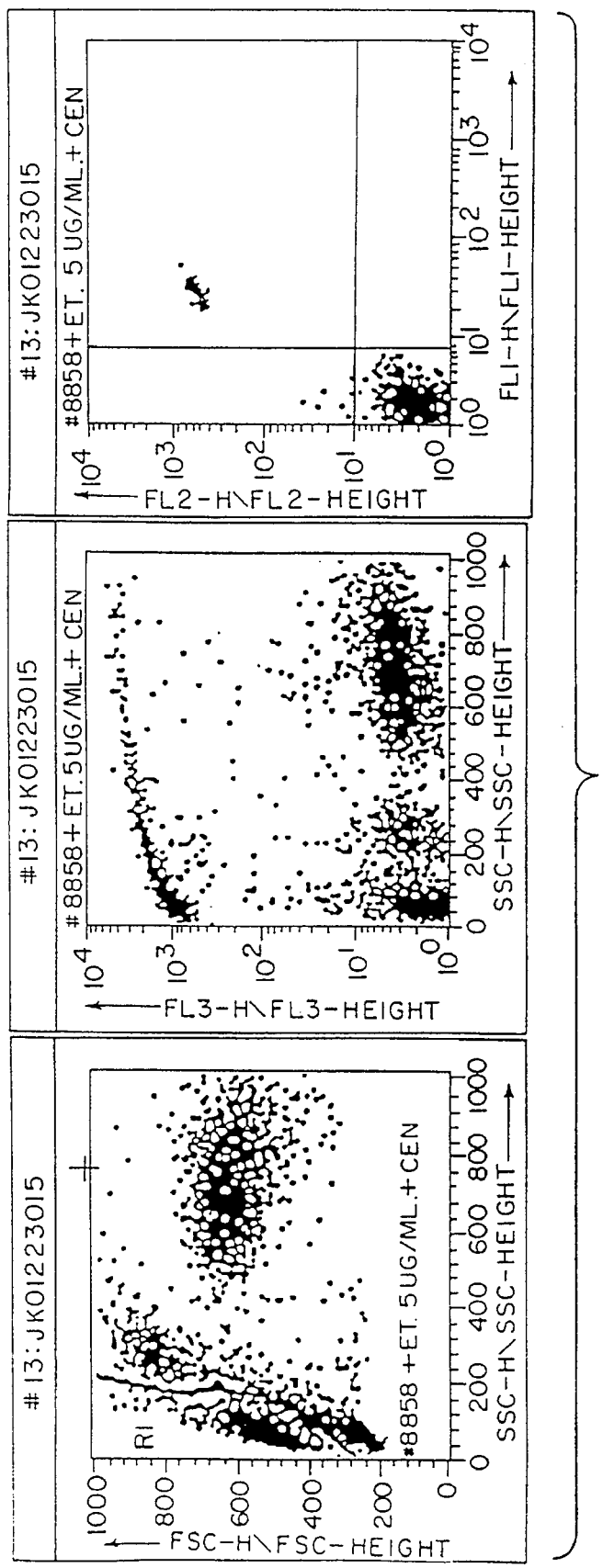
FIG. 10E is a FACScan™ display of the same sample lysed in the same diluent as FIG. 10D, but with 0.5 μg/ml of nucleated red blood cell ("NRBC") dye.

FIG. 10E is a FACScan™ display of the same sample lysed in the same diluent as FIG. 10D, but with 0.5 ug/ml of NRBC dye.

Figure 10F:
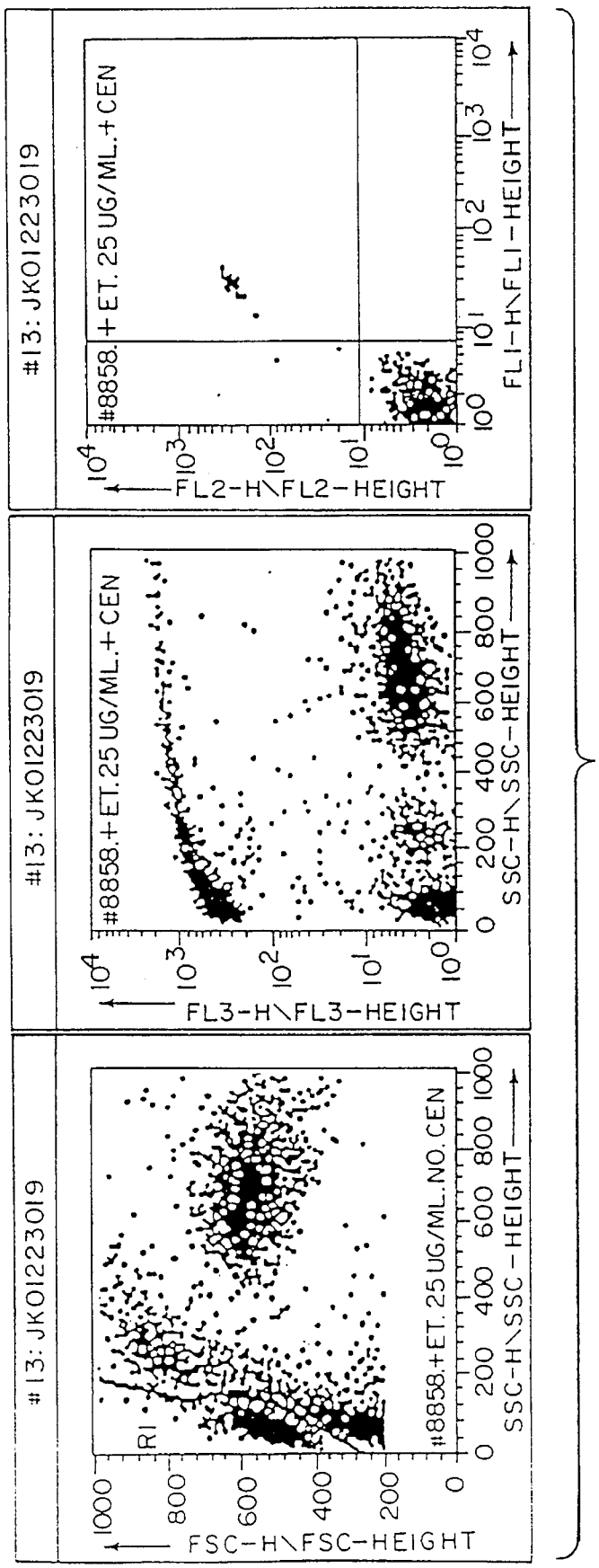
FIG. 10F is a FACScan™ display of the same sample lysed in the same diluent as FIG. 10D, but with 0.25 μg/ml of NRBC dye.

FIG. 10F is a FACScan™ display of the same sample lysed in the same diluent as FIG. 10D, but with 0.25 ug/ml of NRBC dye. As can be seen, the stained CEN is still well separated from the white cells.

Figure 11:
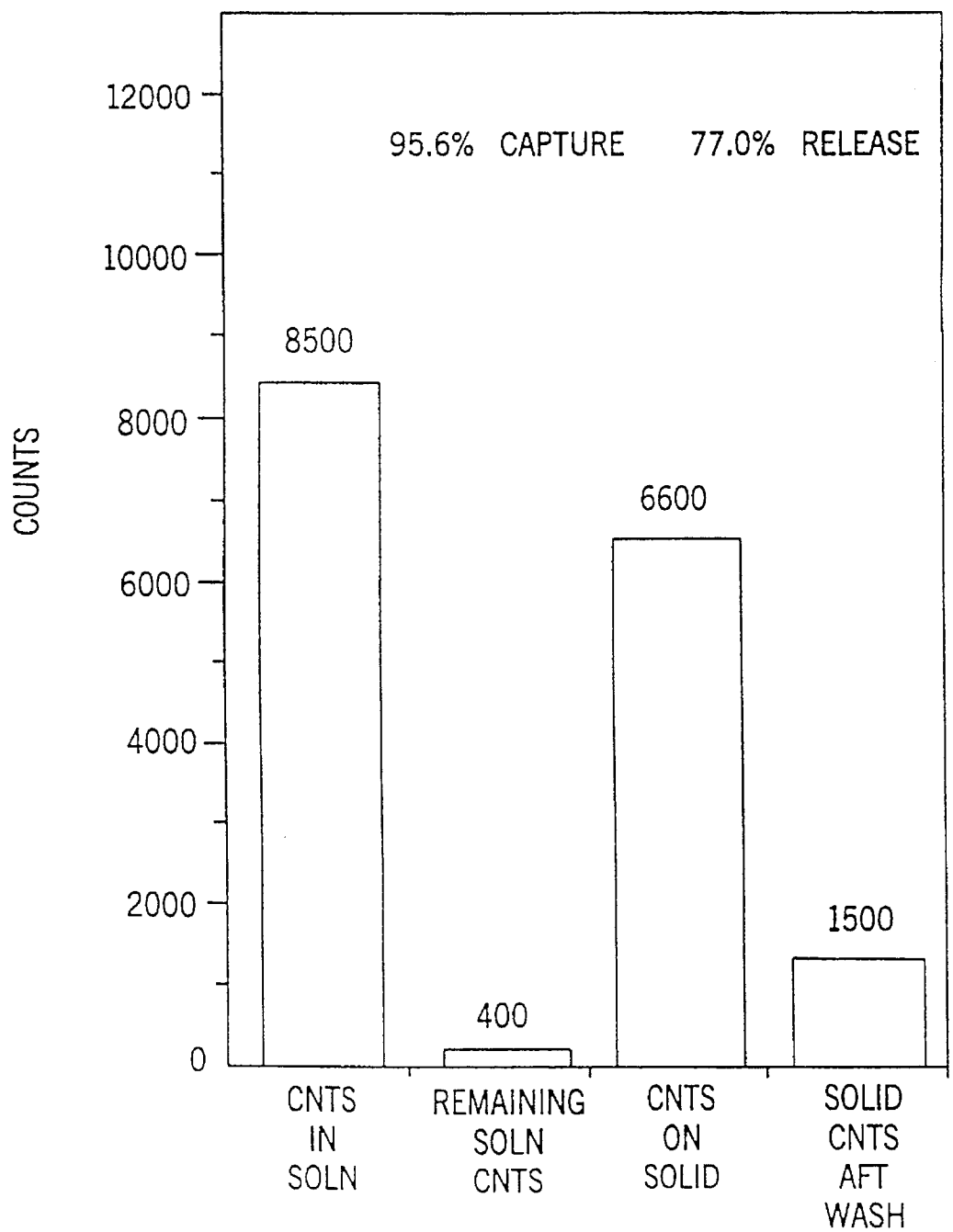
FIG. 11 is a graphical representation of the efficiency of 32P radiolabelled, restriction enzyme-nicked plasmid DNA capture onto phenathridinium activated polystyrene microparticles prepared as described in Example 6.

FIG. 11 is a graphical representation of the efficiency of 32P radiolabelled plasmid DNA capture onto phenathridinium activated polystyrene microparticles synthesized as described in Example 6. A: initial radioactive counts in solution accounting for the total DNA concentration; B: radioactive counts remaining in solution after removal of DNA via centrifugation as described in Example 6; C: initial radioactive counts on the DNA bound to the microparticle by the phenthridine moiety before release is initiated by NaOH; and D: radioactive counts remaining on the solid after removal of DNA with NaOH.

Figure 12:
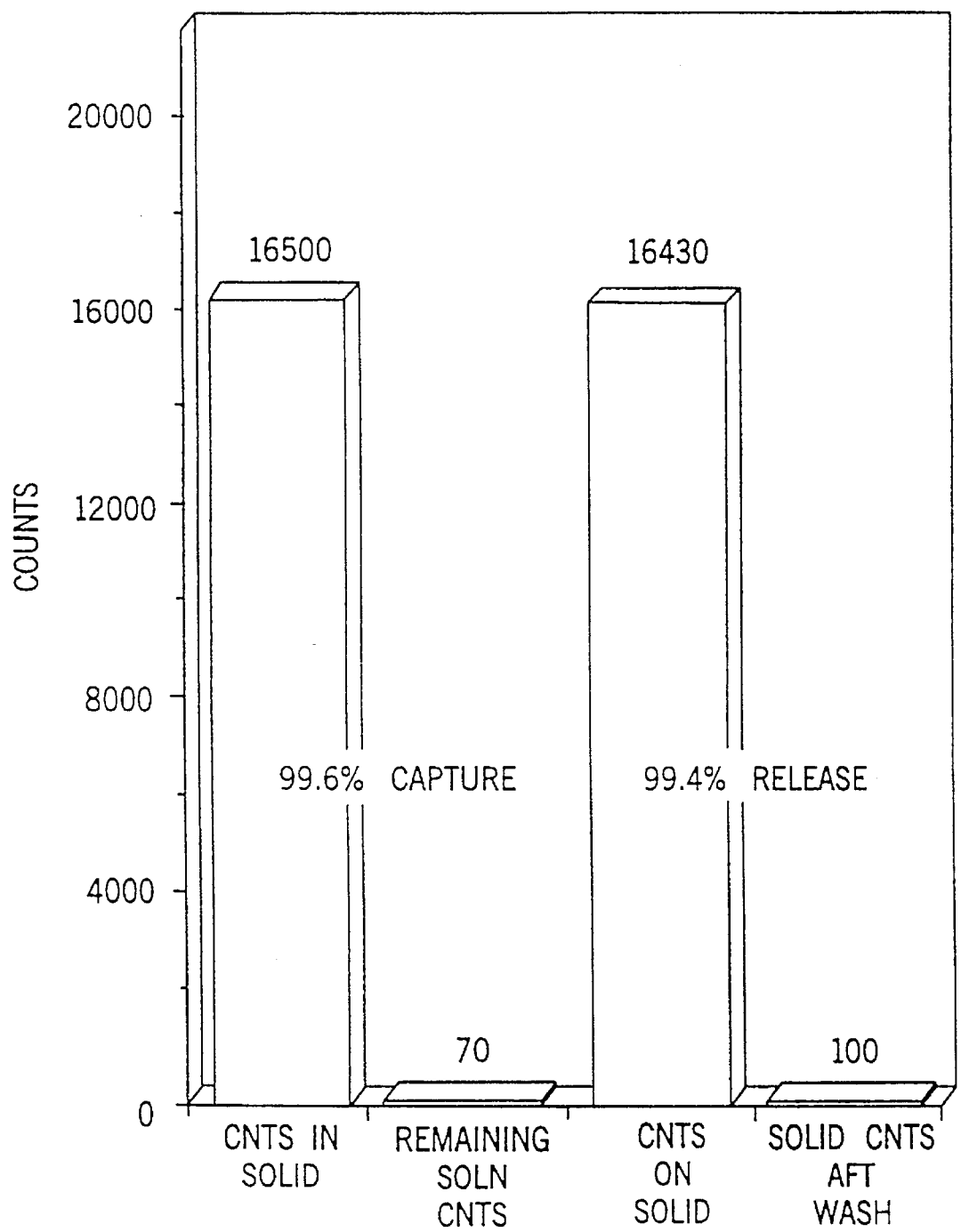
FIG. 12 is a graphical representation of the efficiency of 32P radiolabelled plasmid DNA capture onto phenathridinium activated carboxymethyl sepharose beads synthesized as described in Example 6.

FIG. 12 is a graphical representation of the efficiency of 32P radiolabelled plasmid DNA capture onto phenathridinium activated carboxymethyl sepharose beads synthesized as described in Example 6. A: initial radioactive counts in solution accounting for the total DNA concentration; B: radioactive counts remaining in solution after removal of DNA via centrifugation as described in Example 6; C: initial radioactive counts on the DNA bound to the microparticle by the phenthridine moiety before release is initiated by NaOH; and D: radioactive counts remaining on the solid after removal of DNA with NaOH.

The present intercalator compounds are substantially monointercalators, versus the polyfunctional (bis) intercalators. The monointercalators according to the present invention are most suitable for application using a multitude of intercalators and substituted intercalators which when combined with and functionalized by the various "chains or tails" ("T"), where T is the chain comprised of R, $R_1$, $R_2$, $R_3$, $R_4$, W, X, Y and Z and bounded by the brackets in the previously discussed formulas, which provide high binding to DNA and RNA and lack of self-quenching and superior transport kinetics. Representative "I" moieties are given in FIG. 13.

The invention is further defined by the following Examples, which provide basis for the FIGURES and are intended to be illustrative, but not limiting.

EXAMPLE 1

Synthesis of phenanthridinium Triamine (PTA) 24 And Precursor Intermediates 20–23

Figure 14:
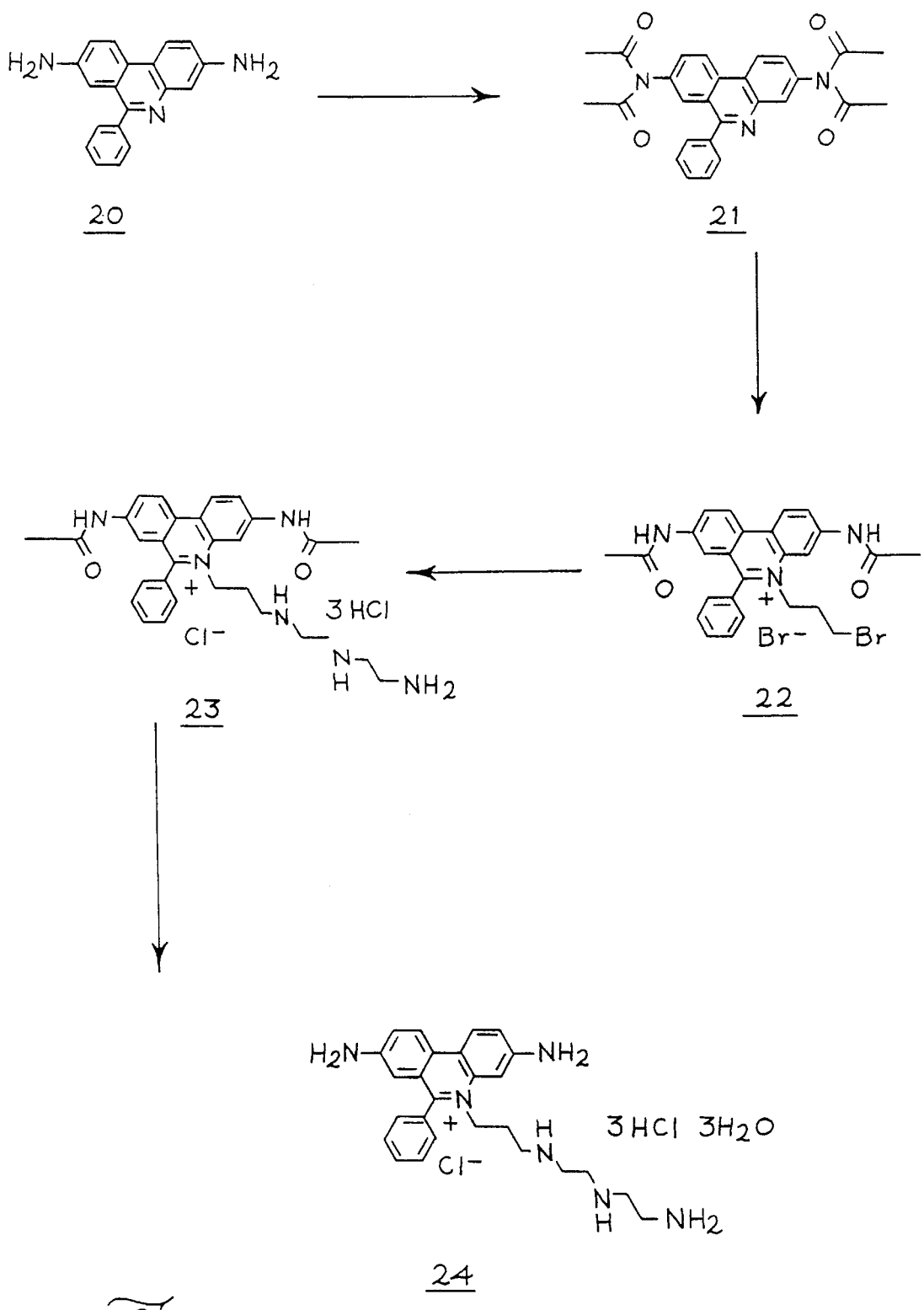
FIG. 14 is a reaction scheme for the synthesis of compound 24 and its precursors.

PTA 24, a compound according to the invention, was synthesized through the sequence shown in the schematic as shown in FIG. 14. The experimental procedures used to obtain product 24 are as illustrated therein. Intermediate 21. Starting Intermediate 20, 3,8 Diamino 6-phenyl phenathridine (25.0 g, 0.0876 moles), was obtained from the Aldrich Chemical Company (Milwaukee, Wis.) and added to a single neck 3.0 liter round bottom flask under Argon and equipped with a magnetic stir bar and a reflux condenser. To this vessel, 1.0 liter of dry pyridine was added while stirring. Stirring of the resulting suspension was continued for 15 minutes until all the solid had dissolved. A catalytic amount of N,N-dimethylaminopyridine (1.07 g, 0.0086 moles) was added to this solution while stirring. Acetic anhydride (462 g, 4.9 moles) was then added and the resulting reaction mixture was refluxed for 8–12 hours. The reaction mixture was then allowed to cool and the solvent was removed in vacuo. For purification of the Product II, a gradient silica gel column was performed using 2.0 liters of 45/40/10/5 Ethyl acetate/hexane/$CH_2Cl_2CH_3OH$ followed by 1.0 liter of 40/40/10/10 EtOAc/hexane/$CH_2Cl_2/CH_3OH$. Fractions of 10.0 ml were collected and appropriate fractions were recombined and the solvent was removed in vacuo. The sticky gum-like residue was then dissolved in hot EtOH (220 ml) and precipitated by cooling to 0° C. The mother liquor was decanted off and 200 ml of fresh EtOH was added. The solid was redissolved by heating and allowed to crystallize at −4° C. for 48 hours. Crystals were collected from both the mother liquor and the second recrystallization and were washed with a small amount of cold EtOH and dried under high vacuum for several hours. Isolated yield of pure product after column chromatography and two recrystallizations was 32 %. $^1$H NMR $CD_3OD$ (300 MHz) 9.1 (d, 1H 8.82 Hz), 9.0 (d, 1H, 8.75 Hz), 8.08 (s, 1H), 7.95 (s, 1H), 7.92 (d, 1H, 4.5 Hz), 7.8 (m, 3H), 7.65 (m, 3H), 2.45 (s, 6H), 2.35 (s, 6H); $^{13}$C NMR CD3OD (75.45 MHz) 174.5, 163.7, 145.3, 142.1, 140.6, 139.9, 134.4, 133.8, 130.8, 130.6, 129.8, 127.3, 125.9, 125.6, 124.8, 27.1, Exact Mass Calc. for $C_{27}H_{23}N_3O_4$, Calc. 453.1688 exact mass, Obs: 453.1683; CH analysis Calc for $C_{27}H_{23}N_3O_4$ C: 71.51 H: 5.11 N: 9.27 Found C: 71.77 H: 5.10 N:9.20. Intermediate 22. Intermediate 22 was synthesized from the diamide 21 via a modification of a literature procedure (Gaugain et al., *Biochemistry*, Vol. 17, No. 24, 1978, pp. 5071–5078) for quarternization of the diamide of 3,8 Diamino-6-phenyl phenanthridine. Diamide 21 (10.5 g, 0.023 moles) was placed in a 2.0 liter round bottom flask under argon and equipped with a magnetic stir bar and reflex condenser. 1,3 Dibromopropane (1.0 liter, 9.86 moles) was added to this flask and the resultant mixture was brought to reflux for 7 hours. The solution was cooled overnight and the precipitant was filtered and washed with diethyl ether. Obtained 10.44 g (68.7%) of crude material 22. This material was recrystallized from $CH_3OH$ to yield 5.3 g of diacetyl bromide 22. $^1$H NMR $CD_3OD$ (300 MHz) delta 10.75 (s, 1H), 10.45 (s, 1H), 9.3 (s, 1H), 9.09 (d, 9.2 Hz, 1H), 9.04 (d, 9.2 Hz, 1H), 8.45 (d, 9.1 Hz, 2.2 Hz, 1H), 8.12 (s, 1H), 8.07 (d 9.0 Hz, 1H), 7.95 (m, 3H), 7.85 (m, 3H), 5.0 (t, 9.0 Hz, 3H), 3.6 (t, 6.0 Hz, 2H), 2.65, 2.38 7.75 $^{13}$C NMR $_{26}$DMSO (75.45 MHz) delta 169.9, 169.3, 163.8, 142.1, 139.9, 134.2, 131.5, 130.5, 129.5, 128.4, 125.9, 125.4, 123.6, 122.3, 121.6, 119.0, 107.7, 55.7, 30.7, 24.5, 24.2; exact mass Calc. for $C_{26}H_{29}N_3O_2Br_2$ free salt (FAB+) 490.1131 Obs: 490.1139; CH analysis Calc. for $C_{26}H_{29}N_3O_2Br_2$ H: 4.41 C: 54.66 N:7.36 Found H: 4.25 C: 54.65 N: 7.30. Intermediate .23. Intermediate 22 (5.3 g, 0.0093 moles) was added to a 250 ml round bottom flask equipped with a magnetic stir bar and reflux condenser. Methanol (150 ml) was then added to this flask while stirring under nitrogen and diethylene triamine (29.2 g, 0.283 moles) was added while stirring was continued. The resultant transparent solution was heated to reflux overnight under nitrogen. This solution was then allowed to cool to room temperature and poured into distilled $H_2O$. Then this mixture was concentrated in vacuo until only the $H_2O$ remained. An additional 50–75 ml $H_2O$ was added and the solution was allowed to cool to 0° C. The solid was then filtered and washed with ice cold water. This material was then redissolved in EtOH and precipitated with 10 N HCl. After filtration of the suspension, the resultant solid was recrystallized from hot ethanol upon cooling to 0° C. for 15 minutes. A second crop was also collected from the second filtrate upon standing and by precipitation with EtOH from the first filtrate. These solids were then combined and the final product 23 (2.5 g) was obtained after high vacuum overnight. $^1$H NMR $CD_3OD$ (300 MHz) delta 9.2 (s, 1H), 9.05 (d, 1H), 8.95 (d, 1H), 8.4 (broad s, 2H), 8.3 (broad s, 1H), 7.9 (broad m, 3H), 7.7 (broad m, 2H), 5.1 (broad m, 1H), 3.9 (broad s, 3H), 3.45 (broad m, 2H), 3.85 (broad m, 2H), 2.5 (broad m, 3H), 2.3 (broad m, 3H); MS Calc. for free salt $C_{30}H_{37}N_6O_2$(FAB+) 513 Obs: 513. Product 24. Synthesis and purification of the phenanthidinium triamine, PTA, 24 was accomplished by the following protocol. Triamine 23 (2.35 g, 0.0036 moles) was dissolved in 75.0 ml methanol and 75 ml of 4N HCl was added. The mixture was refluxed for 2 hours and allowed to cool. Ethanol was added to this solution and resulting precipitate was filtered and washed with a minimal amount of cold ethanol. The filtrate was reconcentrated and fresh ethanol and concentrated aqueous HCl was added. This resulting precipitate was also filtered. Next, this filtrate was concentrated to near dryness and $Et_2O$ was added and the solid filtered off. The last remaining unfilterable residue was then dissolved in concentrated HCl and precipitated with EtOH. This material was filtered and washed with ethanol, combined all solid materials from the above sequence and subjected this material to high vacuum overnight to obtain 2.03 g total of the high affinity fluorescent DNA stain PTA 24. $^1$H NMR $d_6$-DMSO (300 MHz) delta 10.0 (broad s, 2H), 9.65 (broad s, 2H), 8.68 (d, 14.2 Hz, 2H), 8.35 (broad s, 2H), 7.75 (m, 4H), 7.65 (s, 1H) 7.55 (d, 9.2 Hz, 2H), 7.35 (d, 9.2 Hz, 2H), 6.28 (s, 1H), 4.5 (broad s, 2H), 4.0 (broad s, 8H), 3.4 (broad s, 2H), 3.0 (broad s, 2H), 2.3 (broad m, 2H); $^{13}$C NMR $d_6$-DMSO (75.45 MHz) δ 159.7, 151.1, 134.6, 131.7, 130.9, 129.4, 128.8, 128.4, 124.9, 122.9, 120.1, 117.4, 99.6, 51.4, 43.8, 42.5, 40.3, 34.9, 18.5; High resolution mass spec. $C_{26}H_{33}N_6$(FAB+)Calc. 429.2767, Obs: 429.2766; CH analysis Calc for $C_{26}H_{37}N_6Cl_4 3H_2O$ was H 6.89 C 49.61 N 13.35 Found H: 6.16; C 49.74 N: 13.08.

EXAMPLE 2

Hybridization Assay

PTA 24 was used to quantitate hybridization when a target oligonucleotide was titrated with its complementary partner. A comparison of ethidium bromide staining versus PTA 24 for detecting this hybridization, as per the following protocol, can be found in FIG. 9 and the comparison of ethidium homodimer versus PTA 24, as per the following protocol, can be found in FIG. 8. Complementary strands of DNA (oligodeoxythymidylic acid, $d(pT)_9$ and oligodeoxyadenylic acid $(d(pA)_9)$ were obtained from the Sigma Chemical Co. in St. Louis, Mo. A stock solution of d(pA)9 was made at 5 units/ml of 0.05M TRIS, 0.2N NaCl, 1 MM EDTA, pH 8.4. For polyA, $\epsilon$=8.4 AU/mM cm or 8,400 $M^{-1}cm^{-1}$; therefore, with 9 base pairs for d(pA)9, the $\epsilon$ is 75,600 $M^{-1}cm^{-1}$. This stock was then diluted 10× to obtain stock at $6.61 \times 10^{-6}$M, or 6.6 μM. The $d(pT)_9$ stock was made at 25 units/5.0 ml and used for titration without further dilution in the same buffer. Since the $\epsilon$ for polyT is 8.15 AU/mM cm or 8,150 M-1cm-1 per base pair, or 73,350 M-1cm-1 per oligo, the concentration of the oligo stock was 68 μM in DNA molecules. A titration was performed using a Hitachi F-4010 Fluorescence Spectrophotometer equipped with 0.5 ml microcells to obtain fully corrected spectra and an excitation wavelength of 488–550 nm (optimal around 534) and an emission wavelength of 600–650 nm (optimal around 625). Equivalents of $d(pT)_9$ were added at the following increments: 0.02, 0.05, 0.080, 0.150, 0.300, 0.500, 0.700, 1.00, 2.00, 5.00 equivalents. Each sample in the titration curve was prepared individually by dividing the initial d(pA)9 stock into 10×1.0 ml aliquots. The addition of complement was then accomplished by micropipetting an appropriate amount (2, 5, 8, 15, 30, 50, 70, 100, 200, and 500 μl, respectively) of d(pT)9 stock to each of a series of the 10 aliquots. Each aliquot, obtaining progressively larger molar ratios of the two complementary strands, was incubated at ambient temperature for 15 minutes, the dye was added as 20.0 μl aliquots of a 154 μM solution of the dye in 0.05M TRIS, 0.2N NaCl, 1 mM EDTA, pH 8.4 buffer. This corresponds to a dye/DNA b.p. ratio of 1/20 at saturation with complementary oligo. Overall concentrations of dye and oligo vary in the saturation plot because of the use of varied increments additions from the same stock solution. After an additional 15 minute incubation time, the relative fluorescence intensity was then read at 625 nm and recorded to generate a standard curve which is directly proportional to the quantity of dsDNA hybridization, or target sequence, under these conditions. The background fluorescence, or initial residual fluorescence, is then subtracted out as a constant for all curves for comparison of the various titration curves on the same graph.

EXAMPLE 3

Gel Electrophoresis Application

An agarose gel was run to compare the staining intensity of ethidium bromide (Aldrich Chemical Co., Milwaukee, Wis.), ethidium homodimer −1 (Molecular Probes, Cat. #E 1169, Eugene, Oreg.), and PTA 24 stain. Plasmid, pBR322, at 2.1 mg in 7 ml stock was incubated at 37° C. for 1 hour with 1 ml of BAMH restriction enzyme with 2 ml 10X React2 Buffer and diluted to 20 ml total with 10 ml $H_2O$. This mixture was then used to prepare 3 stocks of nicked pBR322 plasmid at 0.63 mg per 6 ml for each vial. Each of these stocks were diluted further with $H_2O$ and 20% glycerol to final DNA stocks of 20 ng/ml, 800 pg/ml, 160 pg/ml, and 40 pg/ml with a 1:4 ratio of dye to DNA base pairs in each for a total of 12 stocks. A 5 ml aliquot of each stock was loaded into 12 separate lanes in agarose gel and electrophoresis was run for 30 minutes in 4 mM TRIS, pH8.2, with 0.01 mM EDTA buffer. The gel was then removed and photographed under exposure to U.V. light in a conventional gel box.

EXAMPLE 4

Protocol For Synthesis Of Intercalator Activated Carboxymethyl Styrene Microparticle Capture Reagent The synthesis of intercalator derivatized solid phase microparticle (MP) capture reagent was accomplished by the scheme depicted in the following schematic and effected by the following procedure:

A 45 aliquot of 0.275±μm microparticles (Seradyne, Indianapolis, Ind.) were placed in a 4 ml vial and the surfactant was exchanged out using Bio-Rex 50 I-D ion exchange mixed bed resin (Bio-Rad, Richmond, Calif.). After gentle shaking for 2 hours, the resin was filtered out from the mixture by using a coarse fritted glass funnel equipped with a reduced pressure collection chamber. The sample was diluted to a concentration of MP at 10% solids by weight. The total amount of equivalents of reactive carboxylic acid were calculated from the titration specifications of the vendor.

A stock solution of sulfo N-hydryoxysuccinimide (Pierce, Rockford, Ill.) was made at 11 mg/ml (20 mM) in $H_2O$ and a stock solution of EDAC (Sigma Chemical Co., St. Louis, Mo.) at 10 mg/ml (5 mM) was made in $H_2O$. Five equivalents of EDAC (290 μl stock) was added to the carboxymicroparticle reaction mixture, followed by 5.0 equivalents of sulfo N-hydryoxysuccinimide (330 μl stock). This mixture was allowed to incubate at room temperature for 2 hours and then a 2.0 molar equivalent of PTA 24 (4 mg) was added at a concentration of 8 mg/400 μl, or 2.0 mg/100 μl in pH 8.0 0.1 N NaCl 0.1N Pi phosphate buffer. N-hydryoxysuccinimide (Pierce) can be substituted for sulfo N-hydryoxysuccinimide if it is first dissolved in a stock of DMF (Dimethyl formamide) and aliquoted as described above. After allowing 24 hours for complete reaction, the free dye was then removed by centrifugation, removal of mother liquor, and resuspension for several attempts until the solution went clear and no more dye was extracted from the samples. The purified capture reagent was then diluted to a stock of 2–4% solids in $H_2O$.

Figure 15:
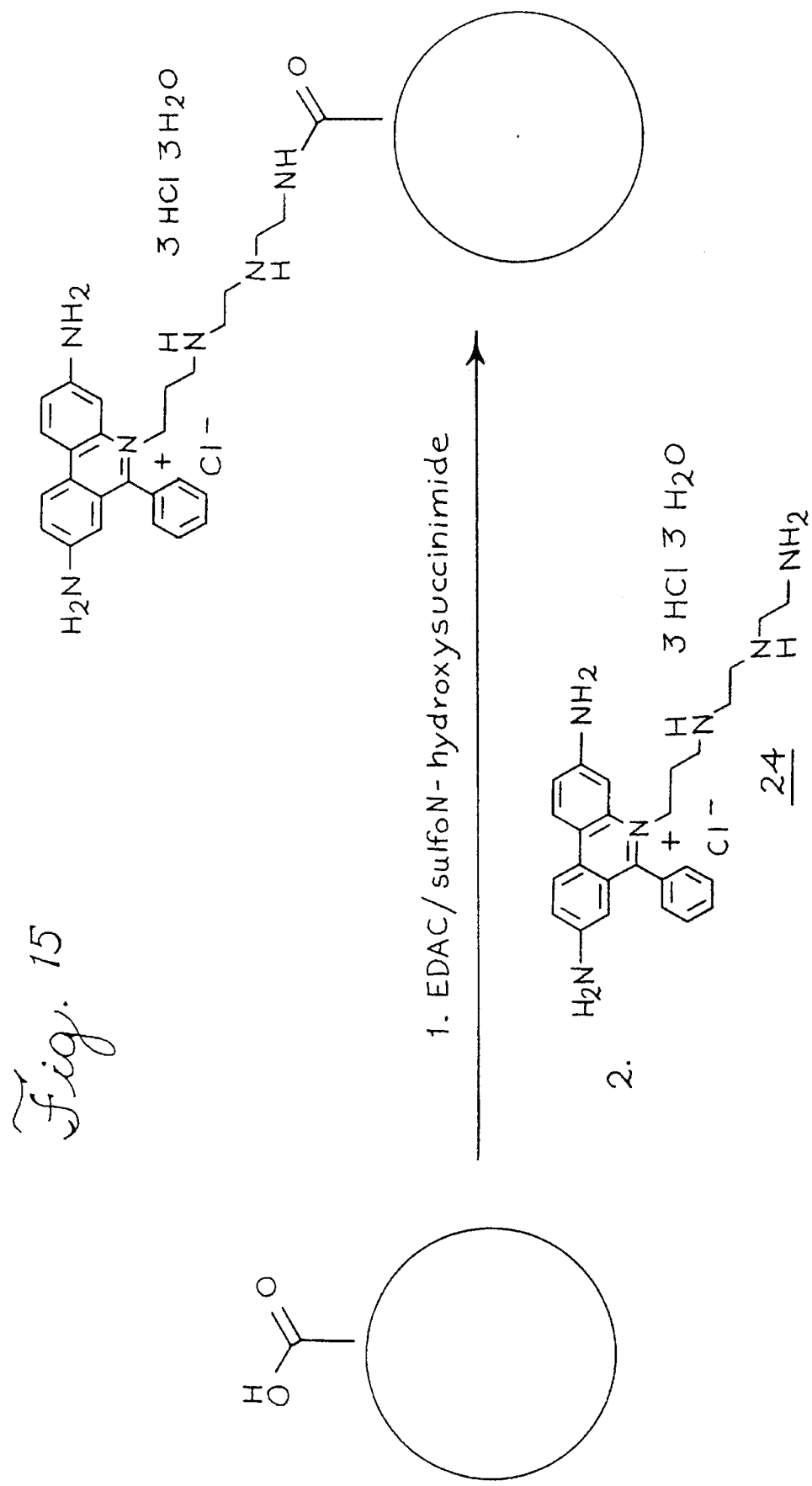
FIG. 15 is a schematic representation of intercalator derivatized solid phase microparticle.

A general schematic representation of this Example is given in FIG. 15.

EXAMPLE 5

Solid Phase DNA Capture

CM (carboxy modified) Sepharose was obtained from Sigma Chemical Co. (St. Louis, Mo.) in an ethanol/$H_2O$ mixture. The solution was estimated at 50% solids based on total volume occupied by the solid and liquid portions on extended standing. This suspension was then mixed uniformly and diluted to 10% solids. 200 μl of this stock was removed and calculated at 0.12 meq/gram to be 0.012 meq of acid total. Stock of EDAC and N-hydryoxysuccinimide were prepared and 5.0 equivalents of each activating reagent were added to this suspension. For this preparation, 13.2 mg (in 1.32 ml) HOSuc and 11.25 mg EDAC (in 1.02 ml) were used and 8.0 mg total of the PTA 24 intercalator. After incubation for 2–24 hours, the suspensions were then cleaned by repeated washing and gentle centrifugation steps until no more color was removed from the solid upon dilution. A stock was prepared at 10 % solids in $H_2O$. Note that controls were run with PTA 24 modified and nonmodified solid phases and minimal non-specific capture of DNA occurred with the underivatized materials.

EXAMPLE 6

Protocol For DNA Capture By Intercalator Modified Solid Phase

1. Place 50 μl of activated microparticles in a 1.5 ml eppendorf.

2. Add 150 μl of PBS and 1–20 u of a 5.0 kb linearized plasmid end-labeled with $^{32}P$. Alternatively, added 1–50 μl of biological sample or another purified DNA.

3. Mix by rotation for one hour at ambient temperature.

4. Pellet the microparticles by centrifugation at 5,000 rpm for 5 minutes.

5. Wash one or two times with 200 μl of PBS.

6. Release the DNA by adding 50 μ of 0.5 M NaOH and mix for 15 minutes at ambient temperature.

7. Centrifuged and collected the supernatant, which contains released DNA.

The efficiency of DNA capture was measured using $^{32}P$ radiolabelled plasmid DNA in the above-described protocol. The results are found in FIG. 11 using the intercalator modified polystyrene microparticles prepared as per Example 4 and FIG. 12 and using the intercalator modified CM Sepharose beads prepared per Example 5. The data indicates that the DNA binding to the intercalator modified solid phase was specific and induced by the covalent attachment of intercalator 24 to the solid phase.

EXAMPLE 7

Relative Staining Intensities Of Ethidium Homodimer And Phenanthridinium Triamine 24 In A Flow Cytometric Study Of Chicken Erythrocyte Nuclei (CEN)

Protocol: 50 μl of whole blood sample from two in-house donors and 3 μl of CEN suspension was added to 1.0 ml of pre-warmed at 40° C. WBC DIL without and with the NRBC dye at 1 μg/ml concentration, mixed, introduced to the FACScan™ and 20" readings were acquired. Chicken erythrocyte nuclei (CEN) were used to measure the brightness of the FL3 staining (mean FL3 of CEN). The whole blood samples used were about 4–5 hours old. The data for this experiment is shown in FIGS. 1–6.

EXAMPLE 8

Comparative Performance Of Reduced Phenathridinium Triamine 24 Dye Concentrations Relative To Ethidium Homodimer The effect of a reduction in PTA 24 dye concentration (FIGS. 10A–F) relative to ethidium homodimer was demonstrated as follows:

Method: The experiment was designed to show the correlation between the dye concentration and the percent of FL2+ events in the UL quadrant on the FL1 versus FL2 dot plots. The WBC DIL used contained 0.5% weight/volume of ammonium chloride, 0.075% of volume of formaldehyde, 0.01% weight/volume of saponin, 0.01% weight/volume of potassium bicarbonate, and 20 mM acetate buffer with a pH of about 6.0 and an osmolality of about 270 mOsm per liter. 50 μl of whole blood sample from each of two in-house donors was added to 1.0 ml of pre-warmed at 40° C. WBC DIL without and with the NRBC dye of varying concentration (0.25, 0.50, 0.75, and 1.0 ug/ml), mixed, introduced to the FACScan™ and 20" readings were acquired. Chicken erythrocyte nuclei (CEN) suspension was used to measure the brightness of the FL3 staining (mean FL3 of CEN). The whole blood samples used for this experiment were about 6 hours old.

It was observed that the CEN DNA is essentially indistinguishable from the background without the PTA 24 (FIG. 10B) and that the dye concentration can be reduced to 75% of that of ethidium homodimer (FIG. 5) and still maintain acceptable separation from the background (FIG. 10F). Such a reduction can lead to significantly reduced non-specific binding and substantial savings in dye usage.

EXAMPLE 9

Viability Dyes On The Coulter Elite™ Flow Cytometer

Cell Isolation protocol: Each tube of ficol isolated cells were treated as follows: PBS with 0.1% NaAzide and 1.0% albumin (Sigma catalogue #1000-3) Ficol specific gravity 1.119 (Sigma Histopague catalogue#1119-1).

10 ml of whole blood (EDTA anticoagulant) was diluted with 10 ml of PBSW. Into 4, 15 ml conical bottom tubes, 5 ml of the diluted blood was layered over 5 ml of ficol. The tubes were spun for 30 minutes at 400×G. The interface layer which contains the lymphocytes, monocytes, granulocytes and platelets was aspirated and washed once in 5 ml PBS, by centrifuging tubes at 300×G for 6 minutes. The cell pellet was resuspended in PBS, cells counted, and adjusted to 8.5×106 cells per ml.

Cell Staining Protocol:

Dye solutions:

PTA 24—Stock solution 10 ug/ml made by dissolving PTA 24 in PBS with 0.1% NaAzide.

Propidium iodide (P.I.)—Stock solution 0.5 mg/ml made by dissolving P.I. in PBS with 0.1% NaAzide.

P.I. Staining:

In 12×75 mm tube, 117.6 μl of cells was mixed gently with 14.7 μl of P.I. stock dye solution. After 20 seconds, the tube was placed on a Coulter Elite™ flow cytometer and data collected. Procedure from "Discrimination of Viable and Non-Viable Cells Using Prodidium Iodide in Two Color Immunofluorescence", *Cytometry* by Sasaki et al., Vol. 8, 1987, pp. 413–420.

PTA 24 Staining:

In 12–75 mm tube, 23.5 µl of cells was gently mixed with 76 µl of PTA 24 stock dye solution. After 20 seconds, the tube was placed on a Coulter Elite™ flow cytometer and data collected.

Trypan Blue Staining:

In 12×75 mm tube, 5 µl of working solution Trypan Blue and 5 µl of cells were gently mixed and cells counted in a mehacytometer using standard white light illumination. A minimum of 500 cells were counted within 3 minutes of staining. Procedure from Selected Methods in Immunology by Mishell and Shiigi, 1980, pp. 16–17.

Flow cytometer protocol: Cells analyzed on the Elite™ flow cytometer (Coulter Electronics, Inc.).

Samples were excited with an argon laser at 488 nm and 15 mW of power. Data was gated on the basis of size and granularity to exclude red blood cells, platelets and debris. The linear dye fluorescence of the gated distribution was analyzed using unstained cells as a control. The percent positive events (dead cells) and the mean fluorescence of the dead cell distribution were recorded.

TABLE 1

Viability Dyes on the Coulter Elite ™ Cytometer

| Time Point | Sample | % Positive (Dead Cells) |
|---|---|---|
| 5 hr | P.I. | 2.5 |
|  | PTA | 2.2 |
|  | Trypan Blue | 1.4 |
| 27 hr | P.I. | 6.3 |
|  | PTA | 7.7 |
|  | Trypan Blue | 4.8 |
| 103 hr | P.I. | 26.8 |
|  | PTA | 19.1 |
|  | Trypan Blue | 10.2 |

EXAMPLE 10

Synthesis Of Compound 25

Compound 22 (0.075g, 0.00013 moles) was added to a 50 ml round bottom flask equipped with a magnetic stir bar and reflux condensor. Methanol (10 ml) was then added to this flask while stirring under nitrogen and tris(2-aminoethyl)amine (1.016 g, 0.00518 moles) was added while stirring was continued. The resultant transparent solution was heated to reflux overnight under nitrogen. This solution was then allowed to cool to room temperature and poured into distilled $H_2O$. Then this mixture was concentrated in vacuo until only the $H_2O$ remained. An additional 50–75 ml $H_2O$ was added and the solution was allowed to cool to 0° C. The solid was then filtered and washed with ice cold water. This material was then redissolved in EtOH and precipitated with 10 N HCl. After filtration of the suspension, the resultant solid was recrystallized from hot ethanol upon cooling to 0° C. for 15 minutes. A second crop was also collected from the second filtrate upon standing and by precipitation with EtOH from the first filtrate. These solids were then combined and the final product 23 (2.5 g) was obtained after high vacuum overnight. Material was then carried through to the next step of hydrolysis.

The amine residue from above was dissolved in 10.0 ml methanol and 15 ml of 4N HCl was added. The mixture was refluxed for 2 hours and allowed to cool. Ethanol was added to this solution and resulting precipitate was filtered and washed with a minimal amount of cold ethanol. The filtrate was reconcentrated and fresh ethanol and concentrated aqueous HCl was added. This resulting precipitate was also filtered. Next, this filtrate was concentrated to near dryness and $Et_2O$ was added and the solid filtered off. The last remaining unfilterable residue was then dissolved in concentrated HCl and precipitated with EtOH. This material was filtered and washed with ethanol, combined all solid materials from the above sequence and subjected this material to high vacuum overnight to obtain the of the high affinity fluorescent DNA stain phenathridium amine derivative 25. High resolution mass spec. $C_{28}H_{38}N_7$(FAB+) Calc. 472.3189 Ohs: 472.3191.

The structural formula of compound 25 is shown in FIG. 16.

EXAMPLE 11

Synthesis Of Compound 26

Intermediate 22 (0.2 g, 0.406 mmoles) was added to a 50 ml round bottom flask equipped with a magnetic stir bar and reflux condensor. Methanol (10 ml) was then added to this flask while stirring under nitrogen and 1,4 Bisamino(3-aminopropyl)piperazine (3.3 g, 16.26 mmoles) was added while stirring was continued. The resultant transparent solution was heated to reflux overnight under nitrogen. This solution was then allowed to cool to room temperature and poured into distilled $H_2O$. Then this mixture was concentrated in vacuo until only the $H_2O$ remained. An additional 50–75 ml $H_2O$ was added and the solution was allowed to cool to 0° C. The solid was then filtered and washed with ice cold water. This material was then redissolved in EtOH and precipitated with 10 N HCl. After filtration of the suspension, the resultant solid was recrystallized from hot ethanol upon cooling to 0° C. for 15 minutes. A second crop was also collected from the second filtrate upon standing and by precipitation with EtOH from the first filtrate. These solids were then combined and the diamine amine product was obtained after high vacuum overnight. Material was then carried through to the next step of hydrolysis.

The amine residue from above was dissolved in 10.0 ml methanol and 15 ml of 4N HCl was added. The mixture was refluxed for 2 hours and allowed to cool. Ethanol was added to this solution and resulting precipitate was filtered and washed with a minimal amount of cold ethanol. The filtrate was reconcentrated and fresh ethanol and concentrated aqueous HCl was added. This resulting precipitate was also filtered. Next, this filtrate was concentrated to near dryness and EhO was added and the solid filtered off. The last remaining unfilterable residue was then dissolved in concentrated HCl and precipitated with EtOH. This material was filtered and washed with ethanol, combined all solid materials from the above sequence and subjected this material to high vacuum overnight to obtain the of the high affinity fluorescent DNA stain phenathridium amine derivative 26. Mass Spec. $C_{26}H_{30}N_5$(FAB +) Calc. 4 12, Ohs: 412.

The structural formula of compound 26 is shown in FIG. 16.

EXAMPLE 12

Synthesis of Compound 27

Intermediate 22 (0.06 g, 0.12 mmoles) was added to a 50 ml round bottom flask equipped with a magnetic stir bar and reflux condensor. Methanol (10 ml) was then added to this flask while stirring under nitrogen and piperazine-1-carboxyaldehyde (1.37 g, 12.0 mmoles) was added while stirring was continued. The resultant transparent solution was heated to reflux overnight under nitrogen. This solution was then allowed to cool to room temperature and poured into distilled $H_2O$. Then this mixture was concentrated in vacuo until only the $H_2O$ remained. An additional 50–75 ml $H_2O$ was added and the solution was allowed to cool to 0° C. The solid was then filtered and washed with ice cold water. This material was then redissolved in EtOH and precipitated with 10 N HCl. After filtration of the suspension, the resultant solid was recrystallized from hot ethanol upon cooling to 0° C. for 15 minutes. A second crop was also collected from the second filtrate upon standing and by precipitation with EtOH from the first filtrate. These solids were then combined and the diamine amine product was obtained after high vacuum overnight. Material was then carried through to the next step of hydrolysis.

The amine residue from above was dissolved in 10.0 ml methanol and 15 ml of 4N HCl was added. The mixture was refluxed for 2 hours and allowed to cool. Ethanol was added to this solution and resulting precipitate was filtered and washed with a minimal mount of cold ethanol. The filtrate was reconcentrated and fresh ethanol and-concentrated aqueous HCl was added. This resulting precipitate was also filtered. Next, this filtrate was concentrated to near dryness and $Et_2O$ was added and the solid filtered off. The last remaining unfilterable residue was then dissolved in concentrated HCl and precipitated with EtOH. This material was filtered and washed with ethanol, combined all solid materials from the above sequence and subjected this material to high vacuum overnight to obtain the of the high affinity fluorescent DNA stain phenathridium amine derivative 27. Mass Spec. $C_{32}H_{44}N_7$(FAB+) Calc. 526, Ohs: 526.

The structural formula of compound 27 is shown in FIG. 16.

EXAMPLE 13

Synthesis Of Compounds 28a–42a And Their Related Compounds

The reaction scheme for the general synthesis of compounds 28a–42a, and their respective precursors, is given in FIG. 17.

Generally, compound 22 (0.0081 moles) is added to a 250 ml round bottom flask equipped with a magnetic stir bar and reflux condenser. Methanol (150 ml) is then added to this flask while stirring under nitrogen and an appropriate amine (0.283 moles) is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product, depending on the amine used to carry out the reaction, is obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Listed below are the products that can be obtained from their corresponding starting amines.

4-amino-1-benzylpiperidine to yield compound 28a spermine to yield compound 29a pyridine to yield compound 30a 2-(2-Aminoethyl)-1-methylpyrrolidine to yield compound 31a 1-(2-Aminoethyl)pyrrolidine to yield compound 32a 1-(2-Aminoethyl)piperidine to yield compound 33a 2-(2-Aminoethyl)pyridine to yield compound 34a 1-(2-Aminoethyl)piperazine to yield compound 35a 4-(2-Aminoethyl)morpholine to yield compound 36a 1-Amino4-(2-hydroxyethyl)piperazine to yield 37a 4-(Aminomethyl)piperidine to yield 38a 2-(Aminomethyl)pyridine to yield 39a aniline to yield 40a 1-(3-Aminopropyl)imidazole to yield 41a 4-(3-Aminopropyl)morpholine to yield 42a Synthesis and purification of the final products 28b–42b, depending on the starting amide used, 28a–42a, can be accomplished by the following general procedure. The appropriate amide (0.0036 moles) is dissolved in 75.0 ml methanol and 75 ml of 4N HCl is added. The mixture is refluxed for 2 hours and allowed to cool. Ethanol is added to this solution and resulting precipitate is filtered and washed with a minimal amount of cold ethanol. The filtrate is reconcentrated and fresh ethanol and concentrated aqueous HCl is added. This resulting precipitate is also filtered. Next, this filtrate is concentrated to near dryness and $Et_2O$ is added and the solid filtered off. The last remaining unfilterable residue is then dissolved in concentrated HCl and precipitated with EtOH. This material is filtered and washed with Ethanol. All solid materials are combined from the above sequence and is subjected to high vacuum overnight to obtain the high affinity fluorescent DNA stain 1b–15b, depending on the amine used as described above. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Listed below are the products that can be obtained from their corresponding starting amides.

amide 28a to yield product 28b amide 29a to yield product 29b amide 30a to yield product 30b amide 31a to yield product 31b amide 32a to yield product 32b amide 33a to yield product 33b amide 34a to yield product 34b amide 35a to yield product 35b amide 36a to yield product 36b amide 37a to yield product 37b amide 38a to yield product 38b amide 39a to yield product 39b amide 40a to yield product 40b amide 41a to yield product 41b amide 42a to yield product 42b

EXAMPLE 14

Synthesis Of Compound 50 And Its Related Compounds

Figure 18:
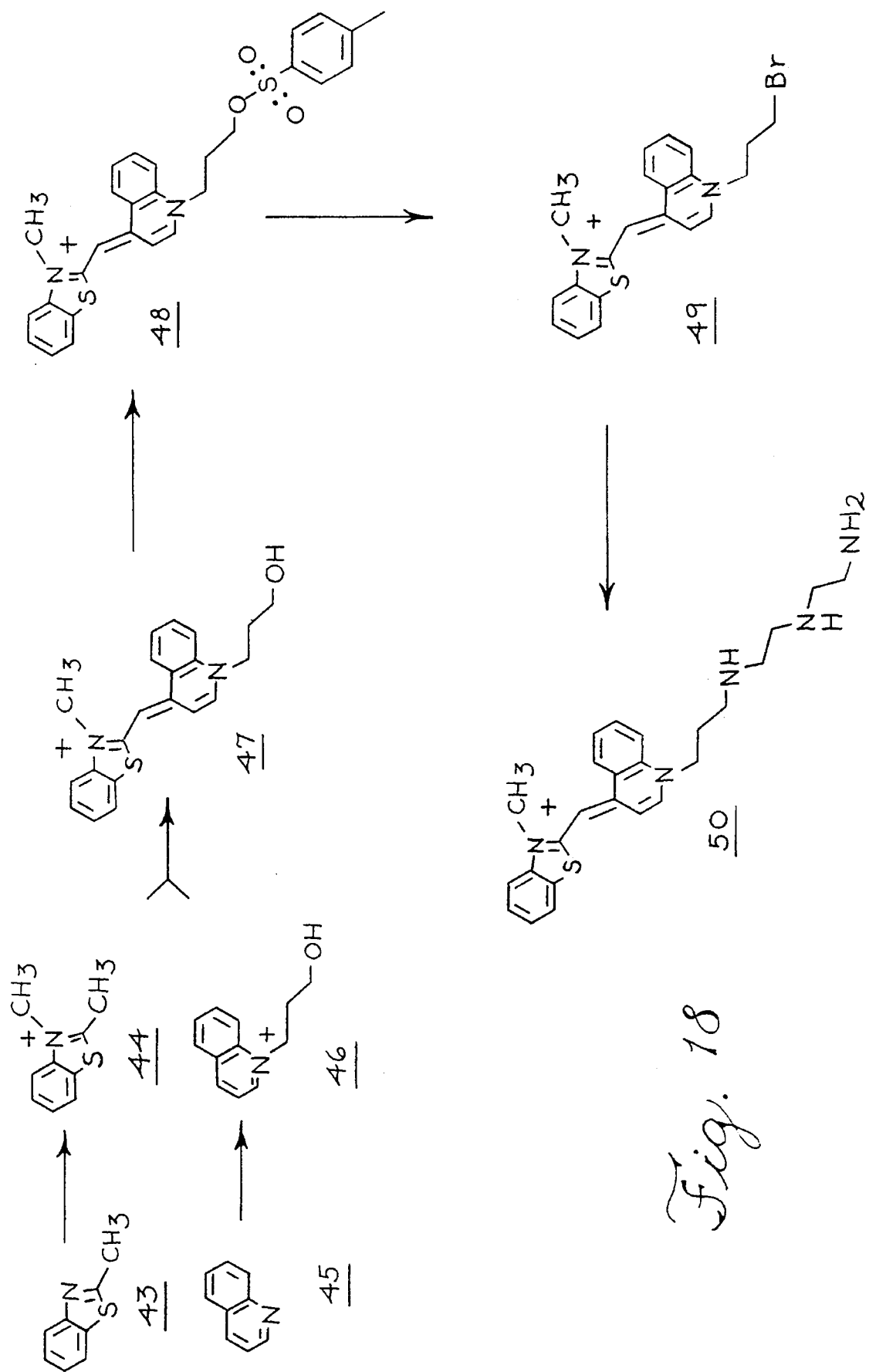
FIG. 18 is a reaction scheme for the synthesis of compound 50 and its precursors.

The reaction scheme for the general synthesis of compound 50 and its precursors is given in FIG. 18.

2-Methylbenzathiazole 43, from the Aldrich Chemical Company (Milwaukee, Wis.), is alkylated to produce compound 44 using methyl iodide by adapting procedures such as found in P. L. Southwick and A. S. Waggoner et al., U.S. Pat. No. 4,981,977, Jan. 1, 1991, or in Ernst et al., *Cytometry*, 10, 1989, pp. 3–10. Compound 45 is obtained from the Aldrich Chemical Company and is reacted with 3-bromo-1-propanol (also available from the Aldrich Chemical Company) adapting procedures of Gaugain, et. al, *Biochemistry*, Vol. 17, No. 24, 1978, pp. 5071–5078. The condensation of compound 44 and 46 is effected by adapting procedures found in Hamer, Francis, "Heterocyclic Compounds, Cyanine Dyes and Related Compounds", Wiley, 1964, pg. 37 to yield compound 47. Compound 48 can then be obtained by converting the alcohol to the tosylate by using procedures such as found in Wiberg, K. et at., *J. Am. Chem. Soc.* 92 (3), 1970, pp. 553–564. The tosylate 48 is then converted to the bromide via a nucleophilic displacement reaction with sodium bromide as per Wilt, J., *J. Org, Chem.*, 35 (8), 1970, pp.2803–2806 to yield compound 49. Alternatively, a one step procedure is provided in Hooz, J. et al., *Can. J. Chem.*, 46, 1968, pp. 86–87. Compound 49 can then be reacted with diethylene triamine (available from the Aldrich Chemical Company) as per the following procedure.

Compound 49 (0.0081 moles) is added to a 250 ml round bottom flask equipped with a magnetic stir bar and reflux condenser. Methanol (150 ml) is then added to this flask while stirring under nitrogen and the diethylene triamine (0.283 moles), which is available from the Aldrich Chemical Company is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product 50 is obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Amine derivatives of compound 49 can be synthesized as follows. Compound 49 (0.0081 moles) is added to a 250 ml round bottom flask equipped with a magnetic stir bar and reflux condensor. Methanol (150 ml) is then added to this flask while stirring under nitrogen and the appropriate amine selected from the following list (0.283 moles), which are available from the Aldrich Chemical Company, is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product 49a–49o can be obtained and is subjected to high vacuum overnight.

Listed below are the products that can be obtained from their corresponding amines.

4-amino-1-benzylpiperidine to yield 49a sperminc to yield to yield 49b pyridine to yield to yield 49c 2-(2-Aminoethyl)-1-methylpyrrolidine to yield 49d 1-(2-Aminoethyl)pyrrolidine to yield 49e 1-(2-Aminoethyl)piperidine to yield 49f 2-(2-Aminoethyl)pyridine to yield 49g 1-(2-Aminoethyl)piperazine to yield 49h 4-(2-Aminoethyl)morpholine to yield 49i 1-Amino4-(2-hydroxyethyl)piperazine to yield 49j 4-(Aminomethyl)piperidine to yield 49k 2-(Aminomethyl)pyridine to yield 49l aniline to yield 49m 1-(3-Aminopropyl)imidazole to yield 49n 4-(3-Aminopropyl)morpholine to yield 49o Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Since-the structures of compounds 49a–49o are unambiguous from the above generic procedures, there structures are not given.

EXAMPLE 15

Synthesis Of Compounds 55 And 55a–55b

Figure 19:
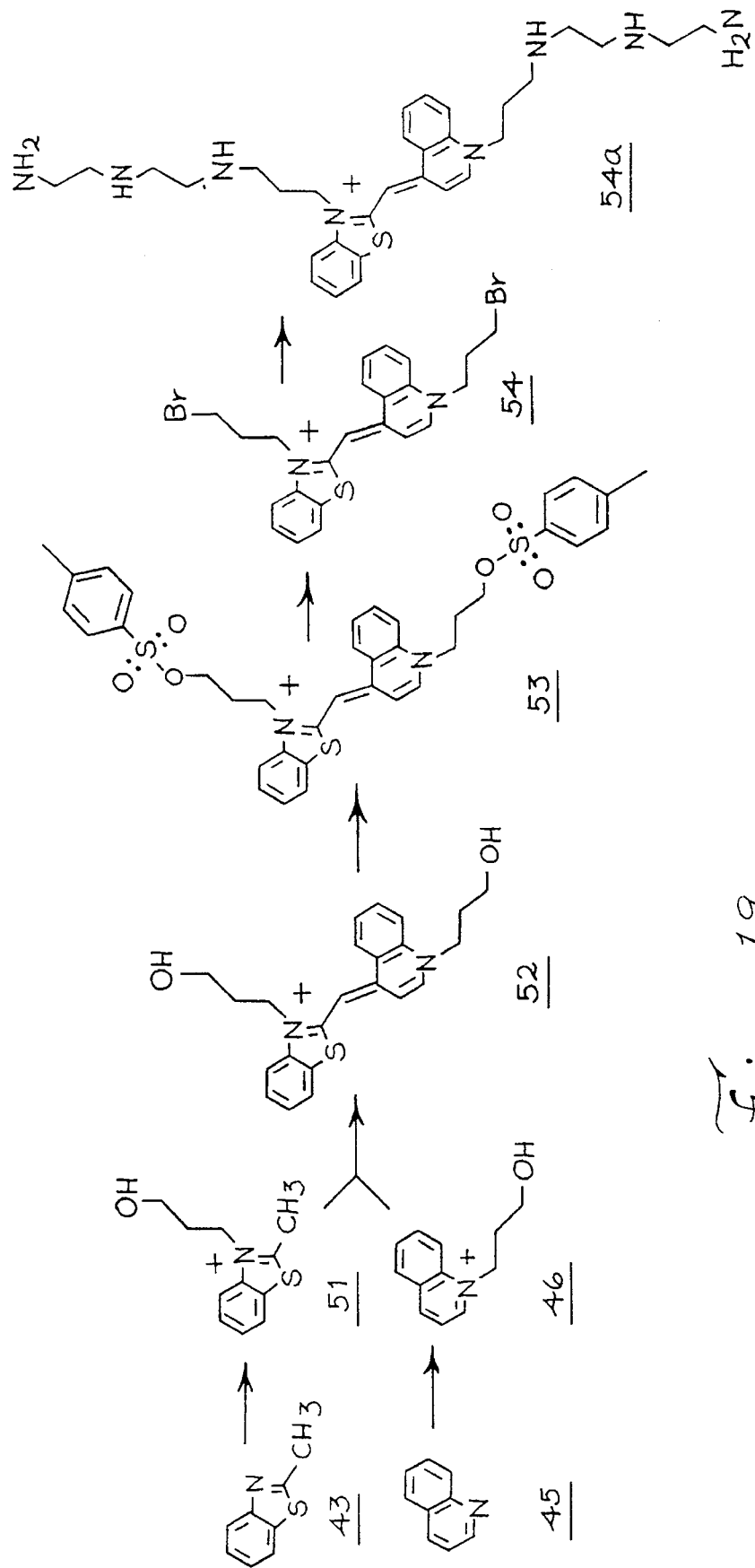
FIG. 19 is a reaction scheme for the synthesis of compounds 55, 55a, and their precursors.
Figure 20:
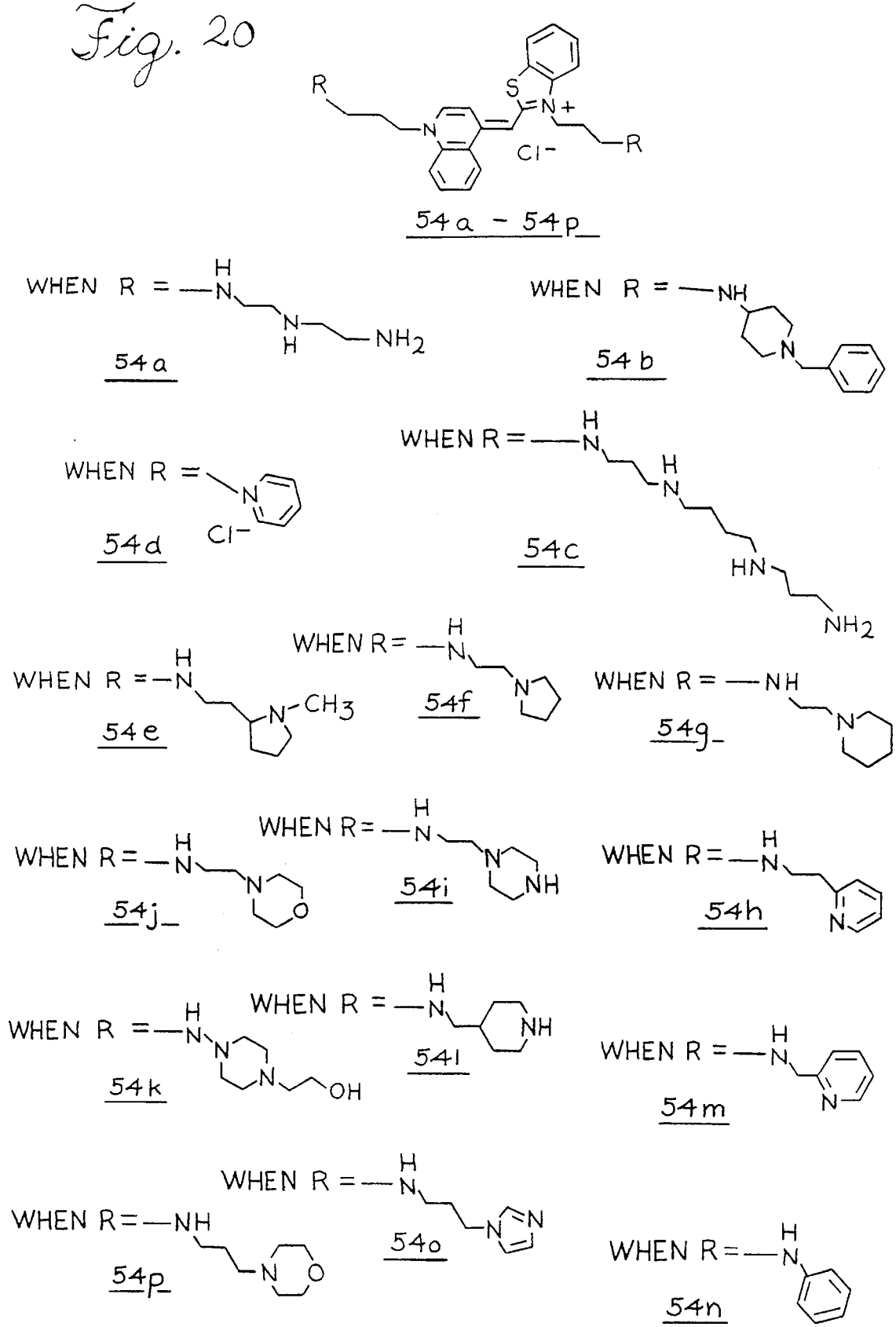
FIG. 20 shows the structural formula of compounds 55a–55p.

The reaction scheme for the general synthesis of compounds 55, 55a, and their precursors, is given in FIG. 19. The structural formula of compounds 55a–55p are given in FIG. 20.

2-Methylbenzathiazole, 43, is obtained from the Aldrich Chemical Company (Milwaukee, Wis.). It is alkylated to produce compound 51 using 3-bromo 1-propanol adapting procedures such as found in Gaugain et al., *Biochemistry*, 17 (24), 1978, 5071–5078. Compound 45 is obtained from the Aldrich Chemical Company and is reacted with 3-bromo-1-propanol (also available from the Aldrich Chemical Company) by also adapting procedures such as found in Gaugain et al., Biochemistry 17 (24) 1978, 5071–5078. The condensation of compound 51 and 52 is effected by adapting procedures found in Hamer, Francis, "Heterocyclic Compounds, Cyanine Dyes and Related Compounds", Wiley, 1964, pg. 37 to yield compound 52. Compound 53 is then obtained by converting the alcohol to the tosylate by using procedures such as found in Wiberg, K. et al., *J. Am. Chem.*

*Soc.*, 92 (3), 1970, pp. 553–564. The tosylate 53 is then converted to the bromide via a nucleophilic displacement reaction with sodium bromide as per Wilt, J., *J. Org. Chem.*, 35 (8), 1970, pp. 2803–2806 to yield compound 54.

Alternatively, a one step procedure is provided in Hooz, J. et al., *Can. J. Chem.*, 46, 1968, pp. 86–87.

Compound 54 can then be reacted with diethylene triamine or other appropriate amine from the following list (available from the Aldrich Chemical Company) to yield compounds 54a–54p in accordance with the following procedure.

Compound 54 (0.0081 moles) is added to a 250 ml round bottom flask equipped with a magnetic stir bar and reflux condenser. Methanol (150 ml) is then added to the flask while stirring under nitrogen and the diethylene triamine or other appropriate base (0.283 moles), available from the Aldrich Chemical Company, is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product 9a–p is obtained and is subjected to high vacuum overnight. Characterization can be effected by calculating the molecular mass of the free base amine from the exact isotopic mass formulas well known to those skilled in the an and comparing the resultant mass with that obtained by a high resolution mass speetrometry molecular weight determination such as are well known to those skilled in the art.

As long as the ratios of reagents and solvents are held constant, one can scale up or down the amounts of reagents using the method of ratio and proportions well known to those skilled in the art.

Listed below are the products that can be obtained from their corresponding starting amines.

diethylene triamine to yield compound 54a
4-amino-1-benzylpiperidine to yield compound 54b
sperminc to yield compound 54c
pyridine to yield compound 54d
2-(2-Aminoethyl)-1-methylpyrrolidine to yield compound 54e
1-(2-Aminoethyl)pyrrolidine to yield compound 54f
1-(2-Aminoethyl)piperidine to yield compound 54g
2-(2-Aminoethyl)pyridine to yield compound 54h
1-(2-Aminoethyl)piperazine to yield compound 54i
4-(2-Aminoethyl)morpholine to yield compound 54j
1-Amino4-(2-hydroxyethyl)piperazine to yield compound 54k
4-(Aminomethyl)piperidine to yield 54l
2-(Aminomethyl)pyridine to yield compound 54m
aniline to yield 54n
1-(3-Aminopropyl)imidazole to yield 54o
4-(3-Aminopropyl)morpholine to yield 54p

EXAMPLE 16

Synthesis Of Compounds 58 And 58a–58p

Figure 21:
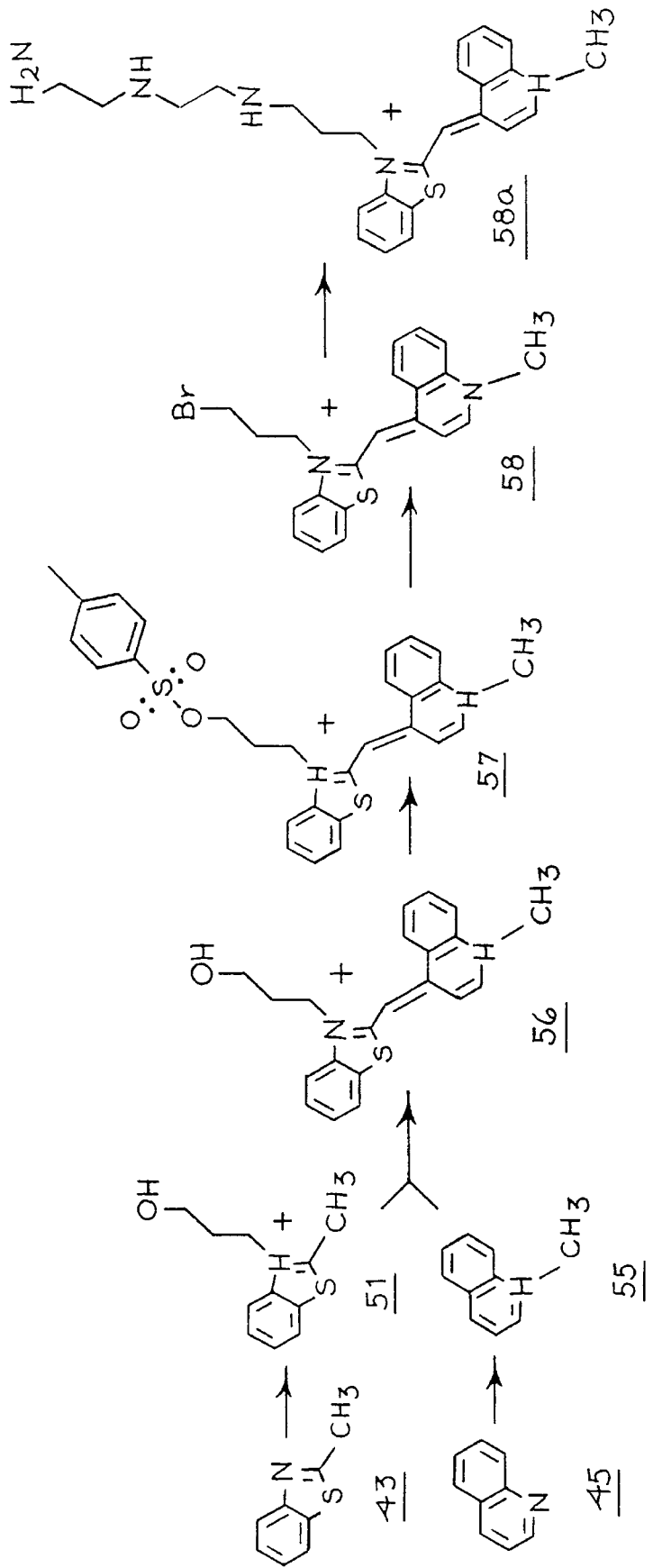
FIG. 21 is a reaction scheme for the synthesis of compounds 58, 58a, and their precursors.
Figure 22:
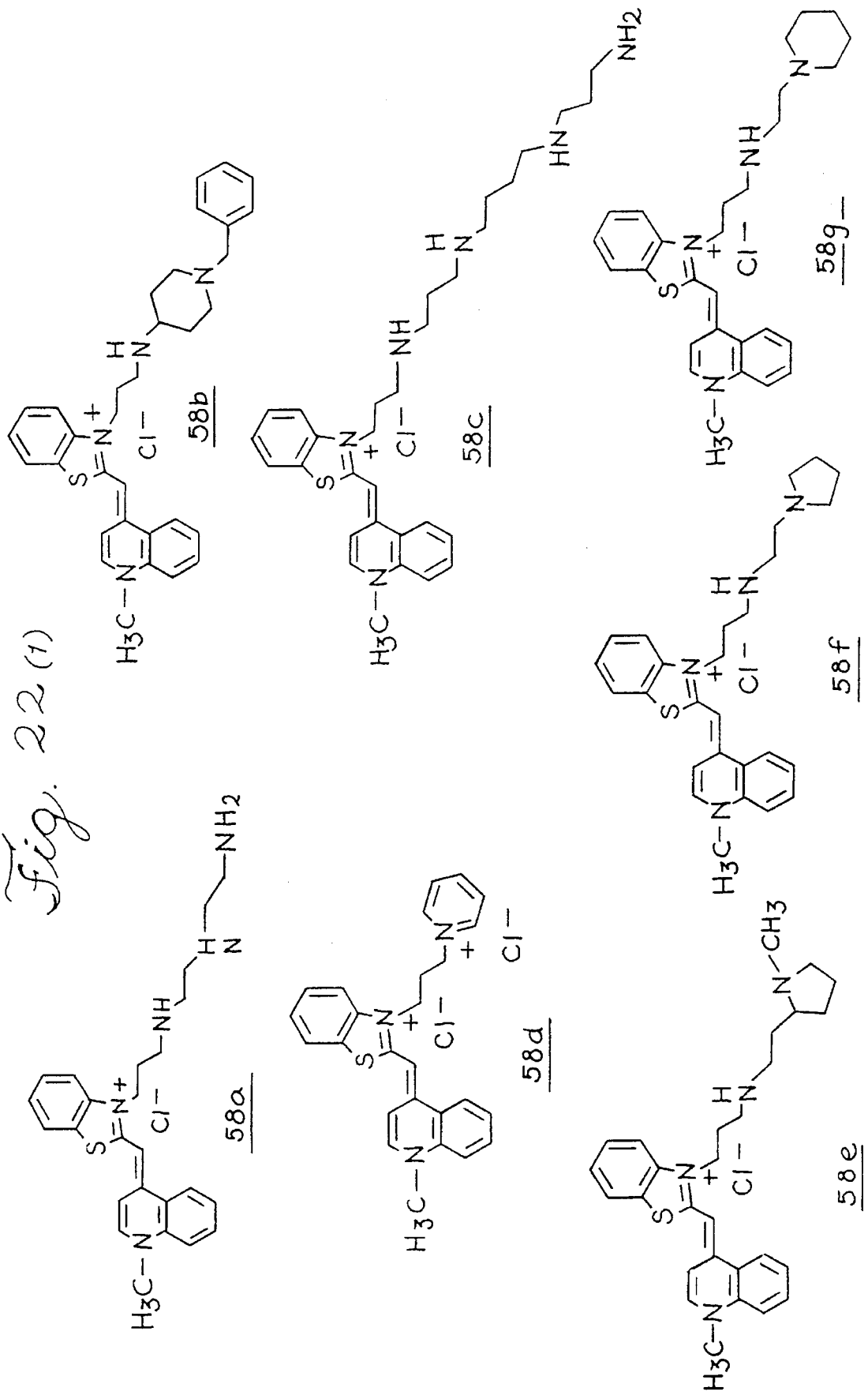
FIG. 22 shows the structural formula of compounds 58a–58p.

The reaction scheme for the general synthesis of compounds 58, 58a and their precursors, is given in FIG. 21. The structural formula of compounds 58a–58p are given in FIG. 22.

2-Methylbenzathiazole 43 is obtained from the Aldrich Chemical Company (Milwaukee, Wis.). It is alkylated to produce compound 51 using 3-bromo-1-propanol by adapting procedures Gaugain, et. al, *Biochemistry*, Vol. 17, No. 24, 1978, pp. 5071 . 5078. Compound 45 is obtained from the Aldrich Chemical Company and is reacted with methyl iodide (also available from the Aldrich Chemical Company) to yield compound 55 using procedures such as found in Southwick et al. U.S. Pat. No. 4,981,977, Jan. 1, 1991, or in Ernst et al., *Cytometry*, 10, 1989, pp. 3–10. The condensation of compound 51 and 55 is effected by adapting procedures found in Hamer, Francis, "Heterocyclic Compounds, Cyanine Dyes and Related Compounds", Wiley, 1964, pg. 37 to yield compound 56. Compound 57 is then obtained by converting the alcohol to the tosylate by using procedures such as found in Wiberg, K. et al., *J. Am. Chem. Soc.*, 92 (3), 1970, pp. 553–564. The tosylate 57 is then converted to the bromide via a nucleophilic displacement reaction with sodium bromide described by Wilt, J., *J. Org. Chem.*, 35 (8), 1970, pp. 2803–2806 to yield compound 58.

Alternatively, a one step procedure can be used as provided in Hooz, J. et al., *Can. J. Chem,*, 46, 1968, pp. 86–87.

Compound 58 can then be reacted with diethylene triamine or other appropriate amine (available from the Aldrich Chemical Company) as follows.

Compound 58 (0.0081 moles) is added to a 250 ml round bottom flask equipped with a magnetic stir bar and reflux condenser. Methanol (150 ml) is then added to this flask while stirring under nitrogen and the diethylene triamine or other appropriate amine (0.283 moles), which is available from the Aldrich Chemical Company is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product 58a–58p is obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

As long as the ratios of reagents and solvents are held constant, one can scale up or down the amounts of reagents using the method of ratio and proportions well known to those skilled in the art.

Listed below are the products that can be obtained from their corresponding amines.

diethylene triamine to yield compound 58a
4-amino-1-benzylpiperidine to yield compound 58b
spermine to yield compound 58c
pyridine to yield compound 58d
2-(2-Aminoethyl)-1-methylpyrrolidine to yield compound 58e 1-(2-Aminoethyl)pyrrolidine to yield compound 58f 1-(2-Aminoethyl)piperidine to yield compound 58g 2-(2-Aminoethyl)pyridine to yield compound 58h 1-(2-Aminoethyl)piperazine to yield compound 58i 4-(2-Aminoethyl)morpholine to yield compound 58j 1-Amino4-(2-hydroxyethyl)piperazine to yield 58k 4-(Aminomethyl)piperidine to yield 58l 2-(Aminomethyl)pyridine to yield 58m aniline to yield 58n 1-(3-Aminopropyl)imidazole to yield 58o 4-(3-Aminopropyl)morpholine to yield 58p

EXAMPLE 17

Synthesis Of Compound 64 And Its Related Compounds

Figure 23:
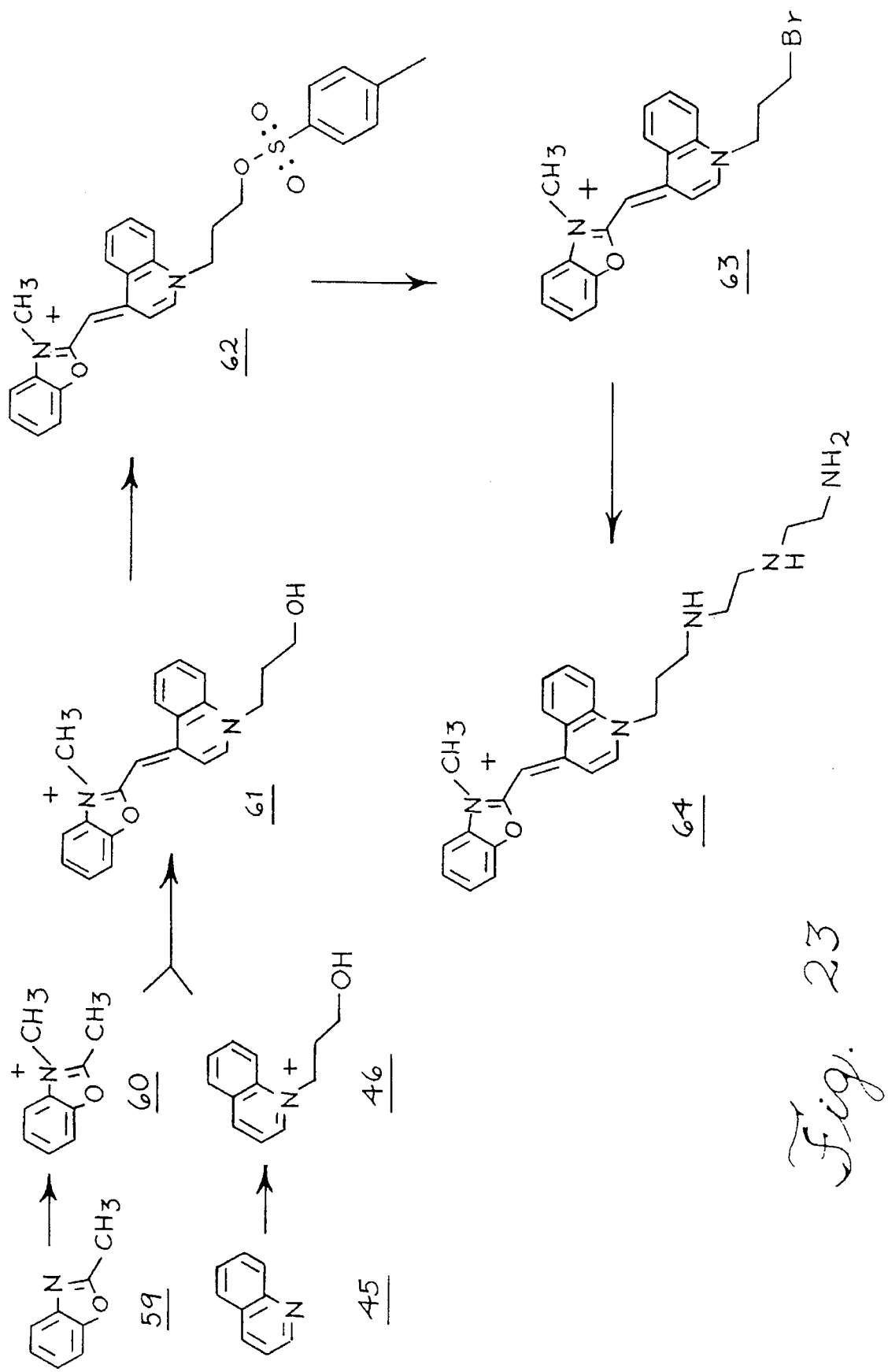
FIG. 23 is a reaction scheme for the synthesis of compound 64 and its precursors.

The reaction scheme for the general synthesis of compound 64 and its precursors is given in FIG. 23.

2-Methylbenzoxazole, 59, is obtained from the Aldrich Chemical Company (Milwaukee, Wis.). It is alkylated to produce compound 60 using methyl iodide by adapting procedures such as found in Southwick et al. U.S. Pat. No. 4,981,977, Jan. 1, 1991 or in Ernst et al., *Cytometry*, 10, 1989, pp. 3–10. Compound 45 is obtained from the Aldrich Chemical Company and is reacted with 3-bromo-1-propanol (also available from the Aldrich Chemical Company) by adapting procedures Gaugain, et. al, *Biochemistry*, Vol. 17, No. 24, 1978, pp. 5071–5078. The condensation of compound 60 and 46 is effected by adapting procedures found in Hamer, Francis, "Heterocyclic Compounds, Cyanine Dyes and Related Compounds", Wiley, 1964, pg. 37 to yield compound 61. Compound 62 can then be obtained by converting the alcohol to the tosylate by using procedures such as found in Wiberg, K. et at., *J. Am. Chem. Soc.*, 92 (3), 1970, pp. 553–564. The tosylate 62 is then convened to the bromide via a nucleophilic displacement reaction with sodium bromide as described by Wilt, J., *J. Org. Chem.*, 35 (8), 1970, pp. 2803–2806 to yield compound 63.

Alternatively, a one step procedure is provided in Hooz, J. et al., *Can. J. Chem.*, 46, 1968, pp. 86–87.

Compound 63 can then be reacted with diethylene triamine (available from the Aldrich Chemical Company) by the following procedure.

Compound 63 (0.0081 moles) is added to a 250 ml round bottom flask equipped with a magnetic stir bar and reflux condenser. Methanol (150 ml) is then added to this flask while stirring under nitrogen and the diethylene triamine (0.283 moles), which is available from the Aldrich Chemical Company is added while stirring is continued. The resultant solution is heated to reflux overnight under nitrogen. This solution is then allowed to cool to room temperature and is poured onto distilled H$_2$O. Then, this mixture is concentrated in vacuo until only the H$_2$O remains. An additional 50–75 ml H$_2$O is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product 64 is obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Amine derivatives of compound 63 can be synthesized as follows. Compound 63 (0.0081 moles) is added to a 250 ml round bottom flask equipped with a magnetic stir bar and reflux condenser. Methanol (150 ml) is then added to this flask while stirring under nitrogen and the appropriate amine selected from the following list (0.283 moles), which are available from the Aldrich Chemical Company, is added while stirring is continued. The resultant solution is heated to reflux overnight under nitrogen. This solution is then allowed to cool to room temperature and is poured onto distilled H$_2$O. Then, this mixture is concentrated in vacuo until only the H$_2$O remains. An additional 50–75 ml H$_2$O is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product 30a–30o is obtained and is subjected to high vacuum overnight.

Listed below are the compounds that can be obtained from their corresponding amines.

4-amino-1-benzylpiperidine to yield 63a spermine to yield to yield 63b pyridine to yield to yield 63c 2-(2-Aminoethyl)-1-methylpyrrolidine to yield 63d 1-(2-Aminoethyl)pyrrolidine to yield 63e 1-(2-Aminoethyl)piperidine to yield 63f 2-(2-Aminoethyl)pyridine to yield 63g 1-(2-Aminoethyl)piperazine to yield 63h 4-(2-Aminoethyl)morpholine to yield 63i 1-Amino4-(2-hydroxyethyl)piperazine to yield 63j 4-(Aminomethyl)piperidine to yield 63k 2-(Aminomethyl)pyridine to yield 63l aniline to yield 63m 1-(3-Aminopropyl)imidazole to yield 63n 4-(3-Aminopropyl)morpholine to yield 63o Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art. Note that no hydrolysis is necessary.

Since the structures of compounds 63a–63o are unambiguous from the above generic procedures, their structures are not shown.

EXAMPLE 18

Synthesis Of Compounds 68 And 68a–68p

Figure 24:
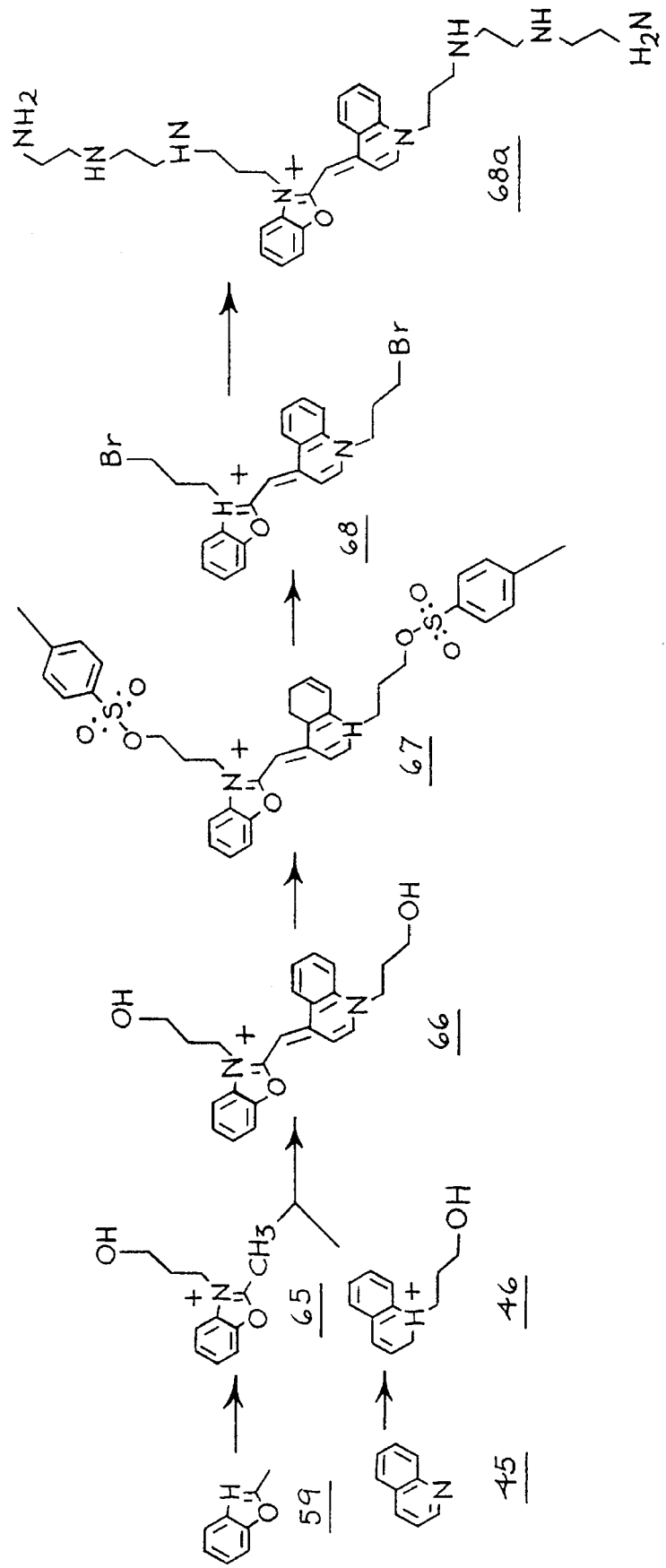
FIG. 24 is a reaction scheme for the synthesis of compounds 68, 68a, and their precursors.
Figure 25:
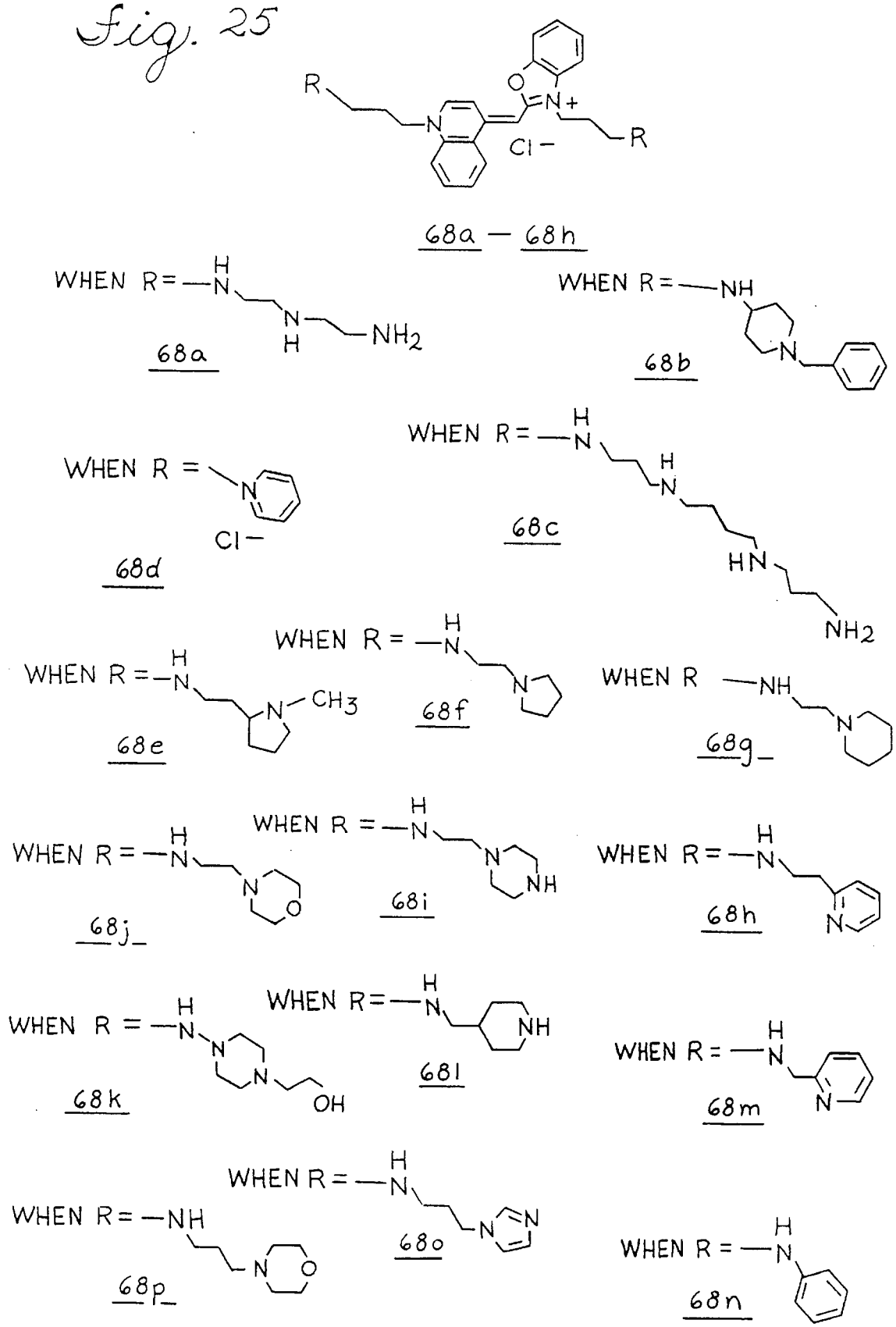
FIG. 25 shows the structural formula of compounds 68a–68p.

The reaction scheme for the general synthesis of compounds 6 8, 68a, and their precursors, is given in FIG. 24. The structure formula of compounds 68a–68p are given in FIG. 25.

2-Methylbenzoxazole 59 is obtained from the Aldrich Chemical Company (Milwaukee, Wis.). It is alkylated to produce compound 65 using 3-brom-1-propanol by adapting procedures of Gaugain et al., *Biochemistry*, 17 (24), 1978, pp. 5071–5078. Compound 45 is obtained from the Aldrich Chemical Company and is reacted with 3-bromo-1-propanol (also available from the Aldrich Chemical Company) using procedures such as found in Gaugain et al., *Biochemistry*, 17 (24) 1978, 5071–5078. The condensation of compound 65 and 46 is effected by adapting procedures found in Hamer, Francis, "Heterocyclic Compounds, Cyanine Dyes and Related Compounds", Wiley, 1964, p. 37 to yield compound 60. Compound 67 is then obtained by converting the alcohol to the tosylate by using procedures such as found in Wiberg, K. et al., *J. Am. Chem. Soc.*, 92 (3), 1970, pp. 553–564. The tosylate 67 is then converted to the bromide via a nucleophilic displacement reaction with sodium bromide as per Wilt, J., *J. Org. Chem.*, 35 (8), 1970, pp. 2803–2806 to yield compound 68.

Alternatively, a one step procedure, as provided by Hooz, J. et al., *Can. J. Chem.*, 46, 1968, pp. 86–87, can be used.

Compound 68 can then be reacted with diethylene triamine or other appropriate amine (available from the Aldrich Chemical Company) by the following procedure.

Compound 68 (0.0081 moles) is added to a 250 ml round bottom flask equipped with a magnetic stir bar and reflux condenser. Methanol (150 ml) is then added to this flask while stirring under nitrogen and an amine, such as diethylene triamine or other appropriate base (0.283 moles), which is available from the Aldrich Chemical Company is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product 68a is obtained and is subjected to high vacuum overnight. Characterization is effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

As long as the ratios of reagents and solvents are held constant, one can scale up or down the amounts of reagents using the method of ratio and proportions well known to those skilled in the art.

Listed below are products that can be obtained from their corresponding amines.

diethylene triamine to yield compound 68a
4-amino-1-benzylpiperidine to yield compound 68b
spermine to yield compound 68c
pyridine to yield compound 68d
2-(2-Aminoethyl)-1-methylpyrrolidine to yield compound 68e
1-(2-Aminoethyl)pyrrolidine to yield compound 68f
1-(2-Aminoethyl)piperidine to yield compound 68g
2-(2-Aminoethyl)pyridine to yield compound 68h
1-(2-Aminoethyl)piperazine to yield compound 68i
4-(2-Aminoethyl)morpholine to yield compound 68j
1-Amino4-(2-hydroxyethyl)piperazine to yield 68k
4-(Aminomethyl)piperidine to yield 68l
2-(Aminomethyl)pyridine to yield 68m
aniline to yield 68n
1-(3-Aminopropyl)imidazole to yield 68o
4-(3-Aminopropyl)morpholine to yield 68p

EXAMPLE 19

Synthesis Of Compounds 71 And 71a–71p

Figure 26:
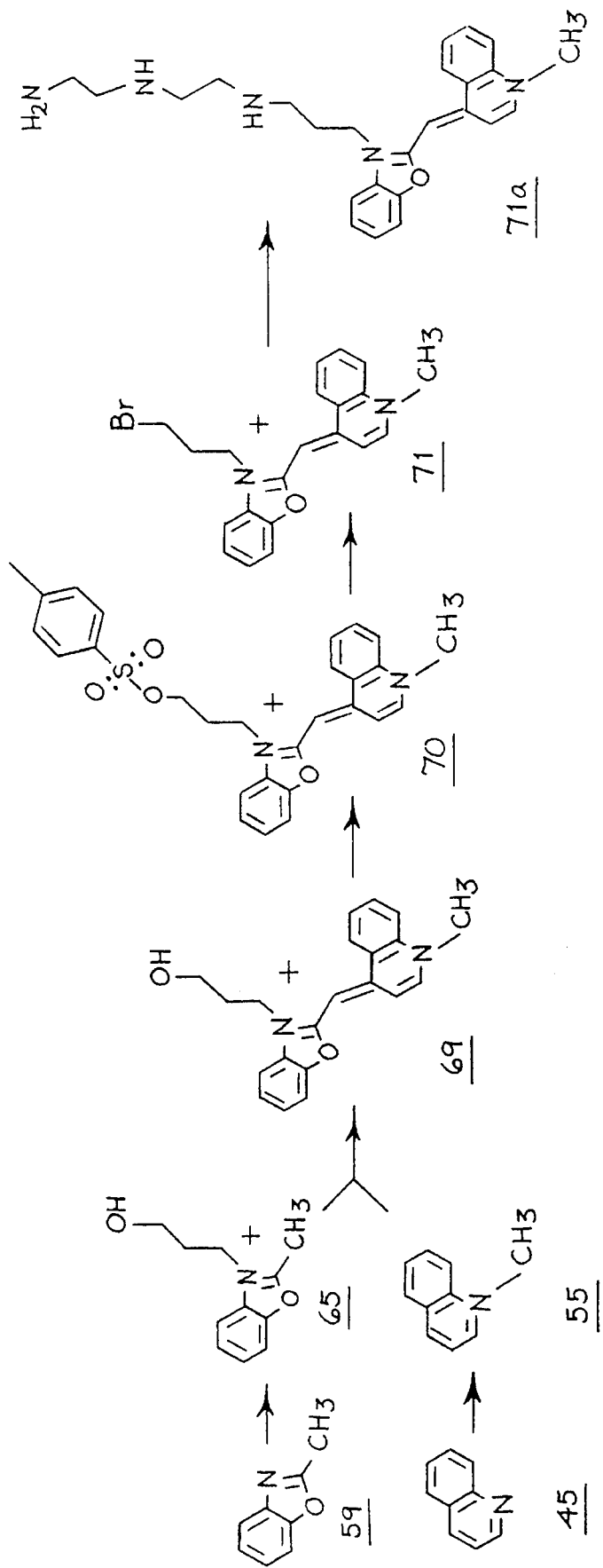
FIG. 26 is a reaction scheme for the synthesis of compounds 71, 71a, and their precursors.
Figure 27:
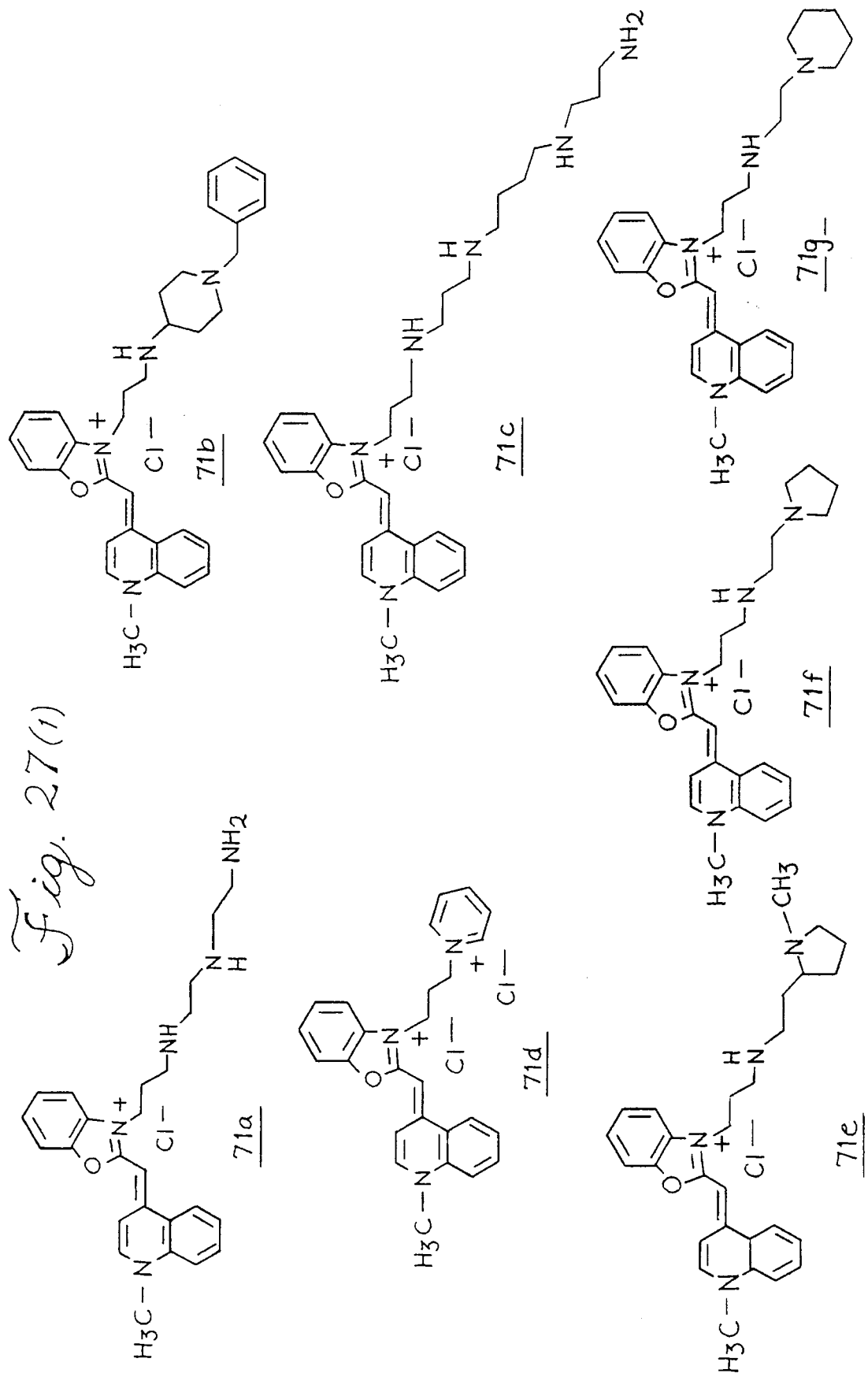
FIG. 27 shows the structural formula of compounds 71a–71p.
Figure 27:
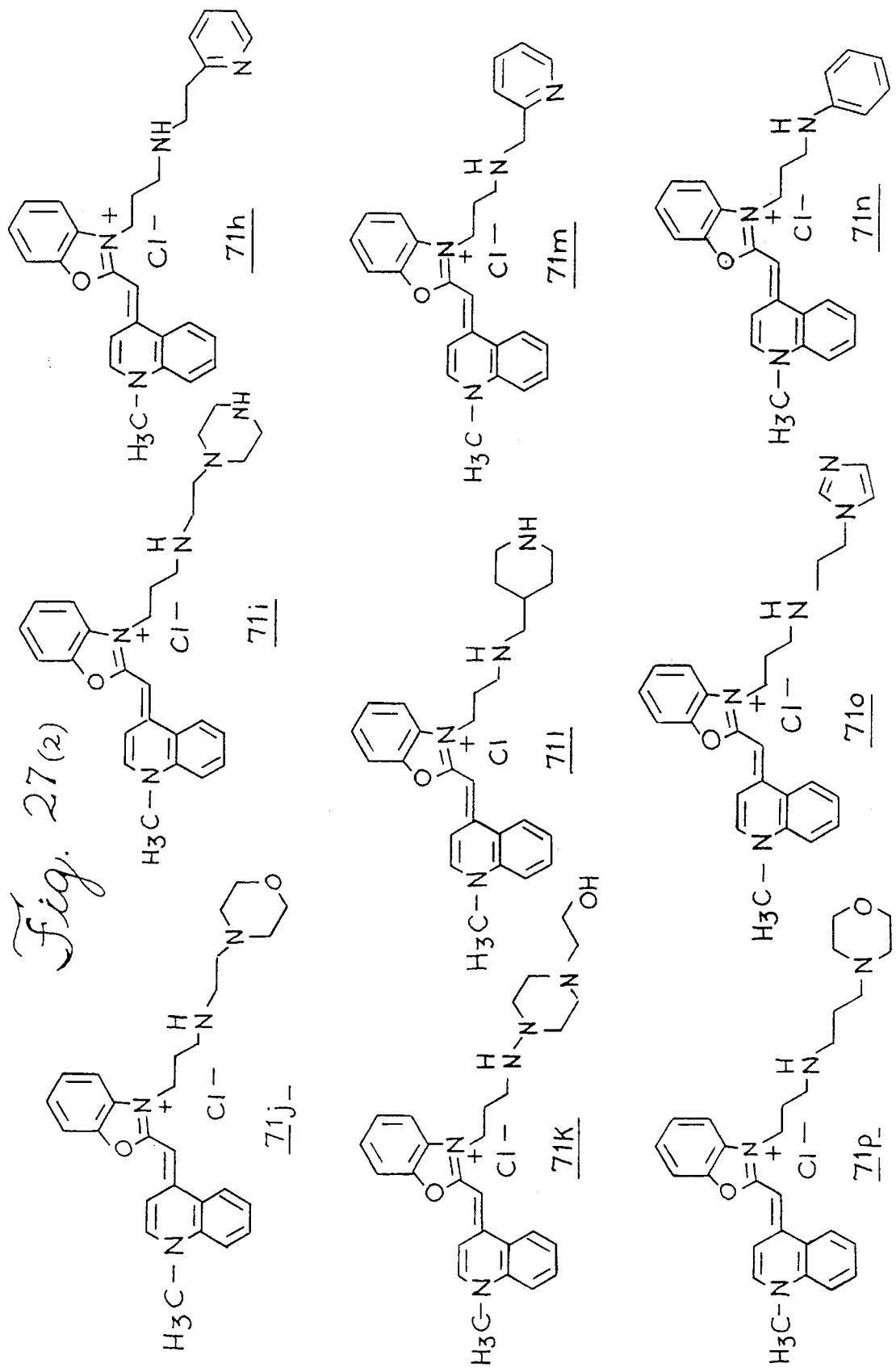

The reaction scheme for the general synthesis of compounds 71, 71a, and their precursors, is given in FIG. 26. The structure formula of compounds 71a–71p are given in FIG. 27.

2-Methylbenzoxazole 59 is obtained from the Aldrich Chemical Company (Milwaukee, Wis.). It is alkylated to produce compound 65 using 3-bromo-1-propanol by adapting procedures such as found in Gaugain, et. al, *Biochemistry*, Vol. 17, No. 24, 1978, pp. 5071–5078 to obtain compound 13. Compound 45 is obtained from the Aldrich Chemical Company and is reacted with methyl iodide (also available from the Aldrich Chemical Company) using procedures such as found in Southwick et al. U.S. Pat. No. 4,981,977, Jan. 1, 1991 or in Ernst et al., *Cytometry*, 10, 1989, pp. 3–10 to yield compound 55. The condensation of compound 65 and 55 is effected by adapting procedures found in Hamer, Francis, "Heterocyclic Compounds, Cyanine Dyes and Related Compounds", Wiley, 1964, p. 37 to yield compound 69. Compound 70 is then obtained by converting the alcohol to the tosylate by using procedures such as found in Wiberg, K. et al., *J. Am. Chem. Soc.*, 92 (3), 1970, pp. 553–564. The tosylate 70 can then be converted to the bromide via a nucleophilic displacement reaction with sodium bromide as disclosed by Wilt, J., *J. Org. Chem.*, 35 (8), 1970, pp. 2803–2806 to yield compound 20.

Alternatively, a one step procedure, as provided by Hooz, J. et al., *Can. J. Chem.*, 46, 1968, pp. 86–87, can be used. Compound 70 can then be reacted with diethylene triamine or other appropriate amine (available from the Aldrich Chemical Company) by the following procedure.

Compound 71 (0.0081 moles) is added to a 250 ml round bottom flask equipped with a magnetic stir bar and reflux condenser. Methanol (150 ml) is then added to this flask while stirring under nitrogen and diethylene triamine or other appropriate amine, (0.283 moles), which is available from the Aldrich Chemical Company is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the final product 71a–71p is obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

As long as the ratios of reagents and solvents are held constant, one can scale up or down the amounts of reagents using the method of ratio and proportions well known to those skilled in the art.

Listed below are products that can be obtained for their corresponding amines.

diethylene triamine to yield compound 20a
4-amino-1-benzylpiperidine to yield compound 20b
spermine to yield compound 20c
pyridine to yield compound 20d
2-(2-Aminoethyl)-1-methylpyrrolidine to yield compound 20e
1-(2-Aminoethyl)pyrrolidine to yield compound 20f
1-(2-Aminoethyl)piperidine to yield compound 20g
2-(2-Aminoethyl)pyridine to yield compound 20h
1-(2-Aminoethyl)piperazine to yield compound 20i
4-(2-Aminoethyl)morpholine to yield compound 20j
1-Amino4-(2-hydroxyethyl)piperazine to yield 20k
4-(Aminomethyl)piperidine to yield 20l
2-(Aminomethyl)pyridine to yield 20m
aniline to yield 20n
1-(3-Aminopropyl)imidazole to yield 20o
4-(3-Aminopropyl)morpholine to yield 20p

EXAMPLE 20

Synthesis Of Compound 80 And Its Related Compounds

Figure 28:
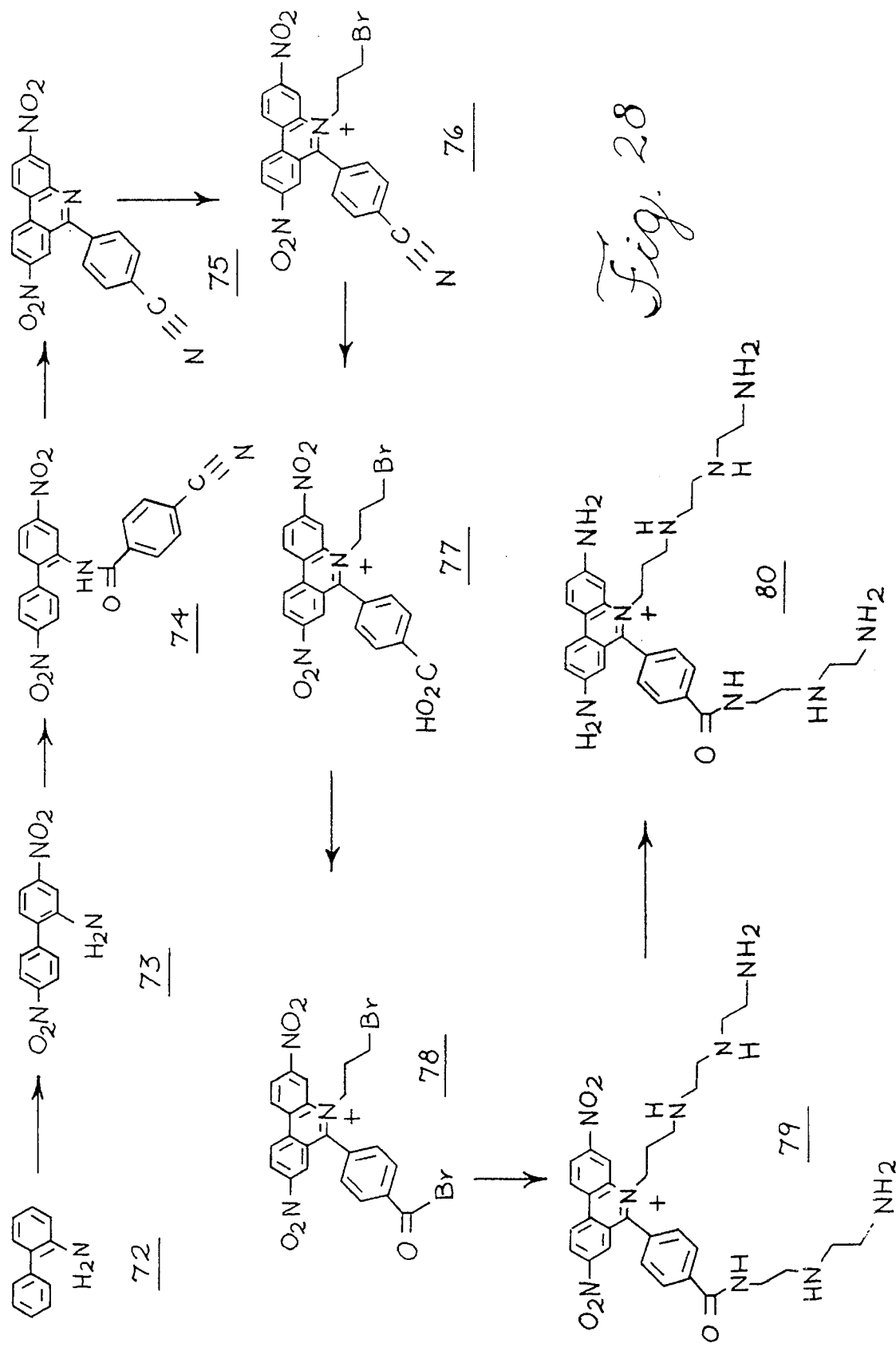
FIG. 28 is a reaction scheme for the synthesis of compound 80 and its precursors.

The reaction scheme for the general synthesis of compound 80 and its precursors is given in FIG. 28.

Compound 72 is obtained from the Aldrich Chemical Company. Compound 73 can be synthesized from compound 72, compound 74 can be synthesized from compound 73, and compound 75 can be synthesized from compound 74, each following the procedure of Dervan et al., *J. Am. Chem. Soc.*, Vol. 100, No. 6, 1978, pp. 1968–1970 or secondary references contained within.

Compound 76 is synthesized from compound 75 by the procedure of Gaugain, et. al, *Biochemistry*, Vol. 17, No. 24, 1978, pp. 5071–5078. Compound 77 can be synthesized from compound 76 by the procedure of Dervan, P. B. , Becker, M. M., *J. Am. Chem. Soc.*, 1978, Vol. 100, No. 6, 1968–1970 or secondary references contained within. Compound 78 can be synthesized from compound 77 by the procedures such as Lee et al., *J. Am. Chem. Soc.*, 88 (14), 1966, pp. 3440–3441 or references contained within. Compound 79 can be synthesized by the following procedure. Compound 78 (0.0081 moles) is added to a 250 ml round bottom flask equipped with a magnetic stir bar and reflux condenser. Methanol (150 ml) is then added to this flask while stirring under nitrogen and the diethylene triamine (0.283 moles), which is available from the Aldrich Chemical Company is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the product 79 is obtained and is subjected to high vacuum overnight. Characterization is effected by calculating the molecular mass of the free base amine from the exact isotopic mass formulas well known to those skilled in the art and comparing the resultant mass with that obtained by a high resolution mass spectrometry molecular weight determination such as are well known to those skilled in the art. The final compound 80 can be obtained by using the reduction procedure of Dervan, P. B. , Becker, M. M., *J. Am. Chem. Soc.*, 1978, 100 (6), 1968–1970. Characterization and purification of all intermediates can be accomplished using methods well known to those skilled in the art.

Amine derivatives of compound 78 can be synthesized as follows. Compound 78 (0.0081 moles) is added to a 250 ml round bottom flask equipped with a magnetic stir bar and reflux condensor. Methanol (150 ml) is then added to this flask while stirring under nitrogen and the appropriate amine selected from the following list (0.283 moles), which are available from the Aldrich Chemical Company, is added while stirring is continued. The resultant solution is heated to reflux overnight under nitrogen. This solution is then allowed to cool to room temperature and is poured onto distilled $H_2O$ Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 25 minutes. A second crop is also collected from the second filtrate upon standing and by precipitation with EtOH from the first filtrate. These solids are then combined and the product 78a–78o is obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Given below are the compounds that can be obtained from their corresponding amines.

4-amino-1-benzylpiperidine to yield 78a
spermine to yield to yield 78b
pyridine to yield to yield 78c
2-(2-Aminoethyl)-1-methylpyrrolidine to yield 78d
1-(2-Aminoethyl)pyrrolidine to yield 78e
1-(2-Aminoethyl)piperidine to yield 78f
2-(2-Aminoethyl)pyridine to yield 78g
1-(2-Aminoethyl)piperazine to yield 78h
4-(2-Aminoethyl)morpholine to yield 78i
1-Amino4-(2-hydroxyethyl)piperazine to yield 78j
4-(Aminomethyl)piperidine to yield 78k
2-(Aminomethyl)pyridine to yield 78l
aniline to yield 78m
1-(3-Aminopropyl)imidazole to yield 78n
4-(3-Aminopropyl)morpholine to yield 78o Synthesis and purification of the final product 78aa–78oo can be accomplished by the following protocol to yield the corresponding final products as shown below. The nitro compound 78a–78o can be converted to the appropriate amine using the procedure of Dervan et al., *J. Am. Chem. Soc.*, 100 (6), 1978, pp. 1968–1970.

Listed below are the products that can be obtained from their corresponding immediate precursors.

78a to yield 78aa 78b to yield to yield 78bb 78c to yield to yield 78cc 78d to yield 78dd 78e to yield 78ee 78f to yield 78ff 78g to yield 78gg 78h to yield 78hh 78i to yield 78ii 78j to yield 78jj 78k to yield 78kk 78l to yield 78ll 78m to yield 78mm 78n to yield 78nn 78o to yield 78oo Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Since the structures of compounds 78a–78o and 78aa–78oo are unambiguous from the given generic procedures, their structures are not shown.

EXAMPLE 21

Synthesis Of Compound 85 And Its Related Compounds

Figure 29:
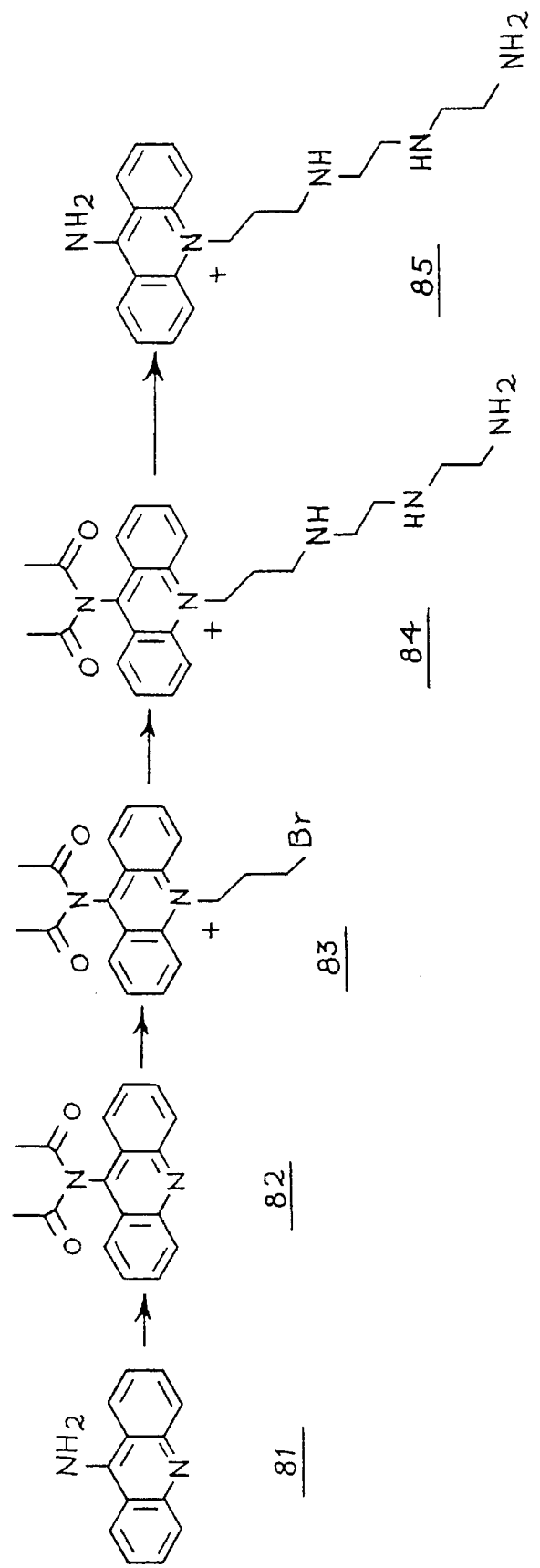
FIG. 29 is a reaction scheme for the synthesis of compound 85 and its precursors.

The reaction scheme for the general synthesis of compound 85 and its precursors is given in FIG. 29.

Starting material 81 (0.0876 moles) is obtained from the Aldrich Chemical Company (Milwaukee, Wis.) and is added to a single neck 3.0 liter round bottom flask under Argon and equipped with a magnetic stir bar and a reflux condenser. To this vessel, 1.0 liter of dry pyridine is added while stirring. Stirring of the resulting suspension is continued for 15 minutes until all the solid is dissolved. A catalytic amount of N,N-dimethylaminopyridine (1.07 g, 0.00876 moles) is added to this solution while stirring. Acetic anhydride (462 g, 4.9 moles) is then added and the resulting reaction mixture is refluxed for 8–12 hours. The reaction mixture is then allowed to cool and the solvent is removed in vacuo. For purification of the product 42, a gradient silica gel column is performed using an appropriate solvent system determined using methods well known to those skilled in the art such as Thin Layer Chromatography. Fractions of 10.0 ml are collected and appropriate fractions are recombined and the solvent is removed in vacuo. The residue is then dissolved in hot EtOH (220 ml) and precipitated by cooling to 0° C. The mother liquor is decanted off and 200 ml of fresh EtOH is added. The solid is redissolved by heating and is allowed to crystallize and −4° C. for 48 hours. Crystals are collected from both the mother liquor and the second recrystalization and are washed with a small amount of cold EtOH and dried under high vacuum for several hours. The resultant compound 82 can be characterized by high resolution mass spectrometry as well known to those skilled in the art.

Compound 83 can be synthesized from the imide 42 via a modification of a literature procedure of Gaugain, et al., *Biochemistry*, Vol. 17, No. 24, 1978, pp. 5071–5078 for quarternization of the diamide of 3,8 diamino-6-phenyl phenanthridine. Imide 82 (0.023 moles) is placed in a 2.0 liter round bottom flask under Argon and is equipped with a magnetic stir bar and reflux condenser. 1,3-Dibromopropane (1.0 liter, 9.86 moles) is added to this flask and the resultant mixture is brought to reflux for about 7 hours. The solution is cooled overnight and the precipitant is filtered and washed with EhO. This material is recrystallized from $CH_3OH$ to yield diacetyl bromide 83 which can be characterized by mass spectrometry and other methods known to those skilled in the art.

Compound 83 (0.0081 moles) is added to a 250 ml round bottom flask equipped with a magnetic stir bar and reflux condenser. Methanol (150 ml) is then added to this flask while stirring under nitrogen and the diethylene triamine (0.283 moles), which is available from the Aldrich Chemical Company is added while stirring is continued. The resultant solution is heated to reflux overnight under nitrogen. This solution is then allowed to cool to room temperature and is poured onto distilled $H_2O$ Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for about 15 minutes. A second crop is also collected from the second filtrate upon standing and by precipitation with EtOH from the first filtrate. These solids are then combined and the product 84 can be obtained and can be subjected to high vacuum overnight. Characterization can be effected by calculating the molecular mass of the free base amine from the exact isotopic mass formulas well known to those skilled in the an and comparing the resultant mass with that obtained by a high resolution mass spectrometry molecular weight determination such as are well known to those skilled in the art.

Synthesis and purification of the final product 85 can be accomplished by the following protocol. The imide (0.0036 moles) 84 is dissolved in 75.0 ml methanol and 75 ml of 4N HCl is added. The mixture is refluxed for about 2 hours and allowed to cool. Ethanol is added to this solution and resulting precipitate is filtered and washed with a minimal amount of cold ethanol. The filtrate is reconcentrated and fresh ethanol and concentrated aqueous HCl is added. This resulting precipitate is also filtered. Next, this filtrate is concentrated to near dryness and $Et_2O$ is added and the solid filtered off. The last remaining unfilterable residue is then dissolved in concentrated HCl and precipitated with EtOH. This material is filtered and washed with Ethanol. All solid materials are combined from the above sequence and is subjected to high vacuum overnight to obtain 85. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Amine derivatives of compound 83 can be synthesized as follows: Compound 83 (0.0081 moles) is added to a 250 ml round bottom flask equipped with a magnetic stir bar and reflux condenser. Methanol (150 ml) is then added to this flask while stirring under nitrogen and the appropriate amine selected from the following list (0.283 moles), which are available from the Aldrich Chemical Company, is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then reddissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the product 83a–83o can be obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Listed below are the products that can be obtained from their corresponding amines.

4-amino-1-benzylpiperidine to yield 83a spermine to yield to yield 83b pyridine to yield to yield 83c 2-(2-Aminoethyl)-1-methylpyrrolidine to yield 8d 1-(2-Aminoethyl)pyrrolidine to yield 83e 1-(2-Aminoethyl)piperidine to yield 83f 2-(2Aminoethyl)pyridine to yield 83g 1-(2-Aminoethyl)piperazine to yield 83h 4-(2-Aminoethyl)morpholine to yield 83i 1-Amino4-(2-hydroxyethyl)piperazine to yield 83j 4-(Aminomethyl)piperidine to yield 83k 2-(Aminomethyl)pyridine to yield 83l aniline to yield 83m 1-(3-Aminopropyl)imidazole to yield 83n 4-(3-Aminopropyl)morpholine to yield 83o Synthesis and purification of the final product 83aa–83oo can be accomplished by the following protocol to yield the corresponding final products as shown below. The imide (0.0036 moles) 83a–83o is dissolved in 75.0 ml methanol and 75 ml of 4N HCl is added. The mixture is refluxed for about 2 hours and allowed to cool. Ethanol is added to this solution and resulting precipitate is filtered and washed with a minimal amount of cold ethanol. The filtrate is reconcentrated and fresh ethanol and concentrated aqueous HCl is added. This resulting precipitate is also filtered. Next, this filtrate is concentrated to near dryness and $Et_2O$ is added and the solid filtered off. The last remaining unfilterable residue is then dissolved in concentrated HCl and precipitated with EtOH. This material is filtered and washed with Ethanol. All solid materials are combined from the above sequence and is subjected to high vacuum overnight to obtain 83aa–83oo. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Listed below are the products that can be obtained from their corresponding immediate starting materials.

83a to yield 83aa 83b to yield 83bb 83c to yield 83cc 83d to yield 83dd 83e to yield 83ee 83f to yield 83ff 83g to yield 83gg 83h to yield 83hh 83i to yield 83ii 83j to yield 83jj 83k to yield 83kk 83l to yield 83ll 83m to yield 83mm 83n to yield 83nn 83o to yield 83oo Since the structures of compounds 83a–83o and 83aa–83oo are unambiguous from the generic procedures, their structures are not given.

EXAMPLE 22

Synthesis Of Compound 90 And Its Related Compounds

Figure 30:
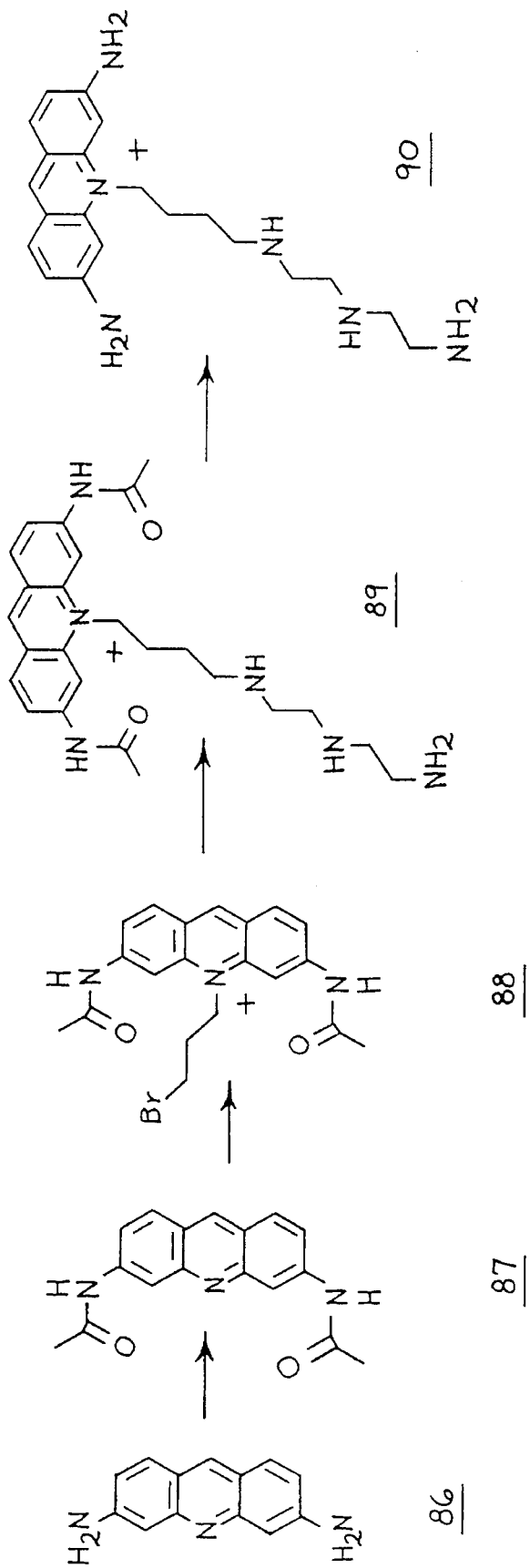
FIG. 30 is a reaction scheme for the synthesis of compound 90 and its precursors.
Figure 31:
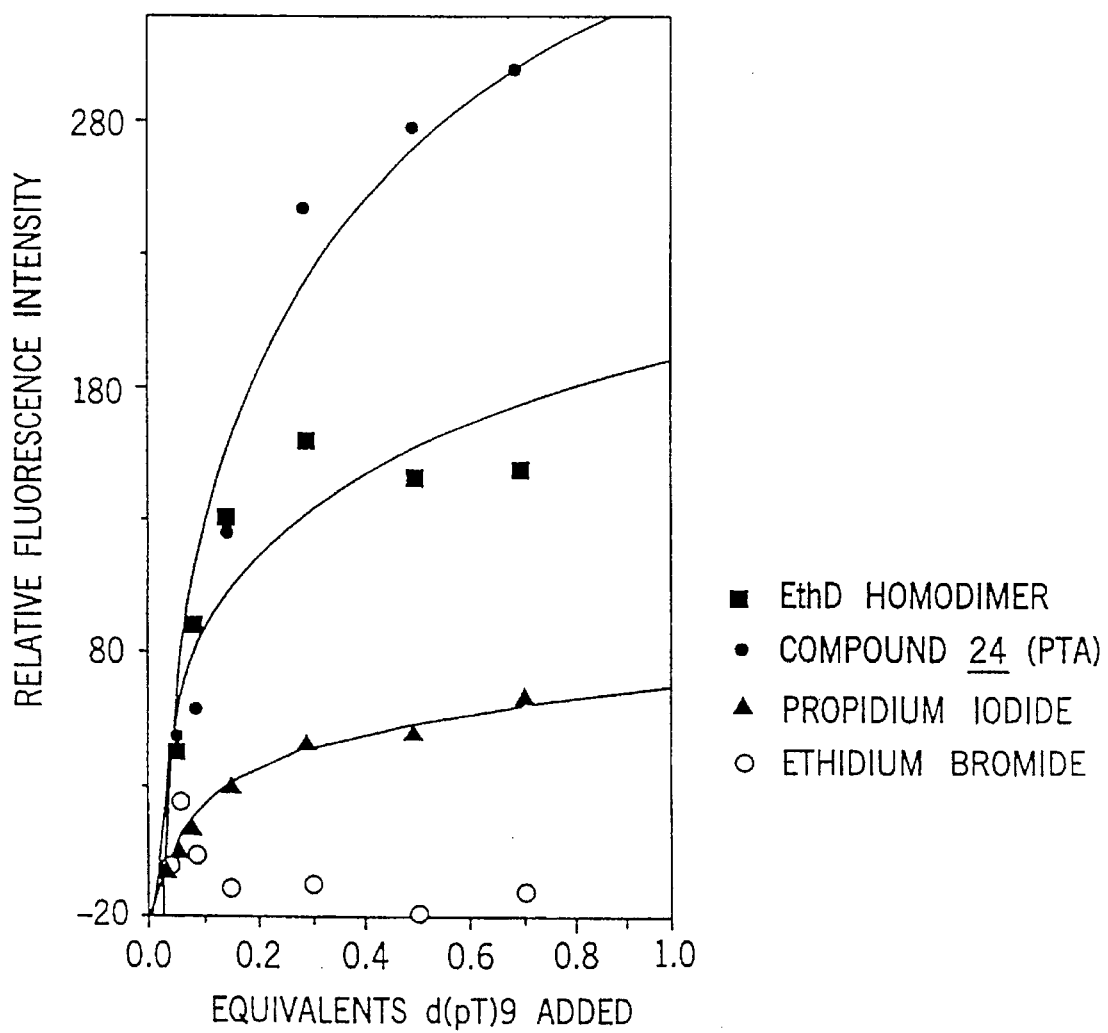
FIG. 31 is a comparison of relative fluorescence intensities obtained from staining DNA by compound 24, ethidium bromide, propidium iodide, and ethidium homodimer.

The reaction scheme for the general synthesis of compound 90 and its precursors is given in FIG. 30.

Starting material 86 (0.0876 moles) is obtained from the Aldrich Chemical Company (Milwaukee, Wis.) and is added to a single neck 3.0 liter round bottom flask under Argon and equipped with a magnetic stir bar and a reflux condenser. Acetic anhydride (462 g, 4.9 moles) is then added and the resulting reaction mixture is refluxed for 8–12 hours. The reaction mixture is then allowed to cool and the solvent is removed in vacuo. For purification of the product 87, a gradient silica gel column is performed using an appropriate solvent system determined using methods well known to those skilled in the art. Fractions of 10.0 ml are collected and appropriate fractions are recombined and the solvent is removed in vacuo. The residue is then dissolved in hot EtOH (220 ml) and precipitated by cooling to 0° C. The mother liquor is decanted off and 200 ml of fresh EtOH is added. The solid is redissolved by heating and is allowed to crystallize and −4° C. for 48 hours. Crystals are collected from both the mother liquor and the second recrystallization and are washed with a small amount of cold EtOH and dried under high vacuum for several hours. The resultant compound 87 can be characterized by high resolution mass spectrometry as well known to those skilled in the art.

Compound 88 can be synthesized from the diamide 87 via a modification of a literature procedure of Gaugain, et al., *Biochemistry,* Vol. 17, No. 24, 1978, pp. 5071–5078 for quarternization of the diamide of 3,8-diamino-6-phenyl phenanthridine. Diamide 87 (0.023 moles) is placed in a 2.0 liter round bottom flask under Argon and is equipped with magnetic stir bar and reflux condenser. 1,3-Dibromopropane (1.0 liter, 9.86 moles) is added to this flask and the resultant mixture is brought to reflux for about 7 hours. The solution is cooled overnight and the precipitant is filtered and washed with $Et_2O$. This material can be recrystallized from $CH_3OH$ to yield diacetyl bromide 88 which can be characterized by mass spectrometry and other methods known to those skilled in the art.

Compound 88 (0.0081 moles) is added to a 250 ml round bottom flask equipped with a magnetic stir bar and reflux condenser. Methanol (150 ml) is then added to this flask while stirring under nitrogen and the diethylene triamine (0.283 moles), which is available from the Aldrich Chemical Company, is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the second filtrate upon standing and by precipitation with EtOH from the first filtrate. These solids are then combined and the product 89 can be obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Synthesis and purification of the final product 90 can be accomplished by the following protocol. The diamide (0.0036 moles) 89 is dissolved in 75.0 ml methanol and 75 ml of 4N HCl is added. The mixture is refluxed for 2 hours and allowed to cool. Ethanol is added to this solution and resulting precipitate is filtered and washed with a minimal amount of cold ethanol. The filtrate is reconcentrated and fresh ethanol and concentrated aqueous HCl is added. This resulting precipitate is also filtered. Next, this filtrate is concentrated to near dryness and EhO is added and the solid filtered off. The last remaining unfilterable residue is then dissolved in concentrated HCl and precipitated with EtOH. This material is filtered and washed with Ethanol. All solid materials, are combined from the above sequence and subjected to high vacuum overnight to obtain compound 90. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Amine derivatives of compound 88 can be synthesized as follows: Compound 88 (0.0081 moles) is added to a 250 ml round bottom flask equipped with a magnetic stir bar and reflux condenser. Methanol (150 ml) is then added to this flask while stirring under nitrogen and the appropriate amine selected from the following list (0.283 moles), which are available from the Chemical Company, is added while stirring is continued. The resultant solution is heated to reflux overnight under nitrogen. This solution is then allowed to cool to room temperature and is poured onto distilled $H_2O$. Then, this mixture is concentrated in vacuo until only the $H_2O$ remains. An additional 50–75 ml $H_2O$ is added and the reaction mixture is cooled to 0° C. The solid is filtered and washed with ice cold water. This material is then redissolved in EtOH and precipitated with 10 N HCl. After filtration of this suspension, the resultant solid is recrystallized from hot ethanol upon cooling to 0° C. for 15 minutes. A second crop is also collected from the $2^{nd}$ filtrate upon standing and by precipitation with EtOH from the first filtrate. These solids are then combined and the product 48a–48o is obtained and is subjected to high vacuum overnight. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

By combining the generic procedure for the synthesis of phenanthridinium derivatives 28a–42a and 28b–42b with the above procedures for the synthesis of bromide compound 88, 83, 78, 63 or 49, any combination of amine tail—intercalator molecular segments using the generic procedure for alkylation of bromides with amines as already described above can be synthesized, except that for derivatives of compounds 49 and 63, no hydrolysis step is need so the hydrolysis step is eliminated. In the case of derivatives of compound 78 no hydrolysis step will be needed but a reduction step is needed according to the procedure of Dervan et al., *J. Am. Chem. Soc.*, 100 (6), 1978, pp. 1968–1970.

EXAMPLE 23

General Procedure To Form A "Matrix" Of Compounds

Synthesis and purification of the final product 88aa–88oo can be accomplished by the following protocol to yield the corresponding final products as shown below. The imide (0.0036 moles) 88a–88o is dissolved in 75.0 ml methanol and 75 ml of 4N HCl is added. The mixture is refluxed for 2 hours and allowed to cool. Ethanol is added to this solution and resulting precipitate is filtered and washed with a minimal amount of cold ethanol. The filtrate is reconcentrated and fresh ethanol and concentrated aqueous HCl is added. This resulting precipitate is also filtered. Next, this filtrate is concentrated to near dryness and $Et_2O$ is added and the solid filtered off. The last remaining unfilterable residue is then dissolved in concentrated HCl and precipitated with EtOH. This material is filtered and washed with Ethanol. All solid materials are combined from the above sequence and is subjected to high vacuum overnight to obtain 88aa–88oo. Characterization can be effected by calculating the molecular mass of the free base amine from the exact isotopic mass formulas well known to those skilled in the art and comparing the resultant mass with that obtained by a high resolution mass spectrometry molecular weight determination such as are well known to those skilled in the art.

Listed below are the products that can be obtained from their corresponding immediate precursors.

88a to yield 88aa
88b to yield 88bb
88c to yield 88cc
88d to yield 88dd
88e to yield 88ee
88f to yield 88ff
88g to yield 88gg
88h to yield 88hh
88i to yield 88ii
88j to yield 88jj
88k to yield 88kk
88l to yield 88ll
88m to yield 88mm
88n to yield 88nn 88o to yield 88oo Since the structures of compounds 88a–88o and 88aa–88oo are unambiguous from the generic procedures, their structures are not shown.

EXAMPLE 24

Hybridization Assay Using Compounds 24–27

In four separate experiments, PTA 24 compound 25, compound 26, and compound 27 were used to quantitate hybridization when a target oligonucleotide was titrated with its complementary partner. By also conducting three simultaneous but independent experiments, a comparison of ethidium bromide staining, propidium iodide staining and ethidium homodimer staining verus PTA 24 was made as follows. Results can be found in FIG. 3 1. Results of a comparison of ethidium bromide staining, compound 24 (PTA) staining, compound 25 staining, compound 26 staining and compound 27 staining, as per the following protocol, are found in FIG. 32, Complementary strands of DNA oligodeoxythymidylic acid, $d(pT)_9$, and oligodeoxyadenylic acid, $(d(pA)_9)$, were obtained from the Sigma Chemical Co. in St. Louis, Mo. A stock solution of $d(pA)_9$ was made at 5.0 units/0.5 ml of 0.004 M TRIS, 0.001 M EDTA, pH 8.2 buffer. For polyA, $\epsilon=8.4$ AU/mM cm or 8400 $M^{-1}cm^{-1}$; Therefore, with 9 base pairs for $d(pA)_9$, the $\epsilon$ is 75,600 $M^{-1}cm^{-1}$. This stock was then diluted 100X to obtain stock at $6.61\times10^{-7}$M, or 0.66 μM. The d(pT)9 stock was made at 25 units/5.0 ml and used for titration after dilution 10X with the same buffer. Since the $\epsilon$ for polyT is 8.15 AU/mM cm or 8,150 $M^{-1}cm^{-1}$ per base pair, or 73,350 $M^{-1}cm^{-1}$ per oligo, the concentration of the oligo stock was 6.8 μM in DNA molecules. A titration was performed using a Hitachi F-4010 Fluorescence Spectrophotometer using polystyrene disposable 4.0 ml cuvettes to obtain a fully corrected spectra and an excitation wavelength of 488–550 nm (using 488 nm for this experiment) and an emission wavelength of 600–650 nm (using 625 nm for this experiment). Equivalents of $d(pT)_9$ were added at the following increments: 0,020, 0,080, 0.150, 0.300, 0.500, 0,700, 1,000, 2,000, 5,000 equivalents. Each sample in the titration curve was prepared individually by dividing the initial $d(TA)_9$ stock in 10×1.0 ml increments. The addition of complement was then accomplished by micropipetting an appropriate amount (2, 5, 8, 15, 30, 50, 70, 100, 200, and 500 μl, respectively) of d(pT)9 stock to each of a series of the 10 aliquots. Each aliquout, containing progressively larger molar ratios of the two complementary strands, was incubated a ambient temperature for 1 hr 5 minutes, the corresponding dye was added as 100.0 μl aliquots of a 15 μM solution of the corresponding dye in 0.004M TRIS, 0.001M EDTA, pH 8.2 buffer. This corresponds to a dye/DNA b.p. ratio of ¼ at saturation with complementary oligo. Overall concentrations of dye and oligo vary in the saturation plot because of the use of varied increments additions from the same stock solution. After an additional 45 minutes incubation time after addition of the corresponding appropriate dye, the relative fluorescence intensity was read at 625 am and recorded to generate a standard curve which is directly proportional to the quantity of dsDNA hybridization, or target sequence, under the same conditions. The background, or initial residual fluorescence, is then substrated out as a constant for all curves for comparison of the various titration curves on the same graphs.

Figure 32:
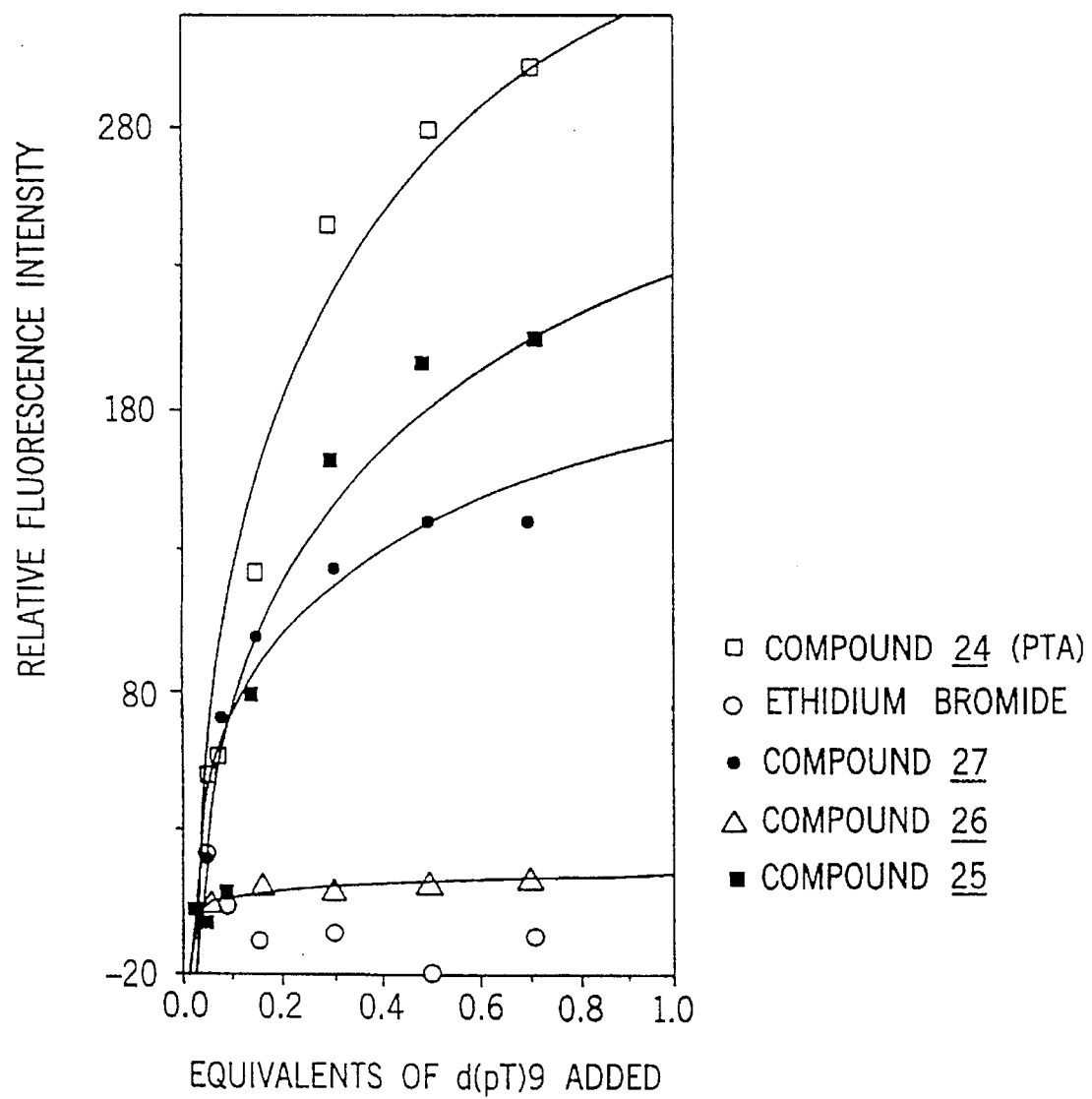
FIG. 32 is a comparison of relative fluorescence intensities obtained from staining DNA by compounds 24, 25, 26, 27, and ethidium bromide.

It is apparent to those skilled in the an that the high binding affinity of the intercalator compounds 24, 25, 26, or 27 of the present invention is especially useful relative to conventional intercalators such as ethidium bromide (FIG. 32). In FIG. 32 (EXAMPLE 24), the sensitivity or response to ds-DNA concentration in the presence of intercalator compounds 24, 25, 26, and 27 is shown compared to ethidium bromide. When concentrations of oligonucleotide are less than $10^{-6}$M, the advantages of such high affinity intercalators is especially apparent.

In comparison of PTA 24 to homobifunctional intercalators such as ethidium homodimer (FIG. 32), again a clear advantage is sensitivity is observed. In this case, the increased sensitivity may be related to reduced self-quenching in the PTA 24 as well as its high affinity for DNA.

In FIG. 3 and FIG. 9, the concentration of ds-DNA was higher and the differential between the ethidium bromide and PTA 24 (FIG. 9) and ethidium homodimer and PTA 24 (FIG. 8) was not significant because of the higher concentration of DNA used.

In summary, the present invention offers clear advantages in allowing the detection of ds-DNA hybridization at much lower concentrations than conventional staining methods currently available or known in the art.

EXAMPLE 25

Hybridization Assay/Using Intercalator Compound 1, 2, 3, 24, 25, 26, 27, 28b, 29b, 30b, 31b, 32b, 33b, 34b, 35b, 36b, 37b, 38, 39b, 40b, 41b, 42b, or 80

DNA Intercalator 1, 2, 3, 24, 25, 26, 27, 28b, 29b, 30b, 31b, 32b, 33b, 34b, 35b, 36b, 37b, 38, 39b, 40b, 42b, 42b, or 80 can be used to quantitate hybridization when a target oligonucleotide is titrated with its complementary partner. Complementary strands of DNA oligodeoxythymidylic acid, $d(pT)_9$, and oligodeoxyadenylic acid, $(d(pA)_9)$, can be obtained from the Sigma Chemical Co. in St. Louis, Mo. A stock solution of d(pA)9 is made at 5 units/ml of 0.05M TRIS, 0.2N NaCl, 1 mM EDTA, pH 8.4 or other suitable buffer. For polyA, $\epsilon=8.4$ AU/mM cm or 8,400 $M^{-1}cm^{-1}$; therefore, with 9 base pairs for d(pA)9, the $\epsilon$ is 75,600 $M^{-1}cm^{-1}$. This stock is then diluted to obtain stock from 0.066–66 μM. The $d(pT)_9$ stock is made at 25 units/5.0 ml and used for titration without further dilution in the same buffer. Since the $\epsilon$ for polyT is 8.15 AU/mM cm or 8,150 M-1cm$^{-1}$ per base pair, or 73,350 M-1cm$^{-1}$ per oligo, the concentration of the oligo stock is 0.0068–660 μM in DNA molecules. A titration can be performed using a Fluorescence Spectrophotometer using an excitation wavelength of 488–550 nm (optimal around 534) and an emission wavelength of 600–650 nm (optimal around 625). Equivalents of $d(pT)_9$ is added at the following increments: 0.02, 0.05, 0.080, 0.150, 0.300, 0.500, 0.700, 1.00, 2.00, 5.00 equivalents. Each sample in the titration curve is prepared individually by dividing the initial d(pA)9 stock into 10×1.0 ml aliquots. The addition of complement is then accomplished by micropipetting an appropriate amount (2, 5, 8, 15, 30, 50, 70, 100, 200, and 500 μl, respectively) of d(pT)9 stock to each of a series of the 10 aliquots when the d(pT)9 stock is 10X the concentration of the d(pA)9 stock. Each aliquot, obtaining progressively larger molar ratios of the two complementary strands, is incubated at ambient temperature for 0.25–2.5 hours, the dye is added as 1–500 μl aliquots of a 1–1000 μM solution of the dye in 0.05M TRIS, 0.2N NaCl, 1 mM EDTA, pH 8.4 buffer or other suitable buffer. This corresponds to a dye/DNA b.p. ratio of 1/1–1/1000 at saturation with complementary oligo. Overall concentrations of dye and oligo vary in the saturation plot because of the use of varied increments additions from the same stock solution. After an additional 15 minute incubation time, the relative fluorescence intensity is then read at between 580–680 mn and recorded to generate a standard curve which is directly proportional to the quantity of dsDNA hybridization, or target sequence, under these conditions.

EXAMPLE 26

Determination of Hybridization of Complementary Binding Pairs Other Than d(pT)9 and d(dA)9 Using Intercalator Compound 1, 2, 3, 24, 25, 26, 27, 28b, 29b, 30b, 31b, 32b, 33b, 34b, 35b, 36b, 37b, 38.39b, 39b, 40b, 41b, 42b, or 80

By using the above described procedure from EXAMPLE 25, interealator compound 1, 2, 3, 24, 25, 26, 27, 28b, 29b, 30b, 31b, 32b, 33b, 34b, 35b, 36b, 37b, 38, 39b, 40b, 41b, 42b, or 80 can be used to determine the quantity of hybridization of any other complementary DNA strands by substituting d(pT)9 with the appropriate complementary DNA and substituting d(pA)9 with the appropriate target DNA at appropriate concentrations that are determined by one skilled in the art and depending on the degree of complementary regions that are expected as is determined by one skilled in the art. In each case, the excitation wavelength of 450–550 nm (optimal at 534 nm) can be used and the relative fluorescence intensity is then read at between 580–680 nm and recorded to generate a standard curve which is directly proportional to the quantity of dsDNA hybridization, or target sequence, under these conditions.

EXAMPLE 27

Hybridization Assay using Interealator Compound 7, 8, 50, 54a, 54b, 54c, 54d, 54e, 54f, 54g, 54h, 54i, 54j, 54k, 54l, 54m, 54n, 54o, 54p, 58a, 58b, 58c, 58d, 58e, 58f, 58g, 58h, 58i, 58j, 58k, 58l, 58m, 58n, 58o, 58p, 64, 68a, 68b, 68c, 68d, 68e, 68f, 68g, 68h, 68i, 68j, 68k, 68l, 68m, 68n, 68o, 68p, 71a, 71b, 71c, 71d, 71e, 71f, 71g, 71h, 71i, 71j, 71k, 71l, 71m, 71n, 71o, or 71p By using the above procedure in EXAMPLE 26, the hybridization of any two complementary strands can be determined using intercalator compound 7, 8, 50, 54a, 54b, 54c, 54d, 54e, 54f, 54g, 54h, 54i, 54j, 54k, 54l, 54m, 54n, 54o, 54p, 58a, 58b, 58c, 58d, 58e, 58f, 58g, 58h, 58i, 58j, 58k, 58l, 58m, 58n, 58o, 58p, 64, 68a, 68b, 68c, 68d, 68e, 68f, 68g, 68h, 68i, 68j, 68k, 68l, 68m, 68n, 68o, 68p, 71a, 71b, 71c, 71d, 71e, 71f, 71g, 71h, 71i, 71j, 71k, 71l, 71m, 71n, 71o, or 71p as described in EXAMPLE 26 except the wavelengths of excitation and emission are optimized as determined by one skilled in the art before conducting the assay. In each case, the relative fluorescence intensity is then read and recorded to generate a standard curve which is directly proportional to the quantity of dsDNA hybridization, or target sequence, under these conditions.

EXAMPLE 28

Hybridization Assay for d(pT)9 and d(pA)9 using Intercalator Compound 7, 8, 50, 54a, 54b, 54c, 54d, 54e, 54f, 54g, 54h, 54i, 54j, 54k, 54l, 54m, 54n, 54o, 54p, 58a, 58b, 58c, 58d, 58e, 58f, 58g, 58h, 58i, 58j, 58k, 58l, 58m, 58n, 58o, 58p, 64, 68a, 68b, 68c, 68d, 68e, 68f, 68g, 68h, 68i, 68j, 68k, 68l, 68m, 68n, 68o, 68p, 71a, 71b, 71c, 71d, 71e, 71f, 71g, 71h, 71i, 71j, 71k, 71l, 71m, 71n, 71o, or 71p By using the above described procedure in EXAMPLE 25, complementary oligonucleotide d(pA)9 and d(pT)9 hybridization can be determined except that the wavelengths are subtituted to optimal wavelengths for each compound as is determined by one skilled in the art. The described procedure is then followed using the optimal wavelengths as are determined.

EXAMPLE 29

Gel Electrophoresis Application Using Intercalator Compound 1, 2, 3, 25, 26, 27, 28b, 29b, 30b, 31b, 32b, 33b, 34b, 35b, 36b, 37b, 38b, 39b, 40b, 41b, 42b, or 80

An agarose gel can be run to detect DNA using compound 1, 2, 3, 25, 26, 27, 28b, 29b, 30b, 31b, 32b, 33b, 34b, 35b, 36b, 37b, 38b, 39b, 40b, 41b, 42b, or 80. Plasmid, pBR322, at 2.1 mg in 7 ml stock is incubated at 37° C. for 1 hour with 1 ml of BAMH restriction enzyme with 2 ml 10X React2 Buffer and diluted to 20 ml total with 10 ml $H_2O$. Alternatively, any other appropriate DNA sample is substituted for the above described "nicked" plasmid. This mixture is then used to prepare 3 stocks of nicked pBR322 plasmid at 0.63 mg per 6 ml for each vial. Each of these stocks is diluted further with $H_2O$ and 20% glycerol to final DNA stocks of 20 ng/ml, 800 pg/ml, 160 pg/ml, and 40 pg/ml with a 1:4 ratio of dye to DNA base pairs in each for a total of 12 stocks. A 5 µl aliquot of each stock is loaded into 12 separate lanes in agarose gel and electrophoresis is run for 30 minutes in 4 mM TRIS, pH8.2, with 0.01mM EDTA buffer. The gel is then removed and photographed under exposure to U.V. light in a conventional gel box. Alternatively, the gel is scanned using fluorescence confocal microscopy or charge coupled device imaging as a fluorescence detection or visualization method.

EXAMPLE 30

Protocol for Synthesis Of Intercalator Activated Carboxymethyl Styrene Microparticle Capture Reagent Using Intercalator Compound 25, 26, 27, 29b, 35b, 38b, 50, 54a, 54c, 58a, 58c, 64, 68a, 68c, 71a, 71c, 80, 85, or 90

The synthesis of intercalator derivatized solid phase microparticle (MP) capture reagent can be accomplished by the following procedure:

A 45 aliquot of 0.275±µm microparticles (Seradyne, Indianapolis, Ind.) is placed in a 4 ml vial and the surfactant is exchanged out using Bio-Rex 501-D ion exchange mixed bed resin (Bio-Rad, Richmond, Calif.). After gentle shaking for 2 hours, the resin is filtered out from the mixture by using a coarse flitted glass funnel equipped with a reduced pressure collection chamber. The sample is diluted to a concentration of mp at 10% solids by weight. The total amount of equivalents of reactive carboxylic acid is calculated from the titration specifications of the vendor. A stock solution of sulfo N-hydryoxysuccinimide (Pierce, Rockford, Ill.) is made at 11 mg/ml (20 mM) in $H_2O$ and a stock solution of EDAC (Sigma Chemical Co., St. Louis, Mo.) at 10 mg/ml (5 mM) is made in $H_2O$. Five equivalents of EDAC (290 µl stock) is added to the carboxymicroparticle reaction mixture, followed by 5.0 equivalents of sulfo N-hydryoxysuccinimide (330 µl stock). This mixture is allowed to incubate at room temperature for 2 hours and then a 2.0 molar equivalent of interealator compound 25, 26, 27, 29b, 35b, 38b, 50, 54a, 54c, 58a, 58c, 64, 68a, 68c, 71a, 71c, 80, 85, or 90 (4 mg) is added at a concentration of 8 mg/400 µl, or 2.0 mg/100 µl in pH 8.0 0.1 N NaCl 0.1N Pi phosphate buffer. N-hydryoxysuccinimide (Pierce) can be substituted for sulfo N-hydryoxysuccinimide if it is first dissolved in a stock of DMF (Dimethyl formamide) and aliquoted as described above. After allowing 24 hours for complete reaction, the free dye is then removed by centrifugation, removal of mother liquor, and resuspension for several attempts until the solution went clear and no more dye is extracted from the samples. The purified capture reagent is then diluted to a stock of 2–4% solids in $H_2O$.

EXAMPLE 31

Solid Phase DNA Capture using Solid Phase Derived From Compound 25, 26, 27, 29b, 35b, 38b, 50, 54a, 54c, 58a, 58c, 64, 68a, 68c, 71a, 71c, 80, 85, or 90

The capture of DNA onto solid phase can be performed using derivatization methods as described in EXAMPLE 5 except substituting the appropriate solid phase synthesized from the respective intercalator 25, 26, 27, 29b, 35b, 38b, 50, 54a, 5c, 58a, 58c, 64, 68a, 68c, 71a, 71c, 80, 85, or 90 as described in EXAMPLE 30.

Other appropriate solid phases such as carboxylated polystyrene microparticles or carboxylated magnetic microparticles can are also used instead of CM Sepharose.

EXAMPLE 32

Protocol for DNA Capture by Intercalator Modified Solid Phase Modified By Compound 25, 26, 27, 29b, 35b, 38b, 50, 54a, 54c, 58a, 58c, 64, 68a, 68c, 71a, 71c, 80, 85, or 90

DNA can be released from solid phase as described in EXAMPLE 6 except that corresponding solid phase derived from intercalator compound 25, 26, 27, 29b, 35b, 38b, 50, 54a, 54c, 58a, 58c, 64, 68a, 68c, 71a, 71c, 80, 85, or 90 is used rather than the PTA 24 derivatized interealator.

EXAMPLE 33

Fluorescence Staining in a Flow Cytometric Study of Chicken Erythrocyte Nuclei (CEN)

Protocol: 50 µl of whole blood sample from two in-house donors and 3 µl of CEN suspension is added to 1.0 ml of pre-warmed at 40° C. WBC DIL without and with the compound 1, 2, 3, 25, 26, 27, 28b, 29b, 30b, 31b, 32b, 33b, 34b, 35b, 36b, 37b, 38, 39b, 40b, 41b, 42b, or 80 at 1 µg/ml concentration, mixed, introduced to the FACScan™ and 20" readings is acquired. Chicken erythrocyte nuclei (CEN) is used to measure the brightness of the FL3 staining (mean FL3 of CEN). The whole blood samples used is about 4–5 hours old.

EXAMPLE 34

Viability Dyes on the Coulter Elite Flow Cytometer Using Compound 1, 2, 3, 25, 26, 27, 28b, 29b, 30b, 31b, 32b, 33b, 34b, 35b, 36b, 37b, 38, 39b, 40b, 41b, 42b, or 80

Cell Isolation Protocol: Each tube of ficol isolated cells can be treated as follows: PBS with 0.1% NaAzide and 1.0% albumin (Sigma catalogue #1000-3) Ficol specific gravity 1.119 (Sigma Histopague catalogue #1119-1).

10 ml of whole blood (EDTA anticoagulant) is diluted with 10 ml of PBSW. Into 4, 15 ml conical bottom tubes, 5 ml of the diluted blood is layered over 5 ml of ficol. The tubes is spun for 30 minutes at 400×G. The interface layer which contains the lymphocytes, monocytes, granulocytes and platelets is aspirated and washed once in 5 ml PBS, by centrifuging tubes at 300×G for 6 minutes. The cell pellet is resuspended in PBS, cells counted, and adjusted to 8.5×106 cells per mi.

Cell Staining Protocol:

Dye or compound solutions:

Compound 1, 2, 3, 25, 26, 27, 28b, 29b, 30b, 31b, 32b, 33b, 34b, 35b, 36b, 37b, 38, 39b, 40b, 41b, 42b, or 80—Stock solution 10 µg/ml made by dissolving dye in PBS with 0.1% NaAzide.

Staining of compound 1, 2, 3, 25, 26, 27, 28b, 29b, 30b, 31b, 32b, 33b, 34b, 35b, 36b, 37b, 38, 39b, 40b, 41b, 42b, or 80: In 12×75 mm tube, 23.5 µl of cells is gently mixed with 76 µl of the compound stock solution. After 20 seconds, the tube is placed on Elite flow cytometer and data collected.

Flow Cytometer protocol: Cells analyzed on the Elite flow cytometer (Coulter Electronics, Inc.).

Samples can be excited with an argon laser at 488 nm and 15 mW of power. Data is gated on the basis of size and granularity to exclude red blood cells, platelets-and debris. The linear dye fluorescence of the gated distribution is analyzed using unstained cells as a control. The percent positive events (dead cells) and the mean fluorescence of the dead cell distribution is recorded.

EXAMPLE 35

Conjugates of Intercalator Derivatized Antibodies and Intercalator Derivatized Alkaline Phosphatase Using Double Stranded Nucleic Acids as Conjugation Templates Complementary strands of oligonucleotides, sense and antisense 14 to 20-mers, can be synthesized on a fully automated DNA synthesizer and purified as described in *Bioconjugate Chemistry*, 4, pp. 94–102, (1993). The synthesis of the conjugate between the enzyme calf intestinal alkaline phosphatase and IgG can be accomplished as follows.

a) Derivatization of the Intercalator PTA 24 with 30 Atom Heterobifunctional Linker Arm, 4-[(N-maleimidomethyl-)tricaproamid o]cyclohexane-1-carboxylate (SMTCC).

PTA 24, 0.100g ($2.3 \times 10^{-4}$ mole), is dissolved in 5 ml of 50% aqueous DMF (dimethylformamide). 30 atom heterobifunctional linker, 4-[(N-maleimidomethyl)tricaproamido] cyelohexane-1-carboxylate (SMTCC), 0.157 g, ($2.3 \times 10^{-4}$ mole) synthesized as described in Bieniarz et al., U.S. Pat.

Nos. 4,994,385, 5,002,883, 5,053,520, and 5,063,109 is dissolved in 3 ml of DMF and is added in one portion to the solution and stirred over 24 h at ambient temperature. The resulting maleimide derivatized PTA 24 contains is purified on silica gel column using 10% methanolic acetone as eluent.

b) Derivatization of the Calf Intestinal Alkaline Phosphatase with Iminothiolane.

Calf intestinal alkaline phosphatase, 6 mg ($4 \times 10^{-9}$ mole) in 1 ml of PBS buffer is thiolated by treatment with a 450-fold molar excess of iminothiolane (164 ml of a 15 mg/ml solution in PBS buffer) for 30 min at ambient temperature. Excess reagent is removed by gel filtration with a Sephadex G-25 column (1×45 cm) equilibrated with PBS buffer. The fractions containing the derivatized enzyme are pooled and the concentration of the enzyme in the pool is calculated by absorbance at 280 nm.

c) Conjugation of the SMTCC Derivatized PTA 24 to the Thiolated Calf Intestinal Alkaline Phosphatase from b).

The thiolated calf intestinal alkaline phosphatase from part b) and maleimide derivatized PTA 24 from part a) are combined at molar ratio 1:1 and incubated 18 h at 5° C. Unreacted thiol groups are capped by addition of 5 mM N-ethylmaleimide to 0.3 mM final concentration followed by 1 h incubation at ambient temperature.

d) Derivatization of IgG with thiolares using site-specific functionalization of the Fc region of IgG. Site-specific introduction of thiolares into Fc region of IgG is accomplished as described in Bieniarz et al., U.S. Pat. No. 5,191,066. In that way, between 4 and 10 thiolates are introduced into Fc region of the IgG.

e) Derivatization of the Fc Thiolated IgG from part d) with maleimide derivatized PTA 24 from part a).

The Fc thiolated IgG from part d) and maleimide derivatized PTA 24 from part a) are combined at molar ratio of 1:5 of thiolated IgG to SMTCC derivatized PTA 24. The solution is incubated in phosphate buffer pH 7.0 for 18 h at 5° C. and the conjugate is purified on gel filtration column Sephadex G-25. Fractions containing proteins are pooled and concentrated using Amicon concentrator. Protein content of the final solution is established using Coomassie Dye Binding Assay, from Pierce Company.

f) Conjugation of the PTA 24 derivatized IgG from part e) to the PTA 24 derivatized calf intestinal alkaline phosphatase from part c) using double stranded 20-mer oligonucleotide composed of the complementary strands of the oligos.

Complementary strands of oligonucleotides are hybridized and examined as described in *Bioconjugate Chemistry*, 4, pp. 94–102, (1993). PTA 24 derivatized IgG from part e), PTA 24 derivatized calf intestinal alkaline phosphatase and double stranded oligonucleotide 20-mer used as the conjugation template are incubated overnight at pH 7.0 for 18 h in molar ratios of 1:1:1 at ambient temperature. The conjugate is filtered through a gel filtration column G-25. The fractions are assayed for alkaline phosphatase activity using fluorogenic substrate 4-methylumbelliferyl phosphate, and for the antibody activity using the antiidiotypic IgG labelled with fluorescein.

The conjugate is also examined by gel filtration HPLC columns.

EXAMPLE 36

Conjugation of Intercalator Derivatized Liposome to a Double Stranded DNA

Preparation of the liposomes is carried as described in Fiechtner et al., U.S. Pat. No. 4,912,208. These liposomes display on their surface primary amines because they are prepared from diphosphatidiylethanolamine lipids. The preparation of the liposomes is carried in presence of membrane impermeable fluorescent dyes disclosed in U.S. Pat. No. 4,912,208. Thus, the molecules of the fluorescent dyes are substantially at very high, self quenching concentrations inside the liposomes and consequently they are nonfluorescent. The surface amines of the liposomes are derivatized with thiolates by essentially the same method used to introduce thiolates into alkaline phosphatase described in the EXAMPLE 35. PTA 24 and other intercalators disclosed in the preceding examples are derivatized with maleimides, utilizing SMTCC reagent, as described in EXAMPLE 35. Thiolate derivatized liposomes and maleimide derivatized PTA 24 or other intercalators are incubated together in a vessel under conditions esentially identical to the ones described in EXAMPLE 35. The fluorescent dye containing liposomes derivatized with multiple intercalators are incubated at pH ranging from 5 to 9, preferably 7.0 with the sample containing small concentrations of the double stranded DNA coated or immobilized on a solid phase. The incubation is followed by wash and addition of detergent. The concomitant lysis of the liposome membrane results in spilling of the fluorogenic dye, dequenching of the fluorescence and appearance of signal.

Alternatively, the probe multimerit single stranded DNA may be immobilized on a solid phase; the patient sample suspected to contain a complementary single stranded DNA is incubated in presence of the probe; the liposome-intercalator is brought in contact with the hybridized sample and the contents of the vessel are incubated and washed several times to remove excess of the PTA 24 derivatized liposomes. If the probe finds a complementary sequence in the patient sample, the addition of the detergent results in lysis of the liposomes and signal. If however the probe and patient sample DNA strands are not complementary, no double stranded DNA is present and substantially all the PTA 24 derivatized liposome is washed away from the solid phase, resulting in no signal.

EXAMPLE 37

Detection of DNA Using A Fluorescent Intercalator Conjugate Derived From Intercalator Compound 24, 25, 26, 27, 29b, 35b, 38b, 50, 54a, 54c, 58a, 58c, 64, 68a, 68c, 71a, 71c, 80, 85, or 90

The synthesis of intercalator maleimide functionalized intercalator can be effected by the procedure as already described in EXAMPLE 35 except that the intercalator compound 25, 26, 27, 29b, 35b, 38b, 50, 54a, 54c, 58a, 58c, 64, 68a, 68c, 71a, 71c, 80, 85, or 90 is used in place of PTA 24. An appropriate signal generating entity such as phycoerythrin or allophycocyanine is covalently attached to this maleimide derivatized intercalator through a thiolate on the thiolated protein prepared as described in EXAMPLE 35. After allowing time for binding of the intercalator portion of the conjugate to the immobilized ds-DNA molecule and washing away the unbound conjugate, then double stranded DNA is detected on the solid phase or other immobilized entity using the fluorescence of the phycoerythrin that is localized by the binding of the intercalator portion to the double stranded DNA molecule. The fluorescence emission is read at approximately 580 nm using methods known to those skilled in the art while exciting the fluorescent protein at a wavelength that is appropriate for efficient excitation as is determined by one skilled in the art.

EXAMPLE 38

Detection of DNA Using an Enzyme Intercalator Conjugate Derived From Intercalator Compound 24, 25, 26, 27, 29b, 35b, 38b, 50, 54a, 54c, 58a, 58c, 64, 68a, 68c, 71a, 71c, 80, 85, or 90

The synthesis of intercalator maleimide functionalized intercalator can be effected by the procedure as already described in EXAMPLE 35 except that the intercalator compound 25, 26, 27, 29b, 55b, 38b, 50, 54a, 54c, 58a, 58c, 64, 68a, 68c, 71a, 71c, 80, 85, or 90 is used in place of PTA 24. An appropriate signal generating entity such as alkaline phosphatase, β-galactosidase, esterase, or β-lactamase is covalently attached to this maleimide derivatized intercalator through the thiolate of the thiolated protein that is prepared as described in EXAMPLE 35. After allowing time for binding of the intercalator portion of the conjugate to the immobilized ds-DNA molecule and washing away the unbound conjugate, then double stranded DNA is detected on the solid phase or other immobilized entity such as a colloid or microparticle by fluorescence or chemiluminscence afforded by the turn-over of a non-fluorescent or non-chemiluminescent substrate of the appropriate enzyme to a fluorescent or chemiluminescent entity respectively as is determined by one skilled in the art. The fluorescence emission or chemiluminescence is then read at at the appropriate wavelengths by using standard methods of fluorescence excitation or detection of chemiluminescence respectively that are known to those skilled in the art.

EXAMPLE 39

Detection of DNA Using an Intercalator—Chemiluminophore Conjugate Derived from Intercalator Compound 24, 25, 26, 27, 29b, 35b, 38b, 50, 54a, 54c, 58a, 58c, 64, 68a, 68c, 71c, 80, 85, or 90

The synthesis of intercalator maleimide functionalized intercalator can be effected by the procedure as already described in EXAMPLE 35 except that the intercalator compound 25, 26, 27, 29b, 35b, 38b, 50, 54a, 54c, 58a, 58c, 64, 68a, 68c, 71a, 71c, 80, 85, or 90 is used in place of PTA 24. An appropriate activatable chemiluminescent signal generating entity such as acridinium sulfonamide is covalently attached to this intercalator by thiolate of the chemiluminescent entity that is prepared so as to be reactive towards the maleimide such as can be devised by one skilled in the art. After binding of ds-DNA with the intercalator chemiluminophore conjugate, the excess or unbound conjugate is washed away and double stranded DNA is then detected on the solid phase or other immobilized entity by direct chemiluminscence triggered by the addition of an appropriate activation reagent such as hydrogen peroxide leading to a chemiluminescent entity and chemiluminescence is then read at at the appropriate wavelengths by using standard methods of detection of chemiluminescence such as are known to those skilled in the art.

EXAMPLE 40

Synthesis Of Intercalator Derivatized Dendrimer

Intercalator derivatized dendrimer can be synthesized from Dendritic Polymers obtained from PolySciences. The intercalator bromide intermediates 22, 49, 58, 63, 71, 83, or 88 is used to alkylate the amines on the 3rd, 4th, 5th, 6th, 7th, 8th, 9th, or 10th generation dendrimer by heating in dimethyl formamide or other appropriate organic solvent to between 30°–90° C. for 0.25–72 hours. The product is then purified in the case of when intercalator compound 58, 63, or 71 is used by using size exclusion chromatography on a G-25 SephadexTM column in water or an appropriate aqueous buffer and the intercalator derivatized dendrimer is obtained. In the case of intercalator compound 22, 83, or 88, the column in G-25 is run in water and the protected intercalator derivatized dendrimer is then isolated. This material is then subjected to heating to 90° C. for 2–4 hours in 4N HCl to hydrolyze the aromatic amine protecting groups and then the solution is neutralized to pH 4–10 and a G-25 column is run in an appropriate buffer on the final product to obtain pure intercalator derivatized dendrimer.

The various literature references on the general synthesis given in the examples above are hereby incorporated by reference.

Although the present invention and its advantages have been described in detail, those skilled in the art should understand that they can make various changes, substitutions and alterations herein without departing from the spirit and scope of the invention as defined by the appended claims.

We claim:
1. A compound having the formula

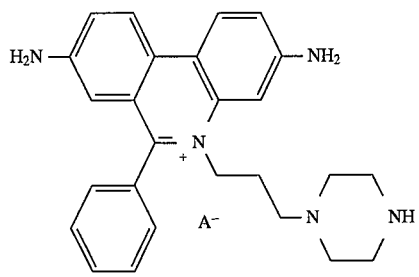

wherein $A^-$ is an acceptable monvalent counter anion.

2. The compound of claim 1, wherein said $A^-$ is selected from
the group consisting of chloride, bromide and iodide.

* * * * *